US006107482A

United States Patent [19]
Cook et al.

[11] Patent Number: 6,107,482
[45] Date of Patent: Aug. 22, 2000

[54] NITROGENOUS MACROCYCLIC COMPOUNDS

[75] Inventors: Phillip Dan Cook, Escondido; Haoyun An, Encinitas; Charles J. Guinosso, Vista; Pei-Pei Kung, Leucadia; Allister S. Fraser, San Marcos, all of Calif.

[73] Assignee: Isis Pharmaceuticals, Inc., Carlsbad, Calif.

[21] Appl. No.: 08/913,664

[22] PCT Filed: Mar. 27, 1996

[86] PCT No.: PCT/US96/04215

§ 371 Date: Sep. 19, 1997

§ 102(e) Date: Sep. 19, 1997

[87] PCT Pub. No.: WO96/30377

PCT Pub. Date: Oct. 3, 1996

Related U.S. Application Data

[63] Continuation-in-part of application No. 08/461,728, Jun. 5, 1995, which is a continuation-in-part of application No. 08/410,703, Mar. 27, 1995.

[51] Int. Cl.$^7$ .................................................. C07D 471/08
[52] U.S. Cl. ........................... 540/472; 540/455; 540/469
[58] Field of Search ..................................... 540/472, 455

[56] References Cited

U.S. PATENT DOCUMENTS

| | | | |
|---|---|---|---|
| 3,687,808 | 8/1972 | Merigan et al. | 195/28 |
| 4,987,227 | 1/1991 | Burrow et al. | 540/452 |
| 5,276,131 | 1/1994 | Akkapeddi et al. | 528/271 |
| 5,288,514 | 2/1994 | Ellman | 427/2 |
| 5,324,483 | 6/1994 | Cody et al. | 422/131 |
| 5,385,893 | 1/1995 | Kiefer | 514/80 |
| 5,403,572 | 4/1995 | Gries et al. | 424/9 |
| 5,410,045 | 4/1995 | Sessler et al. | 540/472 |
| 5,565,562 | 10/1996 | Parker et al. | 540/465 |

FOREIGN PATENT DOCUMENTS

| | | |
|---|---|---|
| WO 91/19735 | 12/1991 | WIPO . |
| WO 92/20822 | 11/1992 | WIPO . |
| WO 93/04204 | 3/1993 | WIPO . |
| WO 94/08051 | 4/1994 | WIPO . |
| WO 94/22454 | 10/1994 | WIPO . |
| WO 94/24314 | 10/1994 | WIPO . |
| WO 94/26775 | 11/1994 | WIPO . |
| WO 94/27719 | 12/1994 | WIPO . |
| WO 94/28028 | 12/1994 | WIPO . |
| WO 94/28424 | 12/1994 | WIPO . |

OTHER PUBLICATIONS

Karaman et al., J. Org. Chem., vol. 57, pp. 1555–1559, 1992.
Alul, R. et al., "Oxalyl–CPG: A Liable Support for Synthesis of Sensitive Oligonucleotide Derivatives", *Nucleic Acids Research*, 1991, 19, 1527–1532.
Beaucage, S. and Iyer, "Advances in the Synthesis of Oligonucleotides by the Phosphoramidite Approach", *Tetrahedron Letters*, 1992, 48, 2223–2311.
Bomalaski, J. et al., "Human Extracellular Recombinant Phospholipase A$_2$ Induces an Inflammatory response in Rebbit Joint", *J. Immunol.*, 1991, 146, 3904–3910.
Bradshaw, J. et al., "Aza–Crown Macrocycles", John Wiley & Sons, New York, NY 1993.
Carell, T. et al., "A Novel Procedure for the Syntehsis of Libraries Containing Small Organic Molecules", *Angew. Chem. Int. Ed. Engel.*, 1994, 33, 2061–2064.
Chem. abstr., vol. 124(7), issued 1996 (Columbus, Ohio, USA), p. 1319, col. 2, the abstract No. 87049y, Irie et al., "Method for Producing Carbamoyloxa–crosslinked Metacyclophane Compounds," JP 07–233,173 (Sep. 5, 1995), see entire abstract.
Dennis, E., "Phospholipases", *The Enzymes*, 16, Chapter 9, pp. 307–353, Boyer, P.D., ed., Academic Press, New York, 1983.
DeWitt, S.H. et al., "Diversomers : An approach to Non–peptide, Nonoligomeric Chemical Diversity", *Proc. Natl. Acad. Sci, USA*, 1993, 90, 6909–6913.
Dietrich, B. et al. (eds.), "Aspects of Organic and Inorganic Supramolecular Chemistry", *Macrocyclic Chemistry*, VCH, New York, NY, 1993.
Ecker, D. et al., "Rational Screening of Oligonucleotide Combinatorial Libraries for Drug Discovery", *Nucleic Acides Res.*, 1993, 21, 1853–1856.
Englisch, U. and Gauss, "Chemically Modified Oligonucleotides as Probes and Inhibitors", *Angew. Chem. Int. Ed. Engl.*, 1991, 30, 613–722.
Geysen, H. et al., "Strategies for Epitope Analysis Using Peptide Synthesis", *J. Immun. Meth.*, 1987, 102, 259–274.
Glaser, K., et al., "Phospholipase A$_2$ Enzymes: Regulation and Inhibition", *TiPs Reviews*, 1992, 14, 92–98.
Green and Wuts, *Protective Groups in Organic Synthesis*, 2d Edition, John Wiley & Sons, New York, 1991.
Hata, T. et al., "One–step Synthesis of 5'–Azido–nucleosides", *J. Chem. Soc. Perkin I*, 1980, 306–310.

(List continued on next page.)

*Primary Examiner*—Richard L. Raymond
*Attorney, Agent, or Firm*—Woodcock Washburn Kurtz Mackiewicz & Norris LLP

[57] ABSTRACT

Novel macrocyclic compounds are constructed to include large cyclic structures that are interrupted by at least one ring system. Each interrupting ring system includes two bridgehead atoms. Bridgehead atoms are bonded to one or more bridges that interconnect one or more ring systems thereby forming a large cyclic structure. Located in each bridge are two or more nitrogenous moieties that are derivatized with chemical functional groups. The ring systems can include further nitrogenous moieties, either as ring atoms or on pendant groups attached to the ring. These can also be derivatized with chemical functional groups. The totality of the chemical functional groups imparts certain conformational and other properties to the macrocyclic compounds. In accordance with certain embodiments of the invention, libraries of such macrocyclic compounds are prepared utilizing permutations and combinations of the chemical functional groups and the nitrogenous moieties to build complexity into the library.

6 Claims, 15 Drawing Sheets

OTHER PUBLICATIONS

Hiroshige et al., "Palladium–mediated Macrocyclization on Solid Support and Its Applications to Combinatorial Synthesis", *J. Am. Chem. Soc.,* 1995, 117, 11590–11591.

Houghten, R. et al., "Generation and Use of Synthetic Peptide Combinatorial Libraries for Basic Research and Drug Discovery", *Nature,* 1991, 354, 84–86.

Iwata et al., *Bull. Chem. Soc. Jpn.,* 1986, 59, 1031–1036.

Kikuchi et al., "Molecular Recognition by Macrocyclic Receptors Having Miltiple Hydrophobic Branches in a Synthetic Bilayer Membrane", *J. Phys. Org. Chem.,* 1992, 5, 633–643.

Koraman et al., *J. Org. Chem.,* 1992, 57, 1555–1559.

Kroschwitz, J.I. (ed.), "Concise Encyclopedia of Polymer Science and Engineering", 858–859, John Wiley & Sons, 1990.

McMurry, et al., "Convenient Synthesis of Bifunctional Tetraaza Macrocycles", *Bioconjugate Chem.,* 1992, 3, 108–117.

Mellor, D.P., Chemistry of Chelation and Chelating Agents in International Encyclopedia of Pharmacolaogy and Therapeutics, Section 70, The Chelation of Heavy Metals, Levine, W.G. Ed., Pergamon Press, Elmford, N.Y., 1979.

Ohlmeyer, M. et al., "Complex Synthetic Chemical Libraries Indexed with Molecular Tags", *Proc. Natl. Acad. Sci. USA,* 1993, 90, 10922–10926.

Owens, R. et al., "The Rapid Identification of HIV Protease Inhibitors Through the Synthesis and Screening of Defined Peptide Mixtures", *Biochem & Biophys. Res. Comm.,* 1991, 181, 402–408.

Pruzanski, W. et al., "Enzymatic Activity and Immunoreactivity of Extracellular Phospholipase $A_2$ in Inflammatory Synovial Fluids", *Inflammation,* 1992, 16, 451–457.

Saab, N.H. et al., "Synthesis and Evaluation of Unsymmetrically Substituted Polyamine Analogues as Modulators of Human Spermidine/Spermine–$N^1$–Acetyltransferase (SSAT) and as Potential Antitumer Agents", *J. Med. Chem.,* 1993, 36, 2998–3004.

Saari, W. et al., "Cyclization–Activated Prodrugs. Basic Carbamates of 4–Hydroxyanisole", *J. Med. Chem.,* 1990, 33, 94–101.

Simon, R. et al., "Peptoids: A Modular Approach to Drug Discovery", *Proc. Natl. Acad. Sci. USA,* 1992, 89, 9367–9371.

Sutherland, I.O., "Cyclophanes as Synthetic Receptors," *Pure Applied Chem.,* 1990, 62(3), 499–504.

Trofimenko, S., "1,1,2,2–Ethanetetracarboxaldehyde and Its Reactions", *J. Org. Chem.,* 1964, 29, 3046.

Vishwanath, B. et al., "Edema–Inducing Activity of Phospholipase $A_2$ Purified from Human Synovial Fluid and Inhibition by Aristolochic Acid", *Inflammmation,* 1988, 12, 549–561.

Vogtle, F., "Cyclophane Chemistry, Synthesis, Structures and Reactions", John Wiley & Sons, New York, NY 1993.

Vogtle et al., *Tetra. Lett.,* 1970, 2, 115–118.

Wright, P. et al., "Large Scale Synthesis of Oligonucleotides via Phosphoramidite Nucleosides and a High–loaded Polystyrene Support", *Tetrahedron Letters,* 1993, 34, 3373–3376.

Wyatt, J. et al., "Combinatorially Selected Guanosine–Quartet Structure is a Potent Inhibitor of Human Immunodeficiency Virus Envelope–Mediated Cell Fusion", *Proc. Natl. Acad. Sci. USA,* 1994, 91, 1356–1360.

Zuckerman, R. et al., "Efficient Method for the Preparation of Peptoids [Oligo (N–substituted glycines)] by Submonomer Solid Phase Synthesis", *J. Amer. Chem. Soc.,* 1992, 114, 10646–10647.

Achari et al., "Facing up to Membranes: Structure / Function Relationships in Phospholipases", *Cold Spring Harbor Symp. Quant. Biol.,* 1987, 52, Cold Spring Harbor Laboratory, 441–452.

Burack et al., "Role of Lateral Phase Separation in the Modulation of Phospholipase $A_2$ Activity", *Biochem.,* 1993, 32, 583–589.

Campbell et al., "Inhibition of Phospholipase $A_2$; a Molecular Recognition Study", *J. Chem. Soc., Chem. Comm.,* 1988, 1560–1562.

Carell et al., "A Novel Procedure for the Synthesis of Libraries Containing Small Organic Molecules", *Angew. Chem. Int. Ed. Engl.,* 1994, 33, 2059–2061.

Cho et al., "The Chemical Basis for Interfacial Activation of Monomeric Phospholipases $A_2$", *J. Biol. Chem.,* 1988, 263, 11237–11241.

Davidson et al., "Inhibition of Phospholipase $A_2$ by "Lipocortins" and Calpactins", *J. Biol. Chem.,* 1987, 262, 1698–1705.

Davidson et al., "1–Stearyl,2–Stearoylaminodeoxyphosphatidylcholine, A Potent Reversible Inhibitor of Phospholipase $A_2$", *Biochem. Biophys. Res. Comm.,* 1986, 137, 587–592.

Franson et al., "Phospholipid metabolism by phagocytic cells. Phospholipase $A_2$ associated with rabbit polymorphonuclear leukocyte granules", *J. Lipid Res.,* 1974, 15, 380–388.

Grainger et al., "An enzyme caught in action: direct imaging of hydrolytic function and domain formation of phospholipase $A_2$ in phosphatidylcholine monolayers", *FEBS Letts.,* 1989, 252, 73–82.

Gu, K. et al., "Strategy for the Synthesis of Unsymmetrical N–Substituted Polyazamacrocycles", *Tetrahedron Letts.,* 1989, 30, 1323–1326.

Krakowiak, K., "Attempts to Synthesize Biheterocyclic Systems Containing Pyridine Residue. Part I. Synthesis of of Diaza[7]–, [8]–, [9]–, [10](2,6) Pyridinophanes", *Polish J. Chem.,* 1986, 60, 277–281.

Lombardo et al., "Cobra Venom Phospholipase $A_2$ Inhibition by Manoalide", *J. Biol. Chem.,* 1985, 260, 7234–7240.

Märki, F. et al., "Differential inhibition of human secreory and cytosolic phospholipase $A_2$", *Agents Actions,* 1993, 38, 202–211.

Miyake et al., "The Novel Natural Product YM–26567–1 [(+)–trans–4–(3–dodecanoyl–2,3, 6–trihydroxyphenyl)–7–hydroxy2–(4–hydroxyphenyl) chroman]: A Competitive Inhibitor of Group II Phospholipase $A_2$", *J. Pharm. & Exp. Therapeutics,* 1992, 263, 1302–1307.

Noel et al., "Phospholipase $A_2$ Engineering. 3. Replacement of Lysine–56 by Neutral Residues Improves Catalytic Potency Significantly, Alters Substrate Specificity, and Clarifies the Mechanism of Interfacial Recognition", *J. Am. Chem. Soc.,* 1990, 112, 3704–3706.

Oinuma et al., "Synthesis and Biological Evaluation of Substituted Benzenesulfinamides as Novel Potent Membrane–Bound Phospholipase $A_2$ Inhibitors", *J. Med. Chem.,* 1991, 34, 2260–2267.

O'Sullivan, M.C. et al., "A One–Step Procedure for the Selective Trifluoroacetylation of Primary Amino Groups of Polyamines", *Tetrahedron Letts.,* 1995, 36, 3451–3452.

Pon, R.T., "Solid Phase Supports for Oligonucleotide Synthesis", *Methods in Molecular Biology, vol. 20, Protocols for Oligonucleotides and Analogs,* Agrawal, S. (ed.), Humana Press, Totowa, NJ, 1993, Chapter 19, 465–496.

Scott et al., "Interfacial Catalysis: The Mechanism of Phospholipase $A_2$", *Science,* 1990, 250, 1541–1546.

Tanaka et al., "A Novel Type of Phospholipase $A_2$ Inhibitor, Thielocin A1β, and Mechanism of Action", *J. Antibiotics,* 1992, 45, 1071–1078.

Washburn et al., "Suicide–inhibitory Bifunctionally Linked Substrates (Siblinks) as Phospholipase $A_2$ Inhibitors", *J. Biol. Chem.,* 1991, 266, 5042–5048.

Wery et al., "Structure of recombinant human rheumatoid arthritic synovial fluid phospholipase $A_2$ at 2.2 A resolution", *Nature,* 1991, 352, 79–82.

Yang et al., "Studies on the status of lysine residues in phospholipase $A_2$ from *Naja naja atra* (Taiwan cobra) snake venom", *Biochem. J.,* 1989, 262, 855–860.

Yuan et al., "Synthesis and Evaluation of Phospholipid Analogues as Inhibitors of Cobra Venom Phospholipase $A_2$", *J. Am. Chem. Soc.,* 1987, 109, 8071–8081.

NITROGENOUS MACROCYCLIC COMPOUNDS

CROSS REFERENCE TO RELATED APPLICATIONS

This application is 371 of PCT/US96/04215, filed Mar. 27, 1996, and a continuation-in-part of U.S. application Ser. No. 08/461,728, filed Jun. 5, 1995 which is a continuation-in-part of U.S. application Ser. No. 08/410,703, filed Mar. 27, 1995. The foregoing patent applications are assigned to the assignee of this application and are incorporated by reference herein.

FIELD OF THE INVENTION

This invention relates to macrocyclic compounds and libraries of these compounds. The macrocyclic compounds of the invention have a plurality of nitrogenous sites that are derivatized by reaction with active forms of reactant compounds. The reactant compounds, upon covalently binding to the macrocyclic nitrogenous substrates, introduce diversity into the macrocyclic compounds. The reactant compounds are selected to be compounds that have, aside from a group capable of reacting with a nitrogenous species, a further functional group thereon that gives each individual compound at least one property that renders it diverse as compared to the other reactant compounds. Hence the incoming reactant compound bearing a chemical functional moiety imparts diversity to the macrocyclic compound and, upon bonding with the macrocycle, its residue can be referred to as a pendant chemical functional group.

The addition of the chemical functional groups at the several nitrogenous sites on the macrocyclic compound yields a macrocyclic compound having a unique set of properties. These properties include the overall global shape, the conformational space, electron density, dipole moment and ability of the compound to interact with enzyme pockets and other binding sites and other similar properties. Combinatorialized libraries of the macrocycles are synthesized having various permutations and combinations of the several chemical functional groups at the nitrogenous sites. Such synthesis is effected at each of the nitrogenous sites by presenting each nitrogenous site with several of the reactant compounds such that combinatorial mixtures are obtained. The libraries are deconvoluted to yield unique macrocyclic compounds. Preferred macrocycles of the invention have cyclophane-like structures.

The chemical functional groups on the macrocyclic compounds of the invention provide for binding of the compounds to proteins, including enzymes, nucleic acids, lipids and other biological targets. In preferred embodiments, the compounds of the invention act as inhibitors of pathogens such as virus, mycobacterium, bacteria (gram negative and gram positive), protozoa and parasites; as inhibitors of ligand-receptor interactions such as PDGF (platelet derived growth factor), $LTB_4$ (leukotriene $B_4$), IL-6 and complement $C5_A$; as inhibitors of protein/protein interactions including transcription factors such as p50 (NFκB protein) and fos/jun; as inhibitors of enzymes such as phospholipase $A_2$; and for the inhibition of cell-based interactions including ICAM induction (using inducers such as IL1-β, TNF and LPS). In other preferred embodiments, the compounds of the invention are used as diagnostic reagents, including diagnostic reagents in the tests for each of the above noted systems, and as reagents in assays and as probes. In even further preferred embodiments, the compounds of the invention are used as metal chelators and contrast agent carriers. In even further preferred embodiments, the compounds of the invention are used as herbicides and insecticides.

BACKGROUND OF THE INVENTION

Traditional processes of drug discovery involve the screening of complex fermentation broths and plant extracts for a desired biological activity or the chemical synthesis of many new compounds for evaluation as potential drugs. The advantage of screening mixtures from biological sources is that a large number of compounds are screened simultaneously, in some cases leading to the discovery of novel and complex natural products with activity that could not have been predicted otherwise. The disadvantages are that many different samples must be screened and numerous purifications must be carried out to identify the active component, often present only in trace amounts. On the other hand, laboratory syntheses give unambiguous products, but the preparation of each new structure requires significant amounts of resources. Generally, the de novo design of active compounds based on the high resolution structures of enzymes has not been successful.

It is, thus, now widely appreciated that combinatorial libraries are useful per se and that such libraries and the compounds they comprise have great commercial importance. Indeed, a branch of chemistry has developed to exploit the many commercial aspects of combinatorial libraries.

In order to maximize the advantages of each classical approach, new strategies for combinatorial deconvolution have been developed independently by several groups. Selection techniques have been used with libraries of peptides (Geysen, H. M., Rodda, S. J., Mason, T. J., Tribbick, G. and Schoofs, P. G., *J. Immun. Meth.* 1987, 102, 259–274; Houghten, R. A., Pinilla, C., Blondelle, S. E., Appel, J. R., Dooley, C. T. and Cuervo, J. H., *Nature,* 1991, 354, 84–86; Owens, R. A., Gesellchen, P. D., Houchins, B. J. and DiMarchi, R. D., *Biochem. Biophys. Res. Commun.,* 1991, 181, 402–408; Doyle, M. V., PCT WO 94/28424; Brennan, T. M., PCT WO 94/27719); nucleic acids (Wyatt, J. R., et al., *Proc. Natl. Acad. Sci. USA,* 1994, 91, 1356–1360; Ecker, D. J., Vickers, T. A., Hanecak, R., Driver, V. and Anderson, K., *Nucleic Acids Res.,* 1993, 21, 1853–1856); nonpeptides and small molecules (Simon, R. J., et al., *Proc. Natl. Acad. Sci. USA,* 1992, 89, 9367–9371; Zuckermann, R. N., et al., *J. Amer. Chem. Soc.,* 1992, 114, 10646–10647; Bartlett, Santi, Simon, PCT WO91/19735; Ohlmeyer, M. H., et al., *Proc. Natl. Acad. Sci. USA ,* 1993, 90, 10922–10926; DeWitt, S. H., Kiely, J. S., Stankovic, C. J., Schroeder, M. C. Reynolds Cody, D. M. and Pavia, M. R., *Proc. Natl. Acad. Sci. USA,* 1993, 90, 6909–6913; Cody et al., U.S. Pat. No. 5,324,483; Houghten et al., PCT WO 94/26775; Ellman, U.S. Pat. No. 5,288,514; Still et al., PCT WO 94/08051; Kauffman et al., PCT WO 94/24314; Carell, T., Wintner, D. A., Bashir-Hashemi, A. and Rebek, J., *Angew. Chem . Int. Ed. Engel.,* 1994, 33, 2059–2061; Carell, T., Wintner, D. A. and Rebek, J., *Angew. Chem. Int. Ed. Engel.,* 1994, 33, 2061–2064; Lebl, et al., PCT WO 94/28028). We have developed certain nitrogen coupled chemistries that we utilized to prepare a class of compounds we refer to as "oligonucleosides." We have described these compounds in previous patent applications including published PCT applications WO 92/20822 (PCT US92/04294) and WO 94/22454 (PCT US94/03313). These chemistries included amine linkages, hydroxylamine linkages, hydrazino linkages and other nitrogen based linkages.

A review of the above references reveals that the most advanced of these techniques are those for selection of peptides and nucleic acids. Several groups are working on selection of heterocycles such as benzodiazepines. With the exception of Rebek et al., scant attention has been given to combinatorial discovery of other types of molecules. No combinatorial discovery approaches have been reported for non-linear (non-peptide, non-nucleic acid) macromolecules.

The majority of the techniques reported to date involve iterative synthesis and screening of increasingly simplified subsets of oligomers. Monomers or sub-monomers that have been utilized include amino acids, amino acid-like molecules, i.e. carbamate precursors, and nucleotides, both of which are bifunctional. Utilizing these techniques, libraries have been assayed for activity in either cell-based assays, or for binding and/or inhibition of purified protein targets.

A technique, called SURF™ (Synthetic Unrandomization of Randomized Fragments), involves the synthesis of subsets of oligomers containing a known residue at one fixed position and equimolar mixtures of residues at all other positions. For a library of oligomers four residues long containing three monomers (A, B, C), three subsets would be synthesized (NNAN, NNBN, NNCN, where N represents equal incorporation of each of the three monomers). Each subset is then screened in a functional assay and the best subset is identified (e.g. NNAN). A second set of libraries is synthesized and screened, each containing the fixed residue from the previous round, and a second fixed residue (e.g. ANAN, BNAN, CNAN). Through successive rounds of screening and synthesis, a unique sequence with activity in the functional assay can be identified. The SURF™ technique is described in Ecker, D. J., Vickers, T. A., Hanecak, R., Driver, V. & Anderson, K., *Nucleic Acids Res.,* 1993, 21, 1853–1856. The SURF™ method is further described in PCT patent application WO 93/04204, the entire disclosure of which is herein incorporated by reference.

The combinatorial chemical approach that has been most utilized to date, utilizes an oligomerization from a solid support using monomeric units and a defined connecting chemistry, i.e. a solid support monomer approach. This approach has been utilized in the synthesis of libraries of peptides, peptoids, carbamates and vinylogous peptides connected by amide or carbamate linkages or nucleic acids connected by phosphate linkages as exemplified by the citations in previous paragraphs above. A mixture of oligomers (pool or library) is obtained from the addition of a mixture of activated monomers during the coupling step or from the coupling of individual monomers with a portion of the support (bead splitting) followed by remixing of the support and subsequent splitting for the next coupling. In this monomeric approach, each monomeric unit would carry a tethered letter, i.e., a functional group for interaction with the target. Further coupling chemistry that allows for the insertion of a tethered letter at a chemically activated intermediate stage is referred to as the sub-monomer approach.

The diversity of the oligomeric pool is represented by the inherent physical properties of each monomer, the number of different monomers mixed at each coupling, the physical properties of the chemical bonds arising from the coupling chemistry (the backbone), the number of couplings (length of oligomer), and the interactions of the backbone and monomer chemistries. Taken together, these interactions provide a unique conformation for each individual molecule.

There remains a need in the art for molecules which have fixed preorganized geometry that matches that of targets such as proteins and enzymes, nucleic acids, lipids and other targets. The backbone of such molecules should be rigid with some flexibility, and such molecules should be easy to construct in solution or via automated synthesis on solid support.

Unsymmetrical N-substituted polyazamacrocycles are disclosed in Gu, K., et al., *Tetrahedron Lett.,* 1989, 30, 1323–1326.

Synthesis of diaza[7]-, [8]-, [9]-, [10]-(2,6) pyridinophanes are disclosed in Krakowiak, K., *Polish Journal of Chemistry,* 1986, 60, 277–281.

OBJECTS OF THE INVENTION

It is an object of the invention to provide macrocyclic compounds for diagnostic, research, and therapeutic use.

It is a further object of the invention to provide macrocyclic compounds that have a plurality of nitrogenous sites for introducing chemical functional groups into the macrocycle to provide "diversity" to the basic macrocycle.

It is yet another object of the invention to provide methods for preparing libraries of diversified macrocyclic compounds.

It is a still further object of the invention to provide libraries of combinatorialized macrocyclic compounds.

These and other objects will become apparent to persons of ordinary skill in the art from a review of the present specification and the appended claims.

SUMMARY OF THE INVENTION

The present invention provides novel cyclophane-like compounds and macrocyclic compounds comprising cyclic structures that are interrupted with at least one aromatic, alicyclic or heterocyclic ring system having two bridgehead atoms, each bridgehead atom being connected to at least one bridge containing at least two nitrogenous moieties bearing chemical functional groups.

In certain embodiments, each chemical functional group is, independently, of the structure:

where T is a single bond, a methylene group or a group having the structure

wherein:

$R^6$ is $=O$, $=S$, $=NR^3$;

$R^5$ and E, independently, are a single bond, $CH=CH$, $C\equiv C$, O, S, $NR^3$, $SO_2$, or $C_6$–$C_{14}$ aryl;

each $R^1$, $R^2$ and $R^3$ is, independently, H, alkyl or haloalkyl having 1 to about 10 carbon atoms; alkenyl having 2 to about 10 carbon atoms; alkynyl having 2 to about 10 carbon atoms; or aryl having 6 to about 14 carbon atoms;

m and n, independently, are zero to 5;

p is zero or 1;

q is 1 to about 10; and

L is, H, $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocyclic alkyl, or substituted $C_4$–$C_7$ carbocyclic alkyl, alkenyl or alkynyl carbocyclic, or substituted alkenyl or alkynyl carbocyclic, or $C_6$–$C_{14}$ aryl or substituted aryl where the substituent groups are selected from hydroxyl, amino, alkoxy, alcohol, benzyl, phenyl, nitro, thiol, thioalkoxy, halogen, alkyl, aryl, alkenyl, or alkynyl groups; an ether having 2 to 10 carbon atoms and 1 to 4 oxygen or sulfur atoms; a nitrogen, sulfur or oxygen containing heterocycle; a metal coordination group; a conjugate group; halogen;

hydroxyl (OH); thiol (SH); keto (C=O); carboxyl (COOH); amide (CONR$^1$); amidine (C(=NH)NR$^1$R$^2$); guanidine (NHC(=NH)NR$^1$R$^2$); glutamyl R$^3$OOCCH(NR$^1$R$^2$)(CH$_2$)$^2$C(=)—); nitrate (ONO$_2$); nitro (NO$_2$); nitrile (CN); trifluoromethyl (CF$_3$); trifluoromethoxy (OCF$_3$); O-alkyl; S-alkyl; NH-alkyl; N-dialkyl; O-aralkyl; S-aralkyl; NH-aralkyl; amino (NH$_2$); azido (N$_3$); hydrazino (NHNH$_2$); hydroxylamino (ONH$_2$); sulfoxide (SO); sulfone (SO$_2$); sulfide (S—); disulfide (S—S); silyl; a nucleosidic base; an amino acid side chain; a carbohydrate; a drug; or a group capable of hydrogen bonding.

In certain preferred embodiments of the present invention, compounds are provided of the structure:

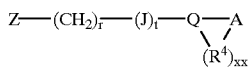

wherein:
xx is 0–4;
R$^4$ is a single bond connecting Q and A; or a group having the formula:

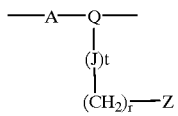

wherein each Z is, independently, H, hydroxyl, amino, thiol, acyl, protected hydroxyl, protected amino, protected thiol, protected acyl, or N—(T—L)$_2$;

each r is, independently, from 0 to about 8;
each J is, independently, N, O, S, or a heterocyclic ring system;
each t is, independently, 0 or 1;
L is H, C$_1$–C$_{10}$ alkyl or substituted alkyl, C$_2$–C$_{10}$ alkenyl or substituted alkenyl, C$_2$–C$_{10}$ alkynyl or substituted alkynyl, C$_4$–C$_7$ carbocyclic alkyl, alkenyl or alkynyl or substituted carbocyclic, or C$_6$–C$_{14}$ aryl or substituted aryl where the substituent groups are selected from hydroxyl, amino, alkoxy, alcohol, benzyl, phenyl, nitro, thiol, thioalkoxy, halogen, alkyl, aryl, alkenyl, or alkynyl groups; an ether having 2 to 10 carbon atoms and 1 to 4 oxygen or sulfur atoms; a nitrogen, sulfur or oxygen containing heterocycle; a metal coordination group; a conjugate group; halogen; hydroxyl (OH); thiol (SH); keto (C=O); carboxyl (COOH); amide (CONR$^1$); amidine (C(=NH)NR$^1$R$^2$); guanidine (NHC(=NH)NR$^1$R$^2$); glutamyl R$^3$OOCCH(NR$^1$R$^2$)(CH$_2$)$^2$C(=O)—); nitrate (ONO$_2$); nitro (NO$_2$); nitrile (CN); trifluoromethyl (CF$_3$); trifluoromethoxy (OCF$_3$); O-alkyl; S-alkyl; NH-alkyl; N-dialkyl; O-aralkyl; S-aralkyl; NH-aralkyl; amino (NH$_2$); azido (N$_3$); hydrazino (NHNH$_2$); hydroxylamino (ONH$_2$); sulfoxide (SO); sulfone (SO$_2$); sulfide (S—); disulfide (S—S); silyl; a nucleosidic base; an amino acid side chain; a carbohydrate; a drug; or a group capable of hydrogen bonding;

T is a single bond, a methylene group or a group having the structure:

each R$^6$ is, independently, =O, =S, =NR$^3$;
each R$^5$ and E is, independently, a single bond, CH=CH, C≡C, O, S, NR$^3$, or C$_6$–C$_{14}$ aryl;
each R$^1$, R$^2$ and R$^3$ is, independently, H, alkyl or haloalkyl having 1 to about 10 carbon atoms; alkenyl having 2 to about 10 carbon atoms; alkynyl having 2 to about 10 carbon atoms; or aryl having 6 to about 14 carbon atoms;

each m and n is, independently, zero to 5;
each p is, independently, zero or 1;
q is 1 to about 10;
each Q is an aromatic, alicyclic, or heterocyclic ring system;
each A is a group having the structure:

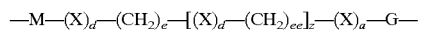

wherein
each X is, independently, —N(TL)—, —N(TL)—O—, —N(TL)—SO$_2$—, —N(TL)—SO—, —N(TL)S—, —N(TL)—C(O)—, —(TL)NH—C(O)—, —N(TL)—C(O)—O—, —N(TL)—(CO)—NR—, or —N(TL)—(CH$_2$)$_x$—O—;
M and G, independently, are —(CH$_2$)$_e$—, —N(TL)—(CH$_2$)$_e$—, —O—(CH$_2$)$_e$, —S—(CH$_2$)$_e$—, =N—, —N(R)—, O, S, —C(O)—;
each e is, independently, from 1 to about 5;
each ee is, independently, from 1 to about 5;
each d is, independently, from 0 to about 2;
z is from 1 to about 9;
a is from 0 to about 2; and
with the proviso that not more than three of the chemical functional groups, represented by —T—L, of each of the groups Q, are p-toluenesulfonyl or H and that at least two of the chemical functional groups are different.

Combinatorial synthetic strategies offer the potential to generate and screen libraries comprising extremely large numbers of compounds and identify individual molecules with desired properties. In certain embodiments of the invention, cyclophane-like compounds are provided that comprise part of a library of such compounds bearing varied chemical functional groups. Further, cyclophane-like compounds are provided bearing at least three different chemical functional groups thereon.

In accordance with some embodiments of the present invention, a library of compounds is provided comprising a plurality of macrocyclic molecules having an identical macrocyclic structure, a plurality of at least two different types of nitrogenous moieties and a plurality of chemical functional groups covalently bonded to the nitrogenous moieties.

In accordance with one embodiment of the present invention, a library of compounds is provided comprising a plurality of macrocyclic molecules having an identical macrocyclic structure, a plurality of nitrogenous moieties and a plurality of chemical functional groups covalently bonded to the nitrogenous moieties.

Methods of the present invention are useful for generating a library of macromolecules. These methods comprise selecting a macromolecule having at least one ring system, one bridge for each ring system connected to at least one bridgehead atom thereof, and having a plurality of nitrogenous moieties located within the macromolecule. These methods further comprise selection and reaction of a plurality of chemical functional group reactants for introduction of chemical functional groups on the nitrogenous moieties.

BRIEF DESCRIPTION OF THE DRAWINGS

The numerous objects and advantages of the present invention may be better understood by those skilled in the art by reference to the accompanying figures, in which.

DETAILED DESCRIPTION OF THE INVENTION

Figure 1:
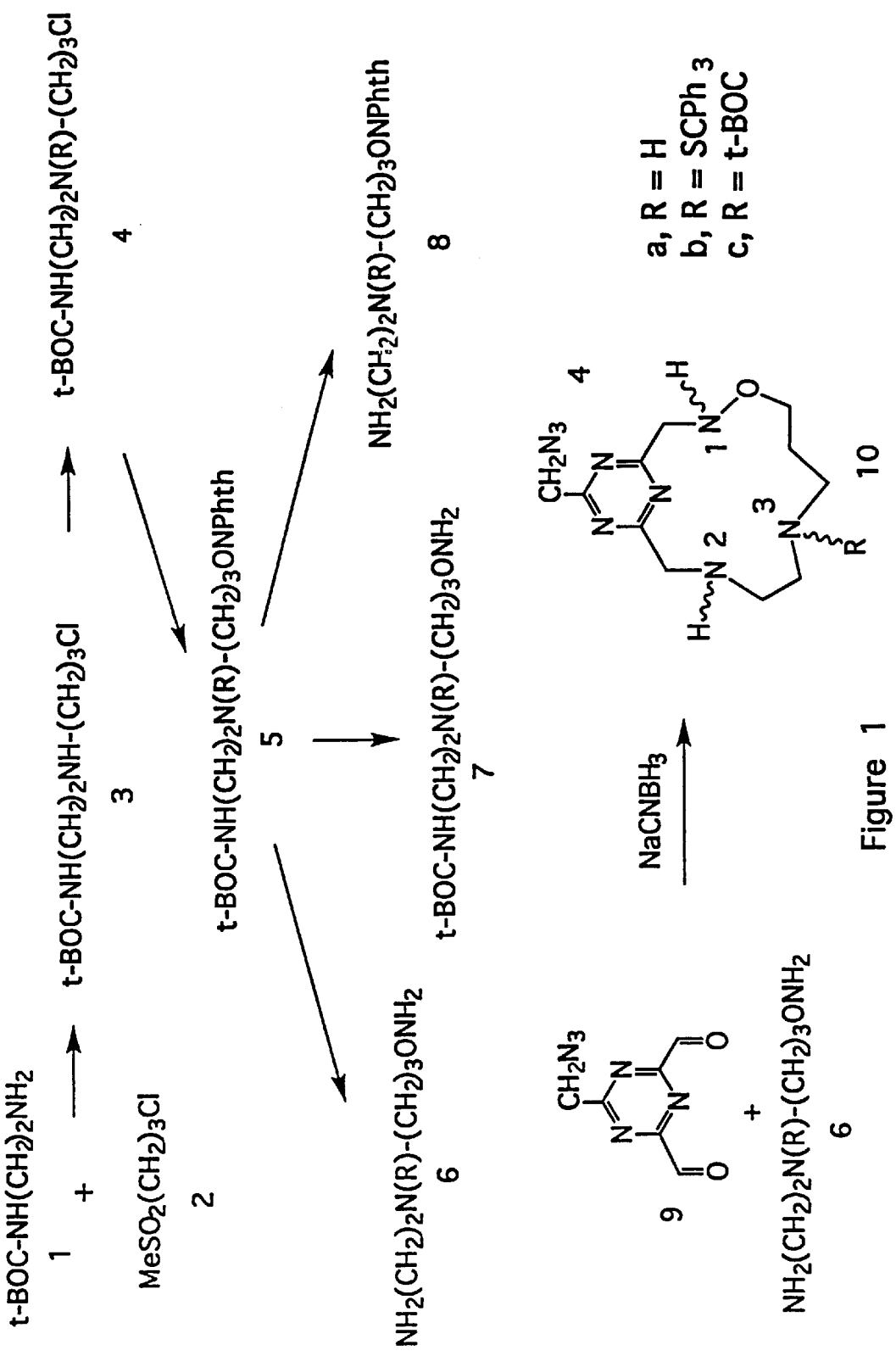
FIG. 1 is a synthetic scheme for the synthesis of macrocyclic compounds according to the invention.

Various natural, multi-ring, macrocyclic structures are known to have useful properties. Many of these are very complex compounds such as the vancomycin and amphotericin families of antibiotics. Vancomycin might also be classified as a cyclic peptide. Other cyclic peptides include phalloidin, obtained from the poisonous toadstool, *Amanita phalloides*. Further antibiotic macrocycles having more than one ring include rifamycin, rifamycin S, ansatrienin, napthomycin A and others. Also, multi-ring macrocycles, such a gloeosporon, are known to possess fungistatic properties. Other multi-ring macrocyclic compounds have shown antitumor activity including bouvardin, deoxybouvardin and certain macrocycles from the red algae *Phacelocaspus labillardieri* and bryostatin 8. Certain alkaloids, e.g. lunarine, are also multi-ring macrocycles. Many crown macrocycles, including aza-crown macrocycles include multi-ring structures such as dibenzoaza-crowns.

The "cyclophane" or "phane" nomenclature is useful for naming multi-ring macrocycles. A cyclophane is generally considered to include an aromatic nucleus (benzene or arene) and an aliphatic bridge. The bridge extends between two bridgehead atoms in the ring. The "phane" nomenclature can also be useful in describing multi-ring macrocyclic compounds having more than one ring system included in the macrocyclic ring. In this instance a macrocyclic compound comprises a number of rings or ring systems with bridges connecting the rings to form a cyclophane-like compound or macrocyclic compound. In such multi-ring compounds, at least one bridge would connect bridgehead atoms of two different ring systems. In naming cyclophane-like compounds, the generic heading "cyclophane" is replaced by the designation "phane," which denotes all bridged aromatics (including condensed and heteroaromatics such as naphthalene and pyridine). In cyclophane, the prefix "cyclo" thus stands for the benzene ring. A first subdivision of the "phanes" is into cyclophanes, heterophanes and heteraphanes. Heterophanes contain hetero atoms in the aromatic ring, while heteraphanes include hetero atoms in the bridge. The length of the bridges in the phane (the number of atoms between two aromatic points, i.e. bridgehead atoms) is placed in order of decreasing length within square brackets preceding the name with the syllable "phane" serving as the suffix. The position of the bridges can be designated by ortho, meta, para or with numbers in parentheses that are placed after the square brackets. In addition to aromatic and heterocyclic rings, alicyclic rings can also be included in the "phanes." Such phanes are named as aliphanes, e.g. hexanophane, adamantanophanes, cubanophane or steroidophanes.

Cyclophane chemistry is described in *Cyclophane Chemistry, Synthesis, Structures and Reactions,* Fritz Vogtle, John Wiley & Sons, New York, N.Y., 1993. Macrocyclic chemistry is described in *Macrocyclic Chemistry, Aspects of Organic and Inorganic Supramolecular Chemistry,* B. Dietrich, P. Viout and J.-M. Lehn, VCH, New York, N.Y., 1993. Aza-crown chemistry is described in *Aza-Crown Macrocycles,* J. S. Bradshaw, K. E. Krakowiak and R. M. Izatt, John Wiley & Sons, New York, N.Y., 1993. The contents of each of these volumes is herein incorporated by reference.

Compounds of the invention are macrocyclic compounds that contain nitrogenous moieties therein that are derivatized with "chemical functional groups." Each of the macrocyclic compounds includes a plurality of such nitrogenous moieties (or nitrogenous sites). Each nitrogenous moiety can be derivatized with one of a variety of chemical functional groups. Libraries of such compounds having various permutations and combinations of chemical functional groups and nitrogenous sites can be prepared and used in standard biological assays such as standard antibiotic assays.

As used in this specification, a "chemical functional" group is one that, when attached to a parent molecule, imparts to that molecule a particular and unique characteristic. It contributes diversity to the parent molecule by rendering the parent molecule different in some way from what it was before attachment of the group. Several chemical functional groups can be attached to a particular molecule and when considered together, the sum total of their properties will impart global diversity characteristics to the parent molecule. Each set of combinations of chemical functional groups on a particular molecule will modify the parent such that the parent molecule having each particular combinations of groups will be different from the parent molecule having any of the other combinations of groups. When all of the combinations of the groups on the parent are considered, a library of compounds will be formed that include all of the possible combinations of groups.

The macrocyclic compounds of the invention include at least one ring structure that is interrupted by one or more further rings. Preferred macrocyclic compounds of the invention have ring structures larger than 10 atoms that include one or two aromatic, heterocyclic, or aliphatic ring systems, and further include a plurality of nitrogenous sites that can be substitued with chemical functional groups. Preferably, all or substantially all of the nitrogenous sites are substituted with chemical functional groups. More preferred macrocyclic compounds of the invention include one or two heterocyclic rings, and a plurality of nitrogenous sites that can be substituted with chemical functional groups. Preferably, all or substantially all of the nitrogenous sites are substituted with chemical functional groups. The heterocyclic rings can have pendant groups that include nitrogenous sites that are preferably substituted with chemical functional groups.

Macrocyclic compounds of the invention can be synthesized with both the position and the choice of the chemical functional groups predetermined, or allowed to be selected by combinatorial selection. In the context of this invention, "combinatorial" does not mean arbitrary, haphazard or indiscriminate. In the context of this invention, "combinatorial" is construed to mean that within the totality of the population of macrocyclic molecules that can be formed using a particular set of chemical functional groups and a particular location of nitrogenous moiety sites within the macrocyclic molecule, there will be sub-populations of each of the possible species. Thus, each of the different combinations of a) choice of chemical functional group and b) positioning of the chemical functional groups will be represented.

"Combinatorial" is distinct from "random." To illustrate the distinction, if all or nearly all possible combinations are present in the total molecular population, then it is a combinatorial population of molecules. If, however, only one or a small number of molecules from that total population is selected, then the selected molecule or molecules might be randomly selected if it is picked at whim or will from the total population. When the totality of the population is considered, all species are present and it is not a random population. If a systematic selection was made until the totality of the population was exhausted, then all of the species would eventually be selected, however, the order of selection might be random. Thus, in certain preferred embodiments, a pre-ordered selection and/or location of chemical functional groups will be present. In further preferred embodiments, a combinatorialized population of all possible combinations and ordering of the chemical functional groups is present. In even further preferred embodiments, the sequence is modulated between fixed and combinatorial. This is especially useful, as for example, in certain deconvolution strategies.

"Deconvolution" is construed to mean taking the totality of a population and systematically working through that population to establish the identity of a particular member, selected members, or all members of the population. In deconvoluting a combinatorial library of compounds, systematic selection is practiced until an individual compound or a group of individual compounds having a particular characteristic, as for instance being an active species in a specific functional assay, is identified.

The macrocyclic compounds of the invention are prepared by modification of nitrogenous moieties by reaction with reactant compounds for introduction or addition of chemical functional groups on the nitrogenous sites. The reactant compounds are compounds that have both a functionalized site thereon that is capable of reaction with a nitrogen atom of a nitrogenous moiety as well as a further functional group thereon that serves to impart diversity to the reactant compound and to any molecule to which it might be covalently bonded. Reaction between the reactant compounds and the macrocycle connects the reactant compound to the nitrogen atom at a nitrogenous site on the macrocycle. The nitrogenous moieties can be one of various moieties that include a nitrogen atom as an integral part of the moiety. The chemical functional group is covalently bonded to the nitrogen atom of the nitrogenous moiety to introduce a point of functionality or point of diversity at that particular nitrogen atom. Alternatively a particular nitrogenous moiety might include a "null" in place of the functional group, i.e. absence of a functional group. This is accomplished by having a hydrogen atom covalently bonded to the nitrogen atom or by having a double bond between the nitrogen atom and an adjacent atom, e.g. as an oxime or imine. Certain of the nitrogenous moieties are better for imparting a certain structure to the bridge as opposed to serving as a platform for adding chemical functional groups thereto. Included in this group are carbamates, ureas, sulfonamides, sulfinamides and sulfanamides. When the presence of these nitrogenous species is desired for structural purposes as opposed to locations for chemical functional group placement, they can be left in a "null" state.

In one embodiment the macrocyclic compounds of the invention include a ring system and a bridge that connects between "bridgehead atoms" located in the ring system. Such compounds are either cyclophanes or are cyclophane-like structures. The ring system can be an aromatic ring system, a heterocyclic ring system, an alicyclic ring system, or a mixed ring system such as an araaliphatic (i.e., mixed aromatic-alicyclic, such as benzyl) ring system. The bridge includes at least two of the nitrogenous moieties therein, preferably, three of such sites.

In a further embodiment of the invention the macrocyclic compounds include two or more ring systems and two or more bridges that connect between "bridgehead atoms" located in the ring systems. In these macrocyclic compounds the bridges connect the ring systems to form a continuous cyclic compound. Such compounds are cyclophane-like structures. The ring systems can be aromatic ring systems, heterocyclic ring systems, alicyclic ring systems, or mixed ring systems such as araaliphatic ring systems. Each bridge preferably includes at least two of the nitrogenous moieties therein, more preferably, three of such moieties.

In some preferred embodiments of the invention, the bridges are non-symmetrical. This can be achieved either by varying the number of carbon atoms or heteroatoms located in the bridges between the nitrogenous moieties, or by differing the functional groups bound to nitrogenous moieties within the bridges, or by varying both of these parameters. Thus, in certain preferred macrocyclic compounds of the invention, at least two of the nitrogenous moieties in a bridge are different from one another, e.g. a bridge which includes both an amine and a hydroxylamine nitrogenous moiety. The nitrogen atom of at least some of the nitrogenous moieties is included in bridge backbones i.e., the nitrogen atom of at least some of the nitrogenous moieties form part of the bridge. Thus, if an amine is selected as a nitrogenous species in a bridge, it is present as a secondary amine or imine before addition of a chemical functional group. Upon covalent bonding of the chemical functional group to it, it then exists as a tertiary amine, which has a single bond to one side of the bridge, a single bond to the other of the bridge, and a single bond to the chemical functional group.

Further nitrogenous moieties can reside in a ring system or can be appended to a ring system on a pendant group that is independent of the bridge. Nitrogenous moieties pendant to a ring system, preferably, are located distal to the attachment of the pendant group to the ring system. Thus utilizing an alkane group to serve as a pendant extender or tether, the nitrogenous moiety would be located at or near one end of such alkane while the alkane in turn would be covalently bonded to the ring system at its other end. Other pendant extender groups useful for the attachment of nitrogenous moieties to a ring include hetero atoms in combination with alkyl groups (as shown in, for example, Examples 98 and 99) and heterocyclic rings (as shown in, for example, Examples 120–129).

Nitrogenous moieties residing in the ring system include nitrogen atoms of heterocyclic rings that are members of the ring. In certain preferred embodiments of the invention, one or more of the ring nitrogens in an aromatic nitrogen heterocycle, e.g. pyridine, acridine or pyrimidine, or in a non-aromatic nitrogen heterocycle, e.g. piperidine, can be derivatized with chemical functional groups, while in other preferred embodiments, no chemical functional groups are included on the ring nitrogens of the heterocycle.

In some preferred embodiments of compounds of the invention there will be from 2 to about 10 such nitrogenous moieties. In still other preferred compounds of the invention, there will be from 2 to 6 such nitrogenous moieties. A more preferred range is from 2 to 4 of such nitrogenous moieties. An even more preferred range is from 3 to 4 nitrogenous moieties.

Preferred nitrogenous moieties are, in either orientation, amine [—N(X)H—], hydroxylamine [—O—N(X)—], hydrazine [—NH—N(X)—], amides [—C(O)—N(X)—], hydrazides [—C(O)—NH—N(X)—] carbamates [—O—C(O)—N(X)—], ureas [—NH—C(O)—N(X)—], sulfonamide [—SO$_2$—N(X)—], sulfinamide [—SO—N(X)—] and sulfanamide [—S—N(X)—] moieties where the (X) group of the structures indicate a chemical functional group that is covalently bonded to the nitrogenous moiety.

Illustrative carbon rings for the macrocyclic compound of the inventions include, but are not limited to, benzene, cyclopentane, cyclohexane, cycloheptane, cyclooctane, cyclononane, cyclodecane, transcyclooctane, cyclooctyne, cyclohepta-1,3-diene, [10]annulene (cyclodecapentaene), and [9]annulene (cyclonona-1,3,5,7-tetraene).

Illustrative monocyclic nitrogen heterocycles include, but are not limited to, cyanuric acid, aziridine, azetine 1,3-diazetidine, cyclopentaazane, pyrrole, pyrazole, imidazole, 1,2,3-triazole, 1,2,4-triazole, 1,2,3-triazine, 1,2,4-triazine, cyanuric acid, pyridine, pyridazine, piperidine, pyrrolidine, pyrimidine, pyrazine, piperazine, pyridazine, s-triazine, azepine, 1,2,4-triazepine, and azocine. Illustrative oxygen heterocycles include, but are not limited to, furan, 1,4-pyran, 1,2-dioxane, 1,3-dioxane, oxepin, 1,3,5,7-tetraoxocane and 1,4,8,11-tetraoxacyclotetradecane. Illustrative sulfur heterocycles include, but are not limited to thiophene, thiepine, 1,4-thiazepine. Illustrative mixed heterocycles include, but are not limited to, 1,2,3-oxathiole, isoxazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,4-oxazine, 1,3,2-oxazine, 1,3,6-oxazine, 1,2,6-oxazine, 1,4-oxazine o-isoxazine, p-isoxazine, 1,2,5-oxathiazine, 1,2,6-oxthazine, 1,4,2-oxadiazine, 1,3,5,2-oxadiazine, 1,4-thiazepine and morpholine.

For the purposes of this invention a ring system is defined to include two or more single rings that join together to form an extended or condensed ring. Such ring systems include extended aromatic systems, alicyclic systems, araalicyclic systems, bicyclic systems and even spiro systems. Examples include aromatic, alicyclic and mixed aromatic-alicyclic (araalicyclic) multiple ring systems, spiro systems, bicyclic systems, non-aromatic multiple ring systems such as adamantane, decalin, steroids and terpenes, including sesquiterpenes, diterpenes, triterpenes and tetraterpenes, and multiple ring heterocyclic systems. Illustrative carbon ring systems include, but are not limited to, naphthalene, tetrahydronaphthalene (tetralin), anthracene, phenanthrene, fluorene, pyrene, coronene, azulene, cluorene, benzonaphthene, benzo[8]annulene, pentalene, heptalene, octalene, indene, isoindene biphenyl, biphenylene and triphenylene condensed rings; spiropentane, spiro[2.4]heptane, spiro[4.5]decane, spiro[3.4]octane, dispiro[5.1.7.2] heptadecane spiro systems; bornane, norbornane, camphor, bicyclo[2.2.1]heptane, bicyclo[3.2.1]octane, 7-methylbicyclo[2.2.1]heptane and trans and cis-bicyclo [4.4.0]decane (trans and cis-decalin) bicyclic systems; carotenes, delta-3-carene, alpha-pinene, camphor, ascaridole, azulene, cadinene, beta-selinene, ambrein, beta-amyrin and lupeol terpenes; cholesterol, lanosterol, coprostanol, stigmasterol, ergosterol, calciferol, cholic acid, deoxycholic acid, estrone, estradiol, estratriol, progesterone, stilbestrol, testosterone, androsterone, deoxycorticosterone, cortisone and 17-hydroxycorticosterone steroids.

Illustrative multiple ring heterocyclic systems include, but are not limited to, carbazole, acridine, xanthene, purine, 1,4-benzisoxazine, 1,2-benzisoxazine, 3,1,4-benzoxazine, 2,3,1-benzoxazine, 1,4,2-benzoxazine, 1,3,2-benzoxazine, pyrido[4,3-b]pyridine, pyrido[3,2-b]pyridine, pyrido[3,4-b] pyridine, naphthyridine, quinazoline, cinnoline, isoquinoline, quinoline, 1,2-benzoyran, anthranil, benzoxazole, indoxazine, indolazine, pyrano[3,4-b]pyrrole, 1,5-pyrindine, 2-isobenzole, indolenine, indole, isthionaphthene, thionaphthene, isobenzofuran, benzofuran, and 2,2'-bipyridine.

Preferred rings and ring systems include aziridine, azetine, pyridine, 1,3,5-triazine, a-triazine (or as-triazine,) cyanuric acid, pyrrole, pyrazole, 1,2,3-triazole, imidazole, pyrimidine, purine, piperidine, pyrazole, pyrrolidine, piperazine, pyrazine, pyridazine, morpholine, oxazole, isoxazole, thiazole, isothiazole, furan, pyran, thiophene, benzene, naphthalene, anthracene, cyclohexane, cyclopentane and adamantane.

Within a bridge portion of the macrocyclic compounds of the invention, the nitrogenous moieties are connected by "spacer" moieties. Thus, each bridge can be viewed as including spacer moieties that connect between adjacent nitrogenous moieties. Together, the spacer moieties and the nitrogenous moieties are covalently bonded to form the backbone of the bridge. The spacer moieties are, in essence, bifunctional in nature and alternate with the nitrogenous moieties to form a bridge having a plurality of diversity groups projecting therefrom. Preferred spacer groups include [CH$_2$]$_x$ where x is 1–5. Other preferred spacers include such methylene chains interrupted by one or more oxygen or sulfur atoms to form ethers and thioether spacers. Still further spacers include alicyclic and aromatic rings that are bifunctional and thus can be inserted into and connected with the remainder of the backbone of the bridge.

The nitrogen atoms of the nitrogenous moieties within the bridge, besides being linked together by the spacer groups, serve also as the primary site for connecting chemical functional groups that impart "diversity" properties to the compounds of the invention. By varying these chemical functional groups, diversity is incorporated into the compounds of the invention. Except when they are located on the ends of pendant groups on the ring system, or when they carry a "null" group thereon, the nitrogen atoms of the nitrogenous moieties are trivalent in nature, i.e. they are connected to at least two atoms within the bridge (one on either side) and to one chemical functional group that contributes diversity to the molecules.

The chemical functional groups appended to the nitrogenous moieties of the compounds of the invention can be of various structures that impart particular interactive properties to the macrocyclic compounds. These chemical functional groups can effect interactions of at least the following types: hydrogen-bond donors and acceptors, ionic, polar, hydrophobic, aromatic, electron donors and acceptors, pi bond stacking or metal binding. As a result of such interactions, the macrocyclic compounds of the inventions have unique properties affecting the overall global shape, the conformational space, electron density, dipole moment and ability of the compound to interact with enzyme pockets and other binding sites and other similar properties. While we do not wish to be bound by theory, placement of the chemical functional groups on the macrocycle platform "geometrically constrains" the molecules for better binding characteristics with target molecules.

The chemical functional groups can also be referred to as functional groups or as "letters." The use of such terminology reflects the fact that the different functional groups on the compounds of the invention are positioned in sequences (either predetermined or by random selection) much like letters of the alphabet, hence the term "letter." These letters can be "reactive" or "non-reactive." By "reactive," it is meant that they will interact with a target molecule in some manner (that need not but can be predefined). By "non-reactive," it is meant that they are not designed to primarily interact with a target molecule, and in fact while they may interact with the target molecule, the primary purpose of the non-reactive moieties are to impart other properties to the molecule such as, but not necessarily limited to, effecting up-take, distribution, metabolism or identification.

A first preferred group of chemical functional groups according to the invention include H, $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocyclic alkyl, alkenyl or alkynyl or substituted carbocyclic, or $C_6$–$C_{14}$ aryl or substituted aryl where the substituent groups are selected from hydroxyl, amino, alkoxy, alcohol, benzyl, phenyl, nitro, thiol, thioalkoxy, halogen, alkyl, aryl, alkenyl, or alkynyl groups; an ether having 2 to 10 carbon atoms and 1 to 4 oxygen or sulfur atoms; a nitrogen, sulfur or oxygen containing heterocycle; a metal coordination group; a conjugate group; halogen; hydroxyl (OH); thiol (SH); keto (C=O); carboxyl (COOH); amide (CONR$^1$); amidine (C(=NH$^1$)NR$^2$R$^3$); guanidine (NHC(=NH)NR$^1$R$^2$); glutamyl R$^3$OOCCH(NR$^1$R$^2$) (CH$_2$)$^2$C(=O)—); nitrate (ONO$_2$); nitro (NO$_2$); nitrile (CN); trifluoromethyl (CF$_3$); trifluoromethoxy (OCF$_3$); O-alkyl; S-alkyl; NH-alkyl; N-dialkyl; O-aralkyl; S-aralkyl; NH-aralkyl; amino (NH$_2$); azido (N$_3$); hydrazino (NHNH$_2$); hydroxylamino (ONH$_2$); sulfoxide (SO); sulfone (SO$_2$); sulfide (S—); disulfide (S—S); silyl; a nucleosidic base; an amino acid side chain; a carbohydrate; a drug; or group capable of hydrogen bonding.

In the context of this invention, a heterocyclic ring system means a cyclic compound containing at least one hetero atom such as N, O, or S. Heterocyclic compounds of the invention may be saturated, unsaturated or partially unsaturated.

Heterocycles, including nitrogen heterocycles, suitable for use as functional groups include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, and carbazole groups. Imidazole groups are especially preferred.

Purines and pyrimidines suitable for use as functional groups include adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering,* pages 858–859, Kroschwitz, J. I., ed. John Wiley & Sons, 1990, and those disclosed by Englisch et al., *Angewandte Chemie, International Edition* 1991, 30, 613.

In the context of this specification, alkyl (generally $C_1$–$C_{20}$), alkenyl (generally $C_2$–$C_{20}$), and alkynyl (generally $C_2$–$C_{20}$) groups include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2,4-diethylbutyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups containing a pi bond, cyclohexane, cyclopentane, adamantane as well as other alicyclic groups, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups.

Further, in the context of this invention, a straight chain compound means an open chain compound, such as an aliphatic compound, including alkyl, alkenyl, or alkynyl compounds; lower alkyl, alkenyl, or alkynyl as used herein include but are not limited to hydrocarbyl compounds from about 1 to about 6 carbon atoms. A branched compound, as used herein, comprises a straight chain compound, such as an alkyl, alkenyl, alkynyl compound, which has further straight or branched chains attached to the carbon atoms of the straight chain. A cyclic compound, as used herein, refers to closed chain compounds, i.e. a ring of carbon atoms, such as an alicyclic or aromatic compound. The straight, branched, or cyclic compounds may be internally interrupted, as in alkoxy or heterocyclic compounds. In the context of this invention, internally interrupted means that the carbon chains may be interrupted with heteroatoms such as O, N, or S. However, if desired, the carbon chain may have no heteroatoms.

Further in the context of this specification aryl groups (generally $C_6$–$C_{20}$) include but are not limited to substituted and unsubstituted aromatic hydrocarbyl groups. Aralkyl groups (generally $C_7$–$C_{20}$) include but are not limited to groups having both aryl and alkyl functionalities, such as benzyl and xylyl groups. Preferred aryl and aralkyl groups include, but are not, limited to, phenyl, benzyl, xylyl, naphthyl, tolyl, pyrenyl, anthracyl, azulyl, phenethyl, cinnamyl, benzhydryl, and mesityl. These can be substituted or unsubstituted. It is particularly preferred that if substituted, the substitution be meta to the point of attachment of the substitution aryl or aralkyl compound to the nitrogenous moieties or to tethers connecting to the nitrogenous moieties since such meta substitution isolates electronic effects of the substituent from the reactive functionality used to attach the aromatic moiety to the nitrogenous moiety or a tether.

The aliphatic and aromatic groups as noted above may be substituted or unsubstituted. In the context of this invention, substituted or unsubstituted, means that the compounds may have any one of a variety of substituents, in replacement, for example, of one or more hydrogen atoms in the compound, or may have no substituents. Typical substituents for substitution include, but are not limited to, hydroxyl, alkoxy, alcohol, benzyl, phenyl, nitro, thiol, thioalkoxy, halogen, or alkyl, aryl, alkenyl, or alkynyl groups.

Metal coordination groups according to the invention include, but are not limited to, carbonyl moieties, hyroxyl moieties, amine moieties, acid moieties and other more complex moieties such as hydroxamic acids, catecholamide, acetylacetone, 2,2'-bipyridine, 1,10-phenanthroline, diacetic acid, pyridine-2-carboxamide, isoalkyldiamine, thiocarbamate, oxalate, glycyl, histidyl and terpyridyl. Other metal coordination groups are also known (Mellor, D. P., *Chemistry of Chelation and Chelating Agents in International Encyclopedia of Pharmacology and Therapeutics*, Section 70, The Chelation of Heavy Metals, Levine, W. G. Ed., Pergamon Press, Elmford, N.Y., 1979).

Non-reactive functionalities used as chemical functional groups, such as groups that enhance pharmacodynamic properties, include groups that improve uptake and enhance resistance to enzymatic or chemical degradation. Non-reactive functionalities may also enhance pharmacokinetic properties. In the context of this invention, such groups improve uptake, distribution, metabolism or excretion. Non-reactive functionalities include, but are not limited to, alkyl chains, polyamines, ethylene glycols, steroids, polyamides, aminoalkyl chains, amphipathic moieties, and conjugate groups attached to any of the nitrogenous sites for attachment, as described above.

Conjugate groups of the invention include intercalators, reporter molecules, polyamines, polyamides, poly ethers including polyethylene glycols, and other moieties known in the art for enhancing the pharmacodynamic properties or the pharmacokinetic properties. Typical conjugate groups include PEG groups, cholesterols, phospholipids, biotin, phenanthroline, phenazine, phenanthridine, anthraquinone, acridine, fluoresceins, rhodamines, coumarins, and dyes.

A number of chemical functional groups can be introduced into compounds of the invention in a blocked form and subsequently deblocked to form a final, desired compound. In general, a blocking group renders a chemical functionality of a molecule inert to specific reaction conditions and can later be removed from such functionality in a molecule without substantially damaging the remainder of the molecule (Green and Wuts, Protective Groups in Organic Synthesis, 2d edition, John Wiley & Sons, New York, 1991). For example, amino groups can be blocked as phthalimido groups, as 9-fluorenylmethoxycarbonyl (FMOC) groups, and with triphenylmethylsulfenyl, t-BOC or benzyl groups. Carboxyl groups can be protected as acetyl groups. Representative hydroxyl protecting groups are described by Beaucage et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl) xanthine-9-yl (MOX). Chemical functional groups can also be "blocked" by including them in a precursor form. Thus, an azido group can be used considered as a "blocked" form of an amine since the azido group is easily converted to the amine.

Nitrogenous moieties can be incorporated in macrocyclic compounds of the invention in a blocked form to facilitate manipulation of chemical functional groups to particular sites within a given macrocyclic compound (FIGS. 1–5). Blocking and then selectively deblocking and functionalizing positions within macrocyclic compounds is useful for deconvolution of a library to elucidate the structure of an active compound.

Solid supports according to the invention include controlled pore glass (CPG), oxalyl-controlled pore glass (Alul et al., *Nucleic Acids Research* 1991, 19, 1527), TentaGel Support, which is an aminopolyethyleneglycol derivatized support (Wright et al., *Tetrahedron Letters* 1993, 34, 3373) or Poros which is a copolymer of polystyrene/divinylbenzene.

A further advantage of this invention is the ability to synthesize macrocyclic compounds that, in addition to or in place of variability in the sequences of the diversity groups, have an asymmetric sequence of spacer units. Stated otherwise, the spacer units can also vary within the macrocyclic structure. This is easily accomplished by using different compounds that eventually become incorporated as spacer units.

One preferred method of synthesizing the compounds of the invention is via solution phase synthesis. A further preferred method of synthesizing the compounds of the invention is via solid phase synthesis.

The chemical functional groups, i.e. groups that give individual characteristics to individual molecules, are attached to their respective monomeric units via the nitrogen atoms of the nitrogenous moieties. These chemical functional groups thus provide diverse properties or diversity to the resulting macrocyclic compounds. Such diversity properties include hydrogen-bond donors and acceptors, ionic moieties, polar moieties, hydrophobic moieties, aromatic centers, electron-donors and acceptors, pi bond stacking and metal binding. Together, the properties of the individual repeating units contribute to the uniqueness of the macrocycles in which they are found. Thus, a library of such macrocycles would have a myriad of properties, i.e. diversity. Collectively, the properties of the chemical functional groups on any one macrocycle contribute to the uniqueness of that macrocycle and impart certain characteristics thereto for interaction with proteins, lipids, or nucleic acids, or for cellular or enzymatic interactions with a target molecule. The macrocycle may also possess herbicidal or insecticidal properties.

As noted above, the macrocyclic compounds of the invention can be prepared having either preselected sequences or sequences determined via combinatorialization strategies. One useful combinatorial strategy is a "fix last" strategy noted in certain of the examples below. A further useful combinatorial strategy is the above-noted SURF™ strategy, which is disclosed and claimed in U.S. patent application Ser. No. 749,000, filed Aug. 23, 1991, and PCT Application US92/07121, filed Aug. 21, 1992, both of which are commonly assigned with this application. The entire disclosure of these applications are herein incorporated by reference.

Illustrative of the SURF™ strategy is a 2'-O-methyl oligonucleotide library (Ecker et. al., ibid.) shown in Table I below. Table I describes the selection of a 2'-O-methyl oligonucleotide for binding to an RNA hairpin. The $K_D$s, i.e. the binding constants, were determined by gel shift. "X" is used to indicate the position being varied and underlining is used to indicate positions that become fixed during successive iterations of the SURF™ strategy.

TABLE I

| Subsets | $K_D$ (mM) | | | |
|---|---|---|---|---|
| | X = A | X = C | X = G | X = T |
| Round 1 NNNNXNNNN | 22 | <u>10</u> | >100 | >100 |
| Round 2 NNNN<u>C</u>NXNN | >10 | <u>4</u> | >10 | >10 |
| Round 3 NNXN<u>C</u>N<u>C</u>NN | >10 | <u>0.5</u> | >10 | >10 |
| Round 4 NN<u>C</u>XN<u>C</u>N<u>C</u>NN | >10 | <u>0.15</u> | >10 | >10 |
| Round 5 NN<u>CCC</u>X<u>C</u>NN | <u>0.08</u> | >1 | 0.4 | >1 |
| Round 6 NN<u>CCC</u>A<u>C</u>XN | <u>0.05</u> | >0.5 | 0.08 | >0.5 |
| Round 7 NX<u>CCC</u>A<u>C</u>AN | >0.1 | >0.1 | <u>0.03</u> | >0.1 |
| Round 8 N<u>GCCC</u>A<u>C</u>AX | 0.05 | <u>0.02</u> | 0.05 | 0.04 |
| Round 9 X<u>GCCC</u>A<u>C</u>AC | 0.03 | 0.05 | 0.02 | <u>0.01</u> |

This SURF™ strategy has not been previously used for libraries except those that employ naturally-occurring nucleotide monomer units, as phosphodiesters or phosphorothioates. Other combinatorial strategies have been previously used only for libraries that employ amino acids as monomeric units.

One advantage of the present invention is that the simple design of a macrocyclic platform having multiple sites for diversity enables combining rational drug design with screening mechanisms for thousands of compounds. This is achieved by using the compounds of the invention in combinatorial techniques such as the SURF™ strategy or the "fix last" strategy described in this specification.

The macrocyclic compounds of the invention can be used in diagnostics, therapeutics and as research reagents and kits. They can be used in pharmaceutical compositions by including a suitable pharmaceutically acceptable diluent or carrier. In preferred embodiments, the compounds of the invention act as inhibitors of enzymes such as phospholipase $A_2$; as inhibitors of pathogens such as virus, mycobacterium, bacteria (gram negative and gram positive), protozoa and parasites; as inhibitors of ligand-receptor interactions such as PDGF (platelet derived growth factor), $LTB_4$ (leukotriene $B_4$), IL-6 and complement $C5_A$; as inhibitors of protein/protein interactions including transcription factors such as p50 (NFκB protein) and fos/jun; for the inhibition of cell-based interactions including ICAM induction (using inducers such as IL1-β, TNF and LPS) and as herbicides and insecticides. In other preferred embodiments, the compounds of the invention are used as diagnostic reagents for each of the above noted biological entities, and as reagents in assays and as probes. In other preferred embodiments, the compounds of the invention are used to chelate heavy metals and as imaging agents.

The compounds of the invention generally are prepared by coupling preselected bifunctional synthons under conditions effective to form the compounds. In certain embodiments, compounds of the invention are prepared by intermolecular reductive coupling. In other embodiments, compounds of the invention can be prepared by intermolecular radical addition reactions. In further embodiments, compounds can be prepared by nucleophilic displacement. In each of these embodiments, nitrogen atoms in the resulting linkage can be further functionalized. For example, the nitrogen atoms of the nitrogenous moieties can be reacted with a group having structure RL—T—L, thereby displacing the RL leaving group and forming a covalent —N—T—L linkage where T—L represents a chemical functional group or a tethered chemical functional group.

Amino nitrogenous compounds, if not directly available, can be synthesized by treating the corresponding hydroxyl-terminated compound with $Ph_3P$, $CBr_4$ and $LiN_3$ according to the procedure of Hata et al. (*J. Chem. Soc. Perkin* 1 1980, 306) to furnish a terminal azide. Reduction of the azido group with tributyltin hydride provides the desired amino functionality.

Hydroxylamino nitrogenous groups can be prepared by treating the corresponding hydroxyl compound with N-hydroxy-phthalimide, triphenylphosphine and diethylazodicarboxylate under Mitsunobu conditions to provide an O-phthalimido derivative. The free hydroxylamino compound can be generated in quantitative yield by hydrazinolysis of the O-phthalimido derivative.

Hydrazino nitrogenous compounds can be prepared by treating hydroxyl-terminated compounds with tosyl chloride in pyridine to give an O-tosylate derivative. Treatment of benzylcabazide with O-tosylate will furnish a benzylcarbazide derivative, which on hydrogenation provides the free hydrazino moiety for reductive coupling.

The hydrazino nitrogenous compound (hydrazine) synthesized as described above can be further converted to a hydrazide by reacting it with a carboxylic ester, or an acid halide in the presence of a base such as pyridine or DIEA.

Amino nitrogenous compounds (amines) may be further functionalized to form amides, hydrazides, carbamates, ureas, sulfonamides, sulfinamides and sulfanamides. An amide nitrogenous compound can be prepared by treating the amine with an acid halide, such as an acid chloride, in the presence of a base such as pyridine. Alternatively, amides can also be prepared by the action of an amine on a carboxylic ester.

Carbamates can also be synthesized from amines. The procedure involves reaction of the amine with an alkyl halide and potassium carbonate in the presence of a phase transfer catalyst such as $Bu_4NH^+$ $HSO_4^-$. Carbamates can also be obtained by the treatment of an amine with an appropriate alkyl or aryl chloroformate, or by reacting an amine with carbon monoxide, oxygen and an alcohol, in the presence of a catalyst such as pyridine.

Further, amines can be converted to ureas by reacting the amine with carbon monoxide in the presence of selenium or sulfur, or $Pd(OAc)_2$—$I_2$—$K_2CO_3$ (only for secondary amines). Also, amines can be added to isocyanates to form ureas. Symmetrically substituted ureas can be obtained by the reaction of an amine with phosgene or ethyl carbonate.

Sulfonamides can be prepared from amines by the reaction of an amine with a sulfonyl chloride in the presence of a base. Sulfinamides can be prepared by the reaction of an amine with a sulfinyl chloride in the presence of a base. The sulfonamide or sulfinamide thus formed can further be reduced to a sulfanamide by $LiAlH_4$, zinc and acetic acid or triphenylphosphine and iodine.

The nitrogen atoms of nitrogenous compounds such as amines, hydroxylamines, hydrazines, amides, carbamates, ureas, sulfonamides, sulfinamides and sulfanamides can be alkylated by treating the nitrogenous compound with a base such as sodium hydroxide or sodium hydride, and then reacting the resulting sodium salt with a halide such as the illustrative halides (benzyl bromide, 3-methylbenzyl bromide, 3-methoxybenzyl bromide or 3-nitrobenzyl bromide) used in the examples below. A wide spectrum of halides can be used for this purpose.

The above-mentioned nitrogenous compounds can also be acylated at the nitrogen atom by treating them with a base such as sodium hydroxide or sodium hydride, and then reacting the resultant sodium salt of the nitrogenous compound with an acid halide. Illustrative acid halides include, but are not limited to, benzoyl chloride, 3-methylbenzoyl chloride, 3-methoxybenzoyl chloride or 3-nitrobenzoyl chloride.

Additionally, the nitrogenous compounds can be functionalized at the nitrogen atom by reaction of the nitrogenous compound with an aldehyde or ketone forming a Schiff base. The Schiff base is then reduced in the presence of a reducing agent such as $NaCNBH_3$, sodium metal in ethanol, or organometallic compounds such as allylic boranes and allylic stannanes.

A general synthetic scheme for synthesis of illustrative compounds of the invention is shown in FIG. 1. Exemplified in this figure is the synthesis of a "hetera-heterophane" (a phane having a heterocyclic ring as well as hetero atoms in the bridge). This compound has three nitrogenous moieties in the bridge and a fourth nitrogenous moiety pendant to the heterocyclic ring. As illustrated in FIG. 1, a triazine was selected as the ring compound of the "phane" macrocycle. The bridge of the phane includes two nitrogenous amine moieties and one nitrogenous hydroxylamine moiety. A further nitrogenous amine moiety is included on a pendant group on the triazine ring.

Aside from having mixed nitrogenous moieties in the bridge, the bridge is also asymmetrical by virtue of the use of spacers of different lengths. The nitrogenous moieties are numbered 1 to 4 in FIG. 1. There is a propyloxy chain between positions 1 and 3, an ethyl chain between positions 2 and 3 and methyl chains between positions 1 and one of the bridgehead atoms of the ring and position 2 and the other of the bridgehead atoms of the ring.

In examples 32–55, and 98 the preparation of various ring structures is shown. These rings can be included in macrocyclic compounds of the invention by cyclizing them in the same manner as is described in Examples 56, 90, 97, 99, 104, 109, or 118. Compound 6 (a,b, or c) of FIG. 1 can be used as the bridge portion of the macrocycle during these cyclizations. Thus compounds having a macrocyclic structure as is illustrated by compound 10 in FIG. 1, compounds 26–30 in FIG. 6, compounds 33, 34, 37, and 38 in FIG. 7, compounds 45 and 46 in FIG. 8, compound 55 FIG. 10, compounds 62 and 63 FIG. 11, compounds 74 and 75 FIG. 13, and compounds 79 and 80 will be obtained. Further intermediates for forming the bridge portion of macrocyclic compounds of the invention are described in Examples 31, 89, 96, and 100–103. These bridge intermediates, and other bridge intermediates of similar structure, can be joined with ring systems to form macrocyclic compounds of the invention. These macrocyclic compounds are further functionalized at the nitrogen atoms of their nitrogenous species as is described in Examples 57–77, 106, 112, and 114.

The synthesis of macrocyclic compounds having 2 ring systems and 2 bridges is described in Examples 90, 97, and 99. These macrocyclic compounds are functionalized in an analagous manner to the macrocyclic compounds containing only one bridge and one ring system.

The synthesis and iterative deconvolution of a library of macrocyclic compounds of the invention is illustrated in FIGS. 2–5, Examples 57–72. A macrocyclic compound is treated as per the procedures illustrated in Examples 57–72 for combinatorialization of its nitrogenous sites. In the illustrative example, the macrocycle has four nitrogenous sites that can be combinatorialized. In combinatorializing these four sites, any number of a vast selection of chemical functional reactant species can be reacted with the nitrogenous sites to place chemical functional groups thereon.

The overall extent of diversification will be a factor of both the number of sites and the number of reactant species presented to each site for covalent bonding to the site. To achieve a library having limited diversification, only a few sites or chemical functional groups need be used as illustrated in Example 106. To achieve a high degree of diversification, one or the other, or both the number of sites and the number of chemical functional groups is expanded. The complexity of the library is represented by the number of chemical functional groups taken to the power represented by the number of sites these chemical functional groups can be located at. Thus for example, 5 chemical functional groups at three unique sites will give a library of 125 ($5^3$) compounds, 20 chemical functional groups at 4 sites will give a library of 160,000 ($20^4$) compounds and 8 chemical functional groups at 6 sites will give a library of 262,144 ($8^6$) compounds. Normally, to obtain a large library of a linear oligomeric compound such as a peptide, the length of the peptide, as for instance a 10-mer, offers a large number of sites. Thus, if all the 20 or so normal amino acids were utilized in making such a peptide library, very complex libraries (in the order of $10^{13}$ compounds) would result.

In constructing and assaying macromolecules of the invention, if an enzyme binder or a macromolecule with other like biological property is desired, normally a macromolecule having a smaller number of sites would be selected such that the spatial size (the three dimensional global footprint) of the macromolecule does not exceed a pre-selected size in order to fit into the enzyme pocket or other biological target. If uptake of a molecule is a consideration and it is determined that the molecular weight of the molecule should not exceed a pre-selected molecular weight range, as for instance a molecular weight of 500, 1000 or 1500, then a small number of sites might also be selected. In these instances, the number of sites that can be combinatorialized is maintained relatively small (less than 10, preferably less than 6 and even more preferred from 2 to 4). In order to construct very complex (large) libraries, a greater number of chemical functional groups are used to expand the libraries such that they contain a large number of individual species. As opposed to peptides, where normally only 20 amino acids are available for selection as the chemical functional groups, in diversifying the macromolecules of the invention one is not constrained as far as chemical functional groups are concerned. Any number of chemical functional groups can be selected.

For targets where size of the macromolecule is not an overriding consideration, such as in a metal ion scavenger to be used in an industrial waste stream, macromolecules having a large number of sites can be selected and the number of chemical functional groups decreased. Thus, only those chemical functional groups that are known to be metal coordinating groups might be selected. An expanded diversity would be achieved by selecting the macromolecule bridge and any pendant groups on the ring of the compound of the invention to include sufficient number of sites to ensure a high degree of diversity. Thus, in these instances, the number of nitrogenous moieties included in the molecule would be selected in the high range as for instance from 4 to 10, preferably 6 to 10.

The chemical functional groups can be selected based on chain length, i.e. short versus long, based on the use of a ring versus a linear group, use of an aromatic versus aliphatic group, use of a functionalized group versus a non-functionalized group, to mention only a few of the wide variety of chemical functional groups available. Indeed simply varying functional moieties, e.g. acid, alcohol, aldehyde, amide, amine, amidine, azo, azoxy, double bond, ether, ethylene oxide, guanidine, halide, haloalkyl, hydrazine, hydroxylamine, ketone, mercaptan, nitrate, nitrile, nitro, nitroso, quaternary nitrogen, sulfide, sulfone, sulfoxide, triple bond, urea, etc. on a single backbone, e.g. a simple alkyl group, yields a vast array of diversity functions. When this is expanded to include placement of such varied functional moieties on a broad platform of backbones, e.g. a series of alkyl compounds, a series of aryl compounds, a series of alicyclic compounds, etc., the potential for a vast array of chemical functional groups is apparent. Other chemical functional groups include alkyl, alkenyl, alkynyl, alicyclic and substituted alkyl, alkenyl, alkynyl, alicyclic; aryl and substituted aryl; aralkyl, substituted aralkyl, heterocycles, moieties as found in the a-position of amino acids, nucleobases such as pyrimidines and purines; and metal chelating groups.

Chemical functional groups of the invention can be represented by structure:

where T is a single bond, a methylene group or a group having structure:

where:

$R^6$ is $=O$, $=S$, $=NR^3$;

$R^5$ and E, independently, are a single bond, $CH=CH$, $C\equiv C$, O, S, $NR^3$, $C_6$–$C_{14}$ aryl;

each $R^1$, $R^2$ and $R^3$ are, independently, H, alkyl or haloalkyl having 1 to about 10 carbon atoms; alkenyl having 2 to about 10 carbon atoms; alkynyl having 2 to about 10 carbon atoms; or aryl having 7 to about 14 carbon atoms;

m and n, independently, are zero to 5;

p is zero or 1;

q is 1 to about 10; and

L is, H; $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocyclic alkyl, alkenyl or alkynyl or substituted carbocyclic, or $C_6$–$C_{14}$ aryl or substituted aryl where the substituent groups are selected from hydroxyl, amino, alkoxy, alcohol, benzyl, phenyl, nitro, thiol, thioalkoxy, halogen, alkyl, aryl, alkenyl, or alkynyl groups; an ether having 2 to 10 carbon atoms and 1 to 4 oxygen or sulfur atoms; a nitrogen, sulfur or oxygen containing heterocycle; a metal coordination group; a conjugate group; halogen; hydroxyl (OH); thiol (SH); keto (C=O); carboxyl (COOH); amide ($CONR^1$); amidine ($C(=NH)NR^1R^2$); guanidine ($NHC(=NH)NR^1R^2$); glutamyl $R^3OOCCH(NR^1R^2)(CH_2)^2C(=O)$—); nitrate ($ONO_2$); nitro ($NO_2$); nitrile (CN); trifluoromethyl ($CF_3$); trifluoromethoxy ($OCF_3$); O-alkyl; S-alkyl; NH-alkyl; N-dialkyl; O-aralkyl; S-aralkyl; NH-aralkyl; amino ($NH_2$); azido ($N_3$); hydrazino ($NHNH_2$); hydroxylamino ($ONH_2$); sulfoxide (SO); sulfone ($SO_2$).; sulfide (S—); disulfide (S—S); silyl; a nucleosidic base; an amino acid side chain; a carbohydrate; a drug; or group capable of hydrogen bonding.

To introduce the chemical functional groups on to the nitrogenous moieties, various chemical functional group reactant compounds, i.e. the reactive forms of the chemical functional groups, having a further functional group thereon are used. These further functional groups can include, but are not limited to, OHC— (aldehydes), $OR_1C$— (ketones), halogen, $HO_2C$—, and halogen-CO— (acid halide). The "diversity end" of these chemical functional group reactant compounds have other functionalities thereon, as noted above. Illustrated in FIGS. 2–5 is the combinatorialization of a macromolecule having four nitrogenous sites coupled with four chemical functional groups to achieve an overall complexity of 256 ($4^4$) compounds. A "fix last" deconvolution strategy is utilized.

Figure 2:
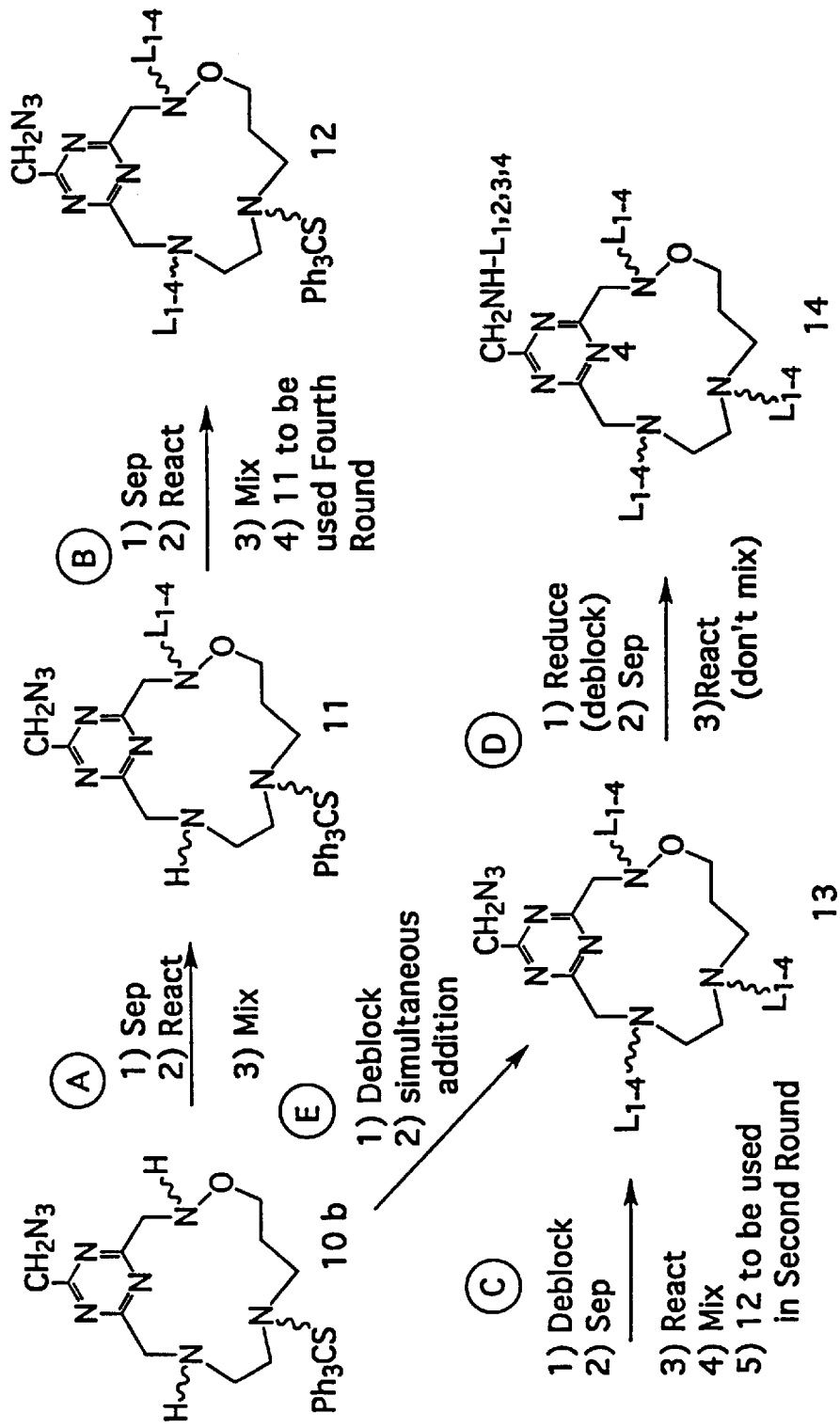
FIG. 2 shows processes for a first round of synthesis for preparing libraries of compounds according to the invention.

Illustrated in FIG. 2 is the first round, round one, of this "fix last" combinatorial procedure. Four chemical functional groups are utilized. These are labeled $L_1$ to $L_4$. When all of the groups are present at any one site (on different molecules of the population), the chemical functional groups are noted as "$L_{1-4}$". When but a single chemical functional group is located at a particular site, it is labeled as, for example, $L_1$. When pools of separate molecules (in reality, pool of a large population of the same molecular species) are identified, the individual pools are labeled as $L_{1,2,3,4}$. In the procedure illustrated in FIG. 2, during the procedure, sites 1, 2 and 3 are combinatorialized, that is any one of the four chemical functional groups can reside on any particular individual molecule (or populations of that molecular species). There is a population of molecules having chemical functional group 1 at site one, chemical functional group 1 at site 2, chemical functional group 1 at site 3; a population having chemical functional group 2 at site 1, chemical functional group 1 at site 2 and chemical functional group 1 at site 3; a population having chemical functional group 3 at site 1, chemical functional group 1 at site 2 and diversity group 1 at site 3; etc. until one reaches a population having chemical functional group 4 at site 1, chemical functional group 4 at site 2 and chemical functional group 3 at site 3; and a population having chemical functional group 4 at site 1, chemical functional group 4 at site 2 and chemical functional group 4 at site 3. Thus, the "etc." portion of the preceding sentence represents all of the other combinations between the given extremes.

After sites 1, 2 and 3 are combinatorialized, as the last step of the procedure, the totality of the molecules in the library are divided into four groups or pools and each pool is reacted with the reactant form of but a single, known chemical functional group to covalently bond that chemical functional group to site 4. Thus the identity of the chemical functional group at site 4 is known. Each pool will include 64 different molecular species and there will be 4 such pools for a total of 256 total molecular species present in the library.

As illustrated in FIG. 2, the procedure includes as its last step, "fixing" the chemical functional group on the nitrogenous moiety at site 4, the pendant ring site. Stated otherwise, three of the four nitrogenous moieties of the illustrated macrocycle are reacted with appropriate reactant species that carry diversity functions thereon. Prior to reaction of the fourth nitrogenous site, the reaction mixture is divided into the same number of pools as there are chemical functional groups, i.e. four pools in this illustrative example, and maintained as four distinct pools. Each pool is treated with a single known reactant. Thus, the identity of the chemical functional group bonded to the nitrogen atom at site 4 of molecules in each pool is known. The individual pools of compounds of the invention are then screened for an activity of interest.

During round one, in combinatorializing the four sites of the compound, a blocking group is used at sites 3 and 4. The blocking group utilized at site 3 is a "removable" blocking group that simply "masks" the site against reaction with incoming reactant molecules. The blocking group utilized at site 4 is a "precursor-type" blocking group, i.e. it is a functional group that can be modified via a chemical reaction to form a different functional group, such as the desired nitrogenous moiety.

Figure 3:
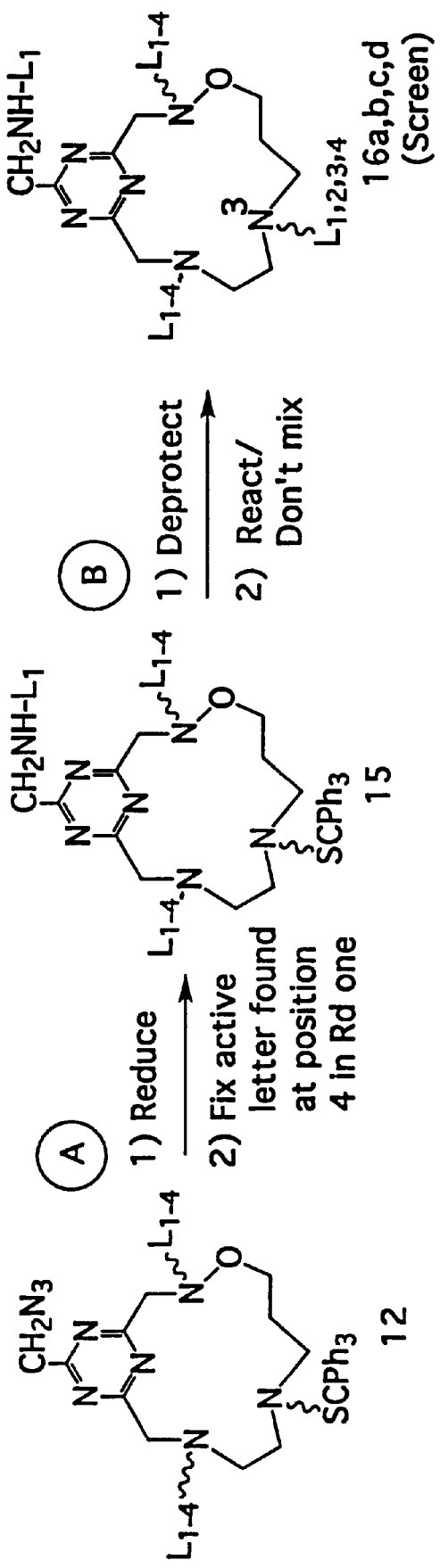
FIG. 3 shows processes for a second round of synthesis for preparing libraries of compounds according to the invention.

After completion of combinatorializing site 1,2 and 3 and fixing site 4, the pools are assayed. For any pool that shows activity in a specific functional assay, further sites are sequentially fixed and assayed. Thus, as shown in FIG. 3, for the second round, site 3 can be selected as the site to be fixed next. This is effected by combinatorializing sites 1 and 2, as per the same procedure described for round one in FIG. 2. A more facile way to achieve this is to set aside an aliquot of the intermediate library of round one to be later used in the second round. This method can also be used in later rounds, i.e. setting aside aliquots of intermediate mixtures of compounds from earlier rounds. Site 4 is then "deblocked" and reacted with the desired chemical functional group, in its reactive form, that has been identified by assaying the pools of round one. This fixes site 4 with the selected chemical functional group ascertained from round one. The blocking group from site 3 is removed, the totality of the reaction mixture is divided into pools and each pool is treated with a known chemical functional group reactant. The pools are again assayed for desired activity and the most active pool is now ready for further deconvolution.

Figure 4:
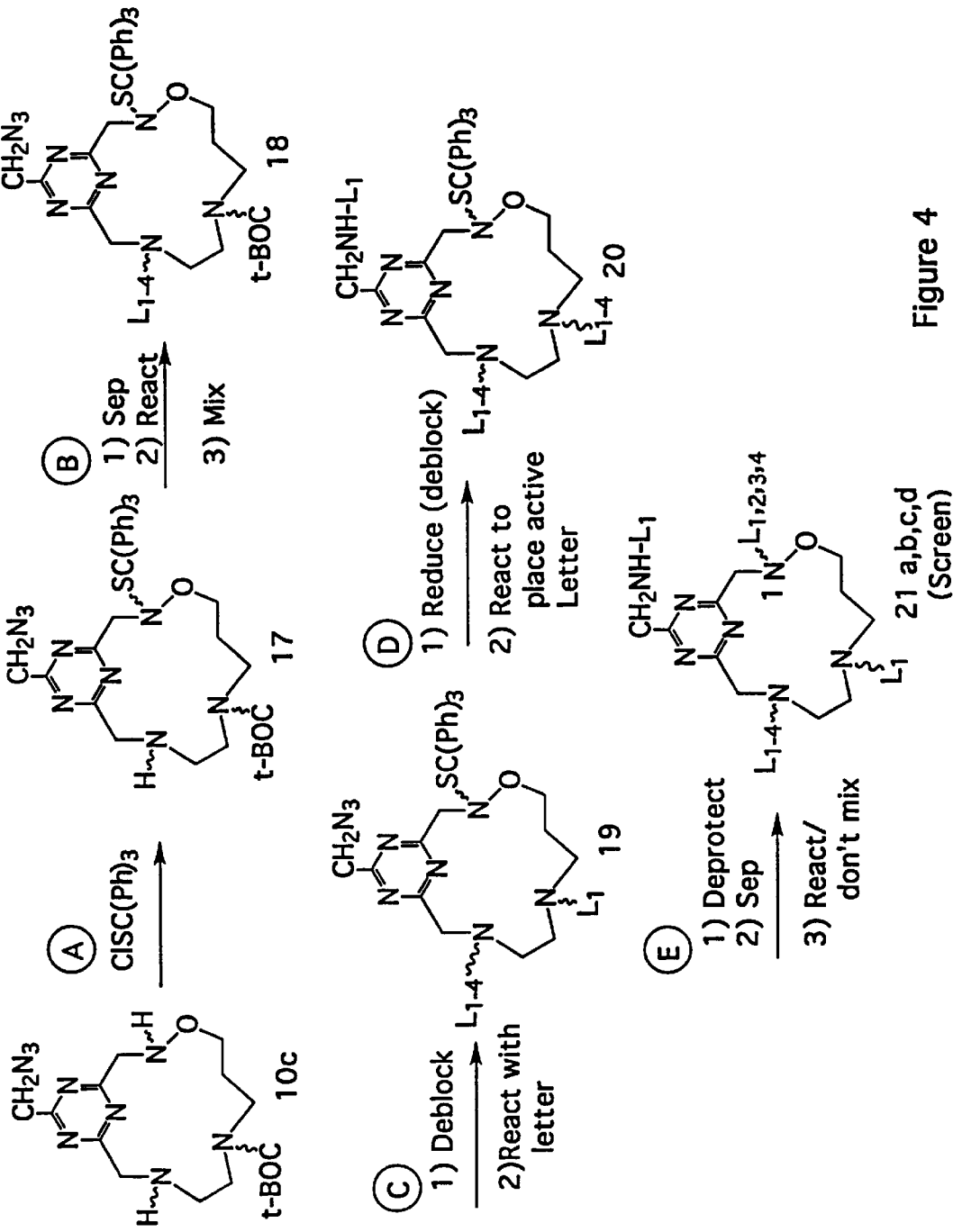
FIG. 4 shows processes for a third round of synthesis for preparing libraries of compounds according to the invention.

In round three, illustrated in FIG. 4, the most active chemical functional group at site 1 is now fixed. Again the "fix last" strategy is utilized. Site 1 is blocked. Site 2 is combinatorialized. Site 3 is deblocked and is fixed with the chemical functional group selected from the second round. Site 4 is deblocked and fixed with the chemical functional group selected from the first round screening. Site 1 is deblocked and the reaction mixture divided into four pools. Each separate pool is fixed with one of the chemical functional groups and each pool separately assayed for the desired activity. The most active pool is selected.

The fourth round of deconvolution now fixes site 2. This is effected by fixing site 1 with the chemical functional group selected in round three followed by blocking site 2. Site 3 is deblocked and fixed with the selected chemical functional group selected from round two. Site 4 is deprotected and fixed with the chemical functional group selected from round one. Site 2 is now deblocked, the reaction mixture is divided into pools and each pool is reacted with a different chemical functional group reactant. The resulting pools are individually assayed and the final molecule of interest is ascertained from this final assay. Of the 256 compounds possible in the library, one has now been selected that shows the greatest desired activity in the functional assays effected at the conclusion of each of rounds one, two, three and four.

In addition to the preceding process for the deconvolution of combinatorial libraries, which includes the iterative processes of splitting and fixing one position, there are many other strategies used by those skilled in the art. One such strategy utilizes a subtractive technique where selected letters are removed from selected pools and the active pools are pursued to elicit the most active compound (see e.g., Carell, T., supra). Other methods known in the art include labeling (including chemically or radioisotopically), enzyme binding assays, and selection assays. Another method, mentioned previously, is fixing one letter at a time. A further method involves the use of protecting groups to make selected sites unavailable for functionalization until other sites are functionalized. Many of these methods can be combined to customize conditions to meet synthetic needs.

For the purpose of illustration, in the examples below, during combinatorialization six aromatic chemical functional groups or letters are employed. Specifically, benzyl, m-methylbenzyl, m-nitrobenzyl, and m-methoxybenzyl moieties are used for the preparation of the libraries in Examples 57–72, and m-anisoyl and m-toluoyl moieties are used for the preparation of the library of Example 106. It is to be recognized that this is for illustrative purposes only, and this invention is not to be construed as being limited to only this number of chemical functional groups or to these particular chemical functional groups during a combinatorialization of any particular macrocyclic compound of the invention. The precursor compounds for the illustrated chemical functional groups as well as precursor compounds for multitudes of other such chemical functional groups are commercially available from several commercial sources. Other chemical functional groups, for example alkyl, alkenyl, alkynyl, amino acid side chains, nucleobases and the like, are utilized in the same manner.

In the illustrative examples below, the basic chemistry employs various types of nitrogenous moieties, e.g. primary amine, secondary oxyamine, secondary amine, each of which is protected with a suitable protecting group when necessary. For illustrative purposes, the protective groups selected for protecting these nitrogen atoms are azido (a precursor-type protecting group), tert-butoxycarbonyl, sulfenyltriphenyl and phthaloyl. The tert-butoxycarbonyl (t-Boc) and the sulfenyltriphenyl [S(Ph)$_3$] moieties can be removed under differential acid conditions, and the phthaloyl moiety can typically be removed with hydrazine (basic conditions), or under certain acid conditions.

EXAMPLE 1

N-t-Boc-2-amino-1-bromoethane 2-bromoethylamine hydrobromide (14.3 g, 70 mmol) was dissolved in CH$_3$CN (250 mL) and triethyl amine (11 mL, 77 mmol) and di-t-butyl dicarbonate (15.2 mL, 66.5 mmol) was added. The reaction mixture was stirred at room temperature for 12 hours under an atmosphere of argon. Saturated NaHCO$_3$ (200 mL, aq) was added and stirring was continued for 15 minutes. The mixture was poured into a separatory funnel and extracted several times with ether. The combined ether extracts were dried over Na$_2$SO$_4$. The dried ether layer was filtered and concentrated in vacuo to give 15.28 g (97.4%) of the title compound. TLC (Rf: 0.7; 10% MeOH/ CH$_2$Cl$_2$). $^1$H NMR (CDCl$_3$) δ 1.5 (s, 9H, t-butyl CH$_3$), 3.5 (m, 4H, CH$_2$), 5.1 (s, 1H, NH). $^{13}$C NMR (CDCl$_3$) δ 28.3 (CH$_3$), 32.7 (CH$_2$), 42.3 (CH$_2$), 79.7 (C(CH$_3$)$_3$), 155.5 (CO).

EXAMPLE 2

N-t-Boc-(2-azido)-1-aminoethane

N-t-Boc-2-amino-1-bromoethane (15.28 g, 68.2 mmol) was suspended in DMF (200 mL) and sodium azide (5.0 g, 75 mmol) was added. The reaction mixture was stirred at about 80° C. for 12 hours under an atmosphere of argon. The reaction mixture was cooled and diluted with ether (400 mL). The reaction mixture was washed five times with saturated NaCl and dried over Na$_2$SO$_4$. The dried ether layer was filtered and concentrated in vacuo to give 9.8 g (77.1%) of the title compound. TLC (Rf: 0.4; 20% EtOAc/Hexane). $^1$H NMR (CDCl$_3$) δ 1.4 (s, 9H, t-butyl CH$_3$), 3.2 (t, 2H, CH$_2$), 3.3 (m, 2H, CH$_2$), 4.9 (s, 1H, NH). $^{13}$C NMR (CDCl$_3$) δ 28.2 (CH$_3$), 40 (CH$_2$), 51.1 (CH$_2$), 79.7 (C(CH$_3$)$_3$), 155.7 (CO).

EXAMPLE 3
N-t-Boc-diaminoethane 1 (FIG. 1)

To N-t-Boc-(2-azido)-1-aminoethane (9.8 g, 52.6 mmol), in THF (200 mL), was added H$_2$O (0.8 mL) and triphenyl phosphine (15 g, 58 mmol). The reaction mixture was stirred at about 80° C. for 12 hours under an atmosphere of argon. The reaction mixture was evaporated to a white solid residue. NaH$_2$PO$_4$ (200 mL, 0.5 M, aq) was added and the mixture was stirred for about 15 minutes. The mixture was washed with EtOAc. The aqueous layer was separated and made basic with 3 N NaOH. The resulting mixture was extracted with ether and the combined ether extracts dried over Na$_2$SO$_4$. The dried ether layer was filtered and concentrated in vacuo to give 8.1 g (96.5%) of the title compound. TLC (Rf: 0.2; 20% MeOH/CH$_2$Cl$_2$). $^1$H NMR (CDCl$_3$) δ 1.3 (s, 2H, NH$_2$), 1.4 (s, 9H, t-butyl CH$_3$), 2.8 (t, 2H, CH$_2$), 3.2 (m, 2H, CH$_2$), 4.8 (s, 1H, NH). $^{13}$C NMR (CDCl$_3$) δ 28.4 (CH$_3$), 41.9 (CH$_2$), 43.5 (CH$_2$), 79.2 (C(CH$_3$)$_3$), 156.2 (CO).

The title compound was also prepared according to the procedure of Saari, et.al., *J. Med. Chem.*, 1990, 33 97–101.

EXAMPLE 4
1-(Methanesulfonyl)-3-chloropropanol 2 (FIG. 1)

To a solution of 3-chloro-1-propanol (283 g, 2.99 mol) and triethylamine (629 mL, 4.5 mol) in CH$_3$CN (3500 mL) at 10° C. was added dropwise methanesulfonyl chloride (518 g, 4.52 mol). The resulting reaction mixture was stirred overnight at room temperature, filtered and concentrated in vacuo to an oil. The oil was dissolved in CH$_2$Cl$_2$ and purified by filtration through silica gel. The appropriate fractions were combined and concentrated in vacuo to give the title compound 335 g (65%). TLC (Rf: 0.3; 20% EtOAc/Hexane). $^1$H NMR (CDCl$_3$) δ 2.1 (m, 2H, CH$_2$), 2.96 (s, 3H, CH$_3$), 3.59 (t, 2H, CH$_2$), 4.28 (t, 2H, CH$_2$). $^{13}$C NMR (CDCl$_3$) δ 31.5 (CH$_2$), 37.0 (CH$_3$), 40.2 (CH$_2$), 66.3 (CH$_2$).

EXAMPLE 5
1-(p-Toluenesulfonyl)-3-chloro-1-propanol

To 3-Chloro-l-propanol (5.02 mL, 60 mmol) was added CH$_3$CN (200 mL), p-toluenesulfonyl chloride (17 g, 90 mmol) and pyridine (7.3 mL, 90 mmol). The reaction mixture was stirred at room temperature for 12 hours under an atmosphere of argon. Saturated NaHCO$_3$ (200 mL, aq) was added and stirring was continued for 15 minutes. The mixture was then poured into a separatory funnel and extracted several times with CH$_2$Cl$_2$. The CH$_2$Cl$_2$ extracts were combined and dried over Na$_2$SO$_4$. The CH$_2$Cl$_2$ layer was filtered and concentrated in vacuo to give 12.35 g (83.8%) of the title compound. TLC (Rf: 0.5; 20% EtOAc/Hexane). $^1$H NMR (CDCl$_3$) δ 2.1 (m, 2H, CH$_2$), 2.5 (s, 3H, CH$_3$), 3.6 (t, 2H, CH$_2$), 4.2 (t, 2H, CH$_2$), 7.6 (d & d, 4H, Ar). $^{13}$C NMR (CDCl$_3$) δ 21.4 (CH$_3$), 31.5 (CH$_2$), 40.2 (CH$_2$), 66.7 (CH$_2$), 127.8 (Ar), 129.8 (Ar), 132.5 (Ar), 144.9 (Ar).

EXAMPLE 6
1-O-Phthalimido-3-bromo-1-propanol

A mixture of N-hydroxyphthalimide (16.3 g, 100 mmol) and 1,3-dibromopropane (20.19 g, 100 mmol) in dry DMF (150 mL) and triethyl amine (15.33 mL, 110 mmol) is stirred at 20 to 75° C. for 1 to 10 hours. After filtration, the mixture is evaporated to dryness in vacuo. The residue is purified by silica gel flash column chromatography to give the title compound.

EXAMPLE 7
N-[N-t-Boc(2-aminoethyl)]-3-chloropropane 3 (FIG. 1)
Method 1

N-t-Boc-diaminoethane (6.75 g, 42.13 mmol), and 1-(methanesulfonyl)-3-chloropropanol (30.59 g, 177 mmol) was stirred in THF (80 mL) at room temperature under an atmosphere of argon. Sodium carbonate (21 g, 198 mmol) was added and the reaction mixture was equilibrated to room temperature with stirred for 12 hours. 0.5 M NaH$_2$PO$_4$ (100 mL, aq) was added and the aqueous layer was separated and extracted with toluene. The aqueous layer was made basic with NaOH and extracted with ether. The combined ether extracts were dried over Na$_2$SO$_4$. The dried ether layer was filtered and evaporated to an oily residue. The residue was purified by silica gel flash column chromatography using MeOH/CH$_2$Cl$_2$ as the eluent. The pure fractions were pooled together and evaporated to dryness to give 0.45 g (49.5%) of the title compound. TLC (Rf: 0.5; 20% MeOH/CH$_2$Cl$_2$). $^1$H NMR (CDCl$_3$) δ 1.4 (s, 9H, t-butyl CH$_3$), 1.9 (m, 2H, CH$_2$), 2.7 (q, 4H, CH$_2$), 3.2 (m, 2H, CH$_2$), 3.6 (t, 2H, CH$_2$), 4.9 (s, 1H, NH). $^{13}$C NMR (CDCl$_3$) δ 28.4 (CH$_3$), 32.7 (CH$_2$), 40.3 (CH$_2$), 42.9 (CH$_2$), 46.4 (CH$_2$), 49.1 (CH$_2$), 79.3 (C(CH$_3$)$_3$), 156.2 (CO).
Method 2

A mixture of N-t-Boc-diaminoethane (94 g, 0.59 mol), anhydrous sodium carbonate (100 g, 0.94 mol), 1-(methanesulfonyl)-3-chloropropanol (278 g, 1.6 mol) in dry THF (2000 mL) was heated to 45° C. with vigorous stirring for 18 hours. The reaction mixture was filtered and the mother liquor concentrated in vacuo. The gum was partitioned between ether and water and extracted with ether (2×500 mL). The combined ether extracts were extracted with 3% HCl solution (2×500 mL) and the aqueous layer was immediately made basic with Na$_2$CO$_3$ (pH 8.5). The aqueous layer was extracted with ether (2×500 mL), dried (MgSO$_4$), filtered, and concentrated in vacuo to give the crude product 74 g (47% purity). The crude product was purified by silica gel flash column chromatography using CH$_2$Cl$_2$/MeOH 8:2 as the eluent to give the title compound. $^1$H NMR (CDCl$_3$) δ 1.4 (s, 9H, t-butyl), 1.9 (m, 2H, CH$_2$), 2.7 (q, 4H, CH$_2$), 3.2 (m, 2H, CH$_2$), 3.6 (t, 2H, CH$_2$), 4.9 (x, 1H, NH).

EXAMPLE 8
N-[N-t-Boc(2-aminoethyl)]-O-phthalimido-3-amino-1-propanol 5 (FIG. 1)

A mixture of N-t-Boc-diaminoethane (100 mmol) and 1-O-phthalimido-3-bromo-1-propanol (100 mmol) in dry DMF and triethyl amine (110 mmol) is stirred at 20 to 75° C. for 1 to 25 hours. After filtration, the mixture is evaporated to dryness under reduced pressure. The residue is distributed between water and ethyl acetate. The organic layer is separated, dried (MgSO$_4$), and concentrated in vacuo to dryness. The residue is purified by silica gel flash column chromatography to give the title compound.

EXAMPLE 9
N-[N-t-Boc(2-aminoethyl)]-N-tritylsulfenyl-3-amino-1-chloropropane N-[N-t-Boc(2-aminoethyl)]-3-chloropropane (420 mg, 1.7 mmol), triphenylmethanesulfenyl chloride, i.e. tritylsulfenyl chloride, (0.42 g, 1.36 mmol), and pyridine (0.7 mL, 8.5 mmol) were stirred in CH$_2$Cl$_2$ (30 mL) under an atmosphere of argon for 12 hours. 0.5 M NaH$_2$PO$_4$ (20 mL, aq) was added and the aqueous layer was extracted several times with $CH_2Cl_2$. The combined $CH_2Cl_2$ extracts were combined and dried over $Na_2SO_4$. The dried $CH_2Cl_2$ layer was filtered and evaporated to an oily residue. The residue was purified by silica gel flash column chromatography using EtOAc/Hexane as the eluent. The pure fractions were pooled and evaporated in vacuo to give 150 mg (17.3%) of the title compound. TLC (Rf: 0.5; 20% EtOAc/Hexane). $^1$H NMR (CDCl$_3$) δ 1.4 (s, 9H, t-butyl CH$_3$), 1.9 (m, 2H, CH$_2$), 2.9 (m, 4H, CH$_2$), 3.2 (m, 2H, CH$_2$), 3.4 (t, 2H, CH$_2$), 4.6 (s, 1H, NH). $^{13}$C NMR (CDCl$_3$) δ 28.4 (CH$_3$), 29.7 (CH$_2$), 37.9 (CH$_2$), 42.2 (CH$_2$), 53.4 (CH$_2$), 56.5 (CH$_2$), 79.3 (C(CH$_3$)$_3$), 127.2 (Ar), 127.9 (Ar), 130.1 (Ar), 143.0 (Ar), 156.2 (CO).

EXAMPLE 10
N-[N-t-Boc-(2-aminoethyl)]-N-tritylsulfenyl-3-amino-1-O-phthalimidopropanol 5b (FIG. 1)

Sodium carbonate (7.5 mmol) and N-hydroxyphthalimide (0.75 mmol) are added to N-[N-t-Boc-(2-aminoethyl)]-N-tritylsulfenyl-3-amino-l-chloropropane (1.7 mmol) in DMF (5 mL). The reaction mixture is stirred under an atmosphere of argon at 80° C. for 6 hours and at room temperature for an additional 12 hours. After filtration, H$_2$O (about 20 mL) is added and the aqueous layer is extracted several times with ether. The combined ether extracts are dried over Na$_2$SO$_4$ and filtered. The filtrate is evaporated to give the title compound.

EXAMPLE 11
N-(2-aminoethyl)-O-phthalimido-3-amino-1-propanol 8a (FIG. 1)

A mixture of N-[N-t-Boc-(2-aminoethyl)]-O-phthalimido-3-amino-1-propanol and 50% aqueous trifluoroacetic acid/methylene chloride (1:1) is heated at 20 to 50° C. for 1 to 24 hours and treated with saturated NaHCO$_3$. The mixture is evaporated to dryness under reduced pressure. The residue is purified by silica gel flash column chromatography to give the title compound.

EXAMPLE 12
N-[N-t-Boc(2-aminoethyl)]-O-amino-3-amino-1-propanol 7a (FIG. 1)

To N-[N-t-Boc(2-aminoethyl)]-O-phthalimido-3-amino-1-propanol (420 mg, 1.7 mmol) in DMF (5 mL) was added, sodium carbonate (80 mg, 7.5 mmol) and N-hydroxyphthalimide (0.12 g, 0.75 mmol). The reaction mixture was stirred under an atmosphere of argon at 80° C. for 6 hours and at room temperature for an additional 12 hours. After filtration, H$_2$O (about 20 mL) was added and the aqueous layer was extracted several times with ether. The combined ether extracts were dried over Na$_2$SO$_4$ and filtered. The filtrate was evaporated to give the title compound. TLC (Rf: 0.4; 20% MeOH/Hexane). $^1$H NMR (CDCl$_3$) δ 0.9 (m, 1H, NH), 1.4 (s, 9H, t-butyl CH$_3$), 1.8 (s, 2H, NH$_2$), 2.1 (m, 2H, CH$_2$), 2.5 (t, 2H, CH$_2$), 3.1 (m, 2H, CH$_2$), 3.2 (t, 4H, CH$_2$), 4.9 (s, 1H, NH). $^{13}$C NMR (CDCl$_3$) δ 28.4 (CH$_3$), 29.7 (CH$_2$), 38.4 (CH$_2$), 55.2 (CH$_2$), 58.8 (CH$_2$), 75.9 (CH$_2$), 79.3 (C(CH$_3$)$_3$), 156.2 (CO).

EXAMPLE 13
N-[N-t-Boc(2-aminoethyl)]-N-tosyl-3-chloropropane 4d (FIG. 1)

A solution of crude N1-t-Boc-N2-(3-chloro)propyl-diaminoethane (71.8 g ~47%, ~0.13 mol) in CH$_2$Cl$_2$ (~1000 mL), triethylamine (50 mL, 0.36 mol) and tosyl chloride (24 g, 0.237 mol) was stirred at room temperature for 16 hours. The solution was washed with cold HCl (3%, 2×300 mL), saturated NaHCO$_3$ (1×100 mL), saturated NaCl (1×100 mL), dried (MgSO$_4$), filtered and concentrated in vacuo to a solid. The solid was purified by silica gel flash column chromatography to give 55.9 g (99%) of the title compound, (mp 95–96° C.). $^1$H NMR (CDCL$_3$) δ 1.42 (s, 9H, t-Butyl), 2.0 (m, 2H, CH$_2$), 2.41 (s, 3H, CH$_3$), 3.22 (m, 6H, CH$_2$), 3.55 (m, 2H, CH$_2$), 4.91 (bs, 1H, NH), 7.30 (d, 2H, ArH), 7.66 (d, 2H, ArH).

EXAMPLE 14
N-[N-t-Boc(2-aminoethyl)]-N-tosyl-O-phthalimido-3-amino-1-propanol 5d (FIG. 1)

A suspension of N-[N-t-Boc(2-aminoethyl)]-N-tosyl-3-chloropropane (27 g, 0.69 mol), sodium iodide (13.5 g, 0.09 mol), sodium carbonate (10.8 g, 0.10 mol) and N-hydroxyphthalimide (16.5 g, 0.1 mol) in DMF (1000 mL) was stirred vigorously at 80° C. for 24 hours. The reaction mixture was concentrated in vacuo, the residue was dissolved in CH$_2$Cl$_2$ and washed thoroughly with H$_2$O (3×200 mL). The organic layer was dried (MgSO$_4$), filtered and concentrated in vacuo to afford a solid. Recrystallization from MeOH gave the title compound 20.0 g (56%) (mp 111–112° C.). $^1$H NMR (CDCl$_3$) δ 1.41 (s, 9H, t-butyl), 2.0 (m, 2H, CH$_2$), 2.41 (s, 3H, Ar—CH$_3$), 3.20 (m, 6H, CH$_2$), 4.25 (t ,2H, CH$_2$), 5.07 (bs, 1H, NH), 7.29 (d, 2H, ArH), 7.67 (m, 6H, ArH).

EXAMPLE 15
N-Trifluoroacetyl-3-amino-1-O-dimethoxytritylpropanol

3-Amino-1-propanol (Aldrich, 1 g, 13.31 mmol) was dissolved in CH$_2$Cl$_2$ (40 ml) and 1 equivalent of ethyltrifluoroacetate (1.58 mL, 13.31 mmol) was added at room temperature. The reaction was complete in 2 hours as indicated by TLC. The reaction mixture was concentrated in vacuo and the resulting residue was coevaporated with pyridine (3×25 ml). The clear oil was re-dissolved in pyridine (50 ml) and one equivalent of triethylamine (1.87 ml, 13.31 mmol) was added. Dimethoxytritylchloride (4.51 g, 13.31 mmol) was added in four equal portions. The reaction was complete in 20 hours as indicated by TLC. The reaction mixture was partitioned between CH$_2$Cl$_2$ and water. The CH$_2$Cl$_2$ layer was separated, dried (MgSO$_4$), filtered and concentrated in vacuo. The resulting residue was purified by silica gel flash column chromatography using a gradient of 5% to 10% EtOAc in hexanes with 1% triethyl amine as the eluent. The appropriate fractions were pooled and concentrated in vacuo to give 5.29 g (84%) of the title compound. $^1$H NMR (DMSO) δ 1.79 (m, 2H, CH$_2$), 3.01 (t, 2H, CH$_2$), 3.32 (t, 2H, CH$_2$), 3.75 (s, 6H, 2x OCH$_3$), 6.88 (d, 4H, DMT), 7.23–7.40 (m, 9H, DMT), 9.36 (bs, 1H, NH). $^{19}$F NMR (DMSO) δ −75.72 (s, CF$_3$), ($^{19}$F peaks referenced to trifluoroacetic acid).

EXAMPLE 16
N-Acetylmethyl-N-trifluoroacetyl-3-amino-1-O-dimethoxytritylpropanol N-(Trifluoroacetyl)-3-amino-1-O-dimethoxytritylpropanol (40 g, 84.50 mmol) was dissolved in DMF (600 ml) and cooled in an ice bath to 0° C. NaH (60% dispersion, 4 g, 1.2 eq., 101.40 mmol) was added in 4 equal portions and the reaction mixture was allowed to stir for 2 hours at 0° C. before methylbromoacetate (10.31 mL, 92.95 mmol) was added dropwise. The reaction was slowly warmed up to room temperature overnight. The reaction was complete in 20 hours as indicated by TLC. The reaction mixture was concentrated in vacuo to approximately 100 ml. The reaction mixture was then partitioned between H$_2$O and CH$_2$Cl$_2$ (100 ml 1:1). The CH$_2$Cl$_2$ layer was dried (MgSO$_4$) and concentrated in vacuo. The resulting residue was purified by silica gel column flash chromatography using a gradient of 5% to 10% EtOAc in hexanes with 1% triethyl amine as the eluent. The appropriate fractions were pooled and concentrated in vacuo to give the title compound 35.90 g (83%). $^1$H NMR (CDCl$_3$) δ 1.89 (m, 2H, CH$_2$), 3.12 (dd, 2H, CH$_2$), 3.61 (dd, 2H, CH$_2$), 3.70 (x, 6H, 2x OCH$_3$), 3.76 (d, 3H, CH$_3$), 4.08 (s, 2H, CH$_2$), 6.82–7.43 (m, 13H, DMT). $^{19}$F NMR (CDCl$_3$) δ −75.57 s, (CF$_3$), −75.15 (s, CF$_3$), (peaks referenced to trifluoroacetic acid). $^{13}$C NMR (CDCl$_3$) spectra is consistent with structure.

EXAMPLE 17
N-(2-Hydroxyethyl)-3-amino-1-O-dimethoxytritylpropanol

N-Acetylmethyl-3-amino-1-O-dimethoxytritylpropanol (4.40 g, 8.62 mmol) was dissolved in a minimal amount of CH$_2$Cl$_2$ (75 ml) and MeOH (200 ml) was added. NaBH$_4$ (1.30 g, 34.48 mmol) was added in four equal portions. The reaction mixture was stirred at room temperature for 18 hours. After 18 hours the reaction had gone to completion as indicated by TLC. The reaction mixture was concentrated in vacuo to leave a white waxy solid which was partitioned between H$_2$O and EtOAc (100 mL, 1:1). The H$_2$O layer was extracted with EtOAc (3×50 ml). The EtOAc extracts were collected and dried (MgSO$_4$), filtered and concentrated in vacuo. The resulting residue was purified by silica gel flash column chromatography using a gradient of 5% to 10% MeOH in CH$_2$Cl$_2$ with 1% triethyl amine. The appropriate fractions were pooled and concentrated in vacuo to give the title compound 1.42 g (42%).

EXAMPLE 18
N-(2-Hydroxyethyl)-N-tritylsulfenyl-3-amino-1-O-dimethoxytritylpropanol N-(2-Hydroxyethyl)-3-amino-1-O-dimethoxytritylpropanol (5 g, 11.86 mmol) is dissolved in pyridine (100 ml) and the reaction flask is flushed with Argon and cooled to 0° C. in an ice bath. Trimethylsilylchloride (3.86 g, 35.58 mmol) is added dropwise and the reaction mixture is stirred for 1 hour. Triphenylmethanesulfenyl chloride (0.42 g, 1.36 mmol) is dissolved in CH$_2$Cl$_2$ and added via dropping funnel to the cooled reaction mixture. The reaction mixture is warmed to room temperature and stirred for 18 hours. The reaction mixture is concentrated in vacuo and the resultant residue is partitioned between H$_2$O and EtOAc (100 ml, 1:1). The H$_2$O layer is separated and extracted with EtOAc (3×50 mL). The EtOAc extracts are pooled, dried (MgSO$_4$) and filtered. The filtrate is concentrated in vacuo and the residue is purified by silica gel flash column chromatography with EtOAc and hexanes with 1% triethyl amine as the eluent. The appropriate fractions are pooled and concentrated in vacuo to give the title compound.

EXAMPLE 19
N-[2-(O-p-Toluenesulfonyl)hydroxyethyl]-N-tritylsulfenyl-3-amino-1-O-dimethoxytritylpropanol N-(2-Hydroxyethyl)-N-tritylsulfenyl-3-amino-1-O-dimethoxytritylpropanol (5.0 g, 7.49 mmol) is dissolved in pyridine (100 ml) and p-toluenesulfonylchloride (2.54 g, 7.49 mmol) dissolved in CH$_2$Cl$_2$ (25 mL) was added via dropping funnel. H$_2$O and CH$_2$Cl$_2$ (100 ml, 1:1) are added to the reaction mixture. The H$_2$O layer is separated and extracted with CH$_2$Cl$_2$ (3×50 mL). The CH$_2$Cl$_2$ extracts are pooled and dried (MgSO$_4$), filtered and concentrated in vacuo. The resulting residue is purified by silica gel flash column chromatography using EtOAc and hexanes with 1% triethyl amine as the eluent. The appropriate fractions are pooled and concentrated in vacuo to give title compound.

EXAMPLE 20
N-(2-Azidoethyl)-N-tritylsulfenyl-3-amino-1-O-dimethoxytritylpropanol N-[2-(O-p-Toluenesulfonyl)hydroxyethyl]-N-tritylsulfenyl-3-amino-1-O-dimethoxytritylpropanol (5.0 g, 6.1 mmol) is dissolved in DMF (100 ml) and cooled to 0° C. NaN$_3$ (0.44 g, 6.76 mmol) is added and the reaction mixture is heated to 40° C. in an oil bath. Upon completion of the reaction as shown by TLC, the reaction mixture is concentrated in vacuo and the residue is partitioned between EtOAc and H$_2$O (100 mL, 1:1). The H$_2$O layer is separated and extracted with EtOAc (3×50 ml). The EtOAc extracts are dried (MgSO$_4$), filtered and concentrated in vacuo. The resulting residue is purified by silica gel flash column chromatography using EtOAc and hexanes with 1% triethyl amine as the eluent. The appropriate fractions are pooled and concentrated in vacuo to give the title compound.

EXAMPLE 21
N-(2-Azidoethyl)-N-tritylsulfenyl-3-amino-1-propanol

N-(2-azidoethyl)-N-tritylsulfenyl-3-amino-1-O-dimethoxytritylpropanol (5.0 g, 6.93 mmol) is dissolved in a minimal amount of cold 80% glacial acetic acid. The reaction mixture is monitored by TLC to completion. The reaction mixture is partitioned between H$_2$O and EtOAc (100 mL, 1:1). The aqueous layer is separated and extracted with EtOAc (3×50 mL). The EtOAc extracts are dried (MgSO$_4$), filtered and concentrated in vacuo. The resulting residue is purified by silica gel flash column chromatography with EtoAc /CH$_2$Cl$_2$ as the eluent. The appropriate fractions are pooled and concentrated in vacuo to give the title compound.

EXAMPLE 22
N-(2-Azidoethyl)-N-tritylsulfenyl-3-amino-1-O-phthalimidopropanol N-(2-azidoethyl)-N-tritylsulfenyl-3-amino-1-propanol (5.0 g, 11.8 mmol) and N-hydroxyphthalimide (2.90 g, 17.8 mmol) are dissolved in distilled THF and the reaction flask is flushed with Argon. The reaction is cooled to 0° C. and diisopropylazodicarboxylate is added dropwise (slowly so the orange color created by the diisopropylazodicarboxylate dissipates before the next addition). The reaction mixture is allowed to warm up to room temperature overnight. The reaction mixture is concentrated in vacuo and the residue is partitioned between EtOAc and H$_2$O (100 ml, 1:1). The H$_2$O layer is separated and extracted with EtOAc (3×50 mL). The collected EtOAc fractions are dried (MgSO$_4$), filtered and concentrated in vacuo. The crude material is purified by silica gel flash column chromatography using EtOAc/ hexanes as the eluent. The appropriate fractions are pooled and concentrated in vacuo to give the title compound.

EXAMPLE 23
N-(2-Aminoethyl)-N-tritylsulfenyl-3-amino-1-O-phthalimidopropanol Bb (FIG. 1)

N-(2-azidoethyl)-N-tritylsulfenyl-3-amino-1-O-phthalimidopropanol (5.0 g, 8.8 mmol) is dissolved in THF (100 mL) and a catalytic amount of H$_2$O is added. Triphenylphosphine (2.54 g, 9.7 mmol) is added at room temperature and the reaction mixture is stirred for 5 hours. The reaction mixture is partitioned between EtOAc and H$_2$O (100 mL, 1:1). The H$_2$O layer is separated and extracted with EtOAc (3×50 mL). The EtOAc extracts are dried (MgSO$_4$), filtered and concentrated in vacuo. The residue is dissolved in CH$_2$Cl$_2$ (100 mL) and cooled to 0° C. Methylhydrazine (0.44 g, 9.7 mmol) is added to the reaction mixture. The reaction mixture is stirred and then concentrated in vacuo. The resulting residue is partitioned between EtOAc and H$_2$O (100 mL, 1:1). The H$_2$O layer is separated and extracted with EtOAc (3×50 mL). The EtOAc extracts are pooled, dried (MgSO$_4$), filtered and concentrated in vacuo. The resulting residue is purified by silica gel column chromatography using MeOH/CH$_2$Cl$_2$ as the eluent. The appropriate fractions are pooled and concentrated in vacuo to give the title compound.

EXAMPLE 24
N-(2-Hydroxyethyl)-3-amino-1-propanol

N-(2-hydroxyethyl)-3-amino-1-O-dimethyoxytritylpropanol (5 g, 11.86 mmol) is dissolved in 80% AcOH (100 mL). The reaction is stirred until complete, as indicated by TLC. The reaction mixture is concentrated in vacuo. The resulting residue is purified by silica gel flash column chromatography using MeOH/CH$_2$Cl$_2$ as the eluent. The appropriate fractions are pooled and concentrated in vacuo to give the title compound.

EXAMPLE 25
N-(2-Hydroxyethyl)-N-tritylsulfenyl-3-amino-1-propanol

N-(2-hydroxyethyl)-3-amino-1-propanol (5.0 g, 41.9 mmol) is coevaporated several times with pyridine (20 mL) and then dissolved in pyridine (100 mL). The reaction flask is flushed with Argon and trimethylsilylchloride (2.47 g, 209.5 mmol) is added dropwise. The reaction mixture is stirred for 1 hour. Triphenyl methanesulfenyl chloride (14.32 g, 46.09 mmol) is dissolved in CH$_2$Cl$_2$ and added via dropping funnel to the cooled reaction mixture. The reaction mixture is warmed to room temperature and stirred for 18 hours. The reaction mixture is concentrated in vacuo and the resultant residue is partitioned between H$_2$O and EtOAc (100 ml, 1:1). The H$_2$O layer is separated and extracted with EtOAc (3×50 ml). The EtOAc extracts are pooled, dried (MgSO$_4$) and filtered. The filtrate is concentrated in vacuo and the residue is purified by silica gel flash column chromatography with EtOAc/hexanes as the eluent. The appropriate fractions are pooled and concentrated in vacuo to give the title compound.

EXAMPLE 26
N-(2-p-Toluenesulfonylethyl)-N-tritylsulfenyl-3-amino-1-O-p-toluenesulfonylpropanol N-(2-hydroxyethyl)-N-tritylsulfenyl-3-amino-1-propanol (5.0 g, 12.64 mmol) is dissolved in pyridine (100 mL) and cooled to 0° C. p-Toluensufonylchloride (2.65 g, 13.9 mmol) is dissolve in CH$_2$Cl$_2$ (50 mL) and added to the reaction mixture at 0° C. via dropping funnel. The reaction is monitored by TLC to completion. The reaction mixture is concentrated in vacuo and the resultant residue is dissolved in EtOAc and washed with H$_2$O (3×50 mL) and brine (2×50 mL). The EtOAc is dried (MgSO$_4$), filtered and concentrated in vacuo. The residue is purified by silica gel column chromatography using EtOAc/hexanes as eluent. The appropriate fractions are pooled and concentrated in vacuo to give the title compound.

EXAMPLE 27
N-(2-O-p-Toluenesulfonylethyl)-N-tritylsulfenyl-3-amino-1-O-phthalimidopropanol, N-(2-O-phthalimidoethyl)-N-tritylsulfenyl-3-amino-1-p-toluenesulfonylpropanol N-(2-O-p-toluenesulfonylethyl)-N-tritylsulfenyl-3-amino-1-p-toluenesulfonylpropanol (5.0 g, 7.12 mmol), triphenylphosphine (2.05 g, 7.83 mmol) and N-hydroxyphthalimide (1.74 g, 10.68 mmol) are dissolved in dry THF under an atmosphere of argon. The reaction mixture is cooled to 0° C. and diisopropyl azodicarboxylate (1.89 g, 8.54 mmol) is added dropwise (slowly so the orange color created by the diisopropyl azodicarboxylate dissipates before the next addition). The reaction mixture is warmed up to room temperature and stirred for 18 hours. The reaction mixture is concentrated in vacuo and the residue partitioned between EtOAc and H$_2$O (100 mL, 1:1). The H$_2$O layer is separated and extracted with EtOAc (3×50 mL). The EtOAc extracts are dried (MgSO$_4$), filtered and concentrated in vacuo. The resultant residue is purified by silica gel flash column chromatography using EtOAc/hexanes as the eluent. The appropriate fractions are pooled and concentrated in vacuo to give both of the title compounds.

EXAMPLE 28
N-(2-Azidoethyl)-N-tritylsulfenyl-3-amino-1-O-phthalimidopropanol N-(2-o-p-toluenesulfonylethyl)-N-tritylsulfenyl-3-amino-1-O-phthalimidopropanol (5.0 g, 72.2 mmol) is dissolved in dry DMF (100 mL). NaN$_3$ (0.56 g, 8.66 mmol) is added to the reaction mixture. The reaction is warmed up to 40° C. The reaction is monitored by TLC. The reaction mixture is concentrated in vacuo and the residue partitioned between EtOAc and H$_2$O (100 mL, 1:1). The H$_2$O layer is separated and extracted with EtOAc (3×50 mL). The collected EtOAc fractions are dried (MgSO$_4$), filtered and concentrated in vacuo. The resultant residue is purified by silica gel flash column chromatography using EtOAc/hexanes as the eluent. The appropriate fractions are pooled and concentrated in vacuo to give the title compound.

EXAMPLE 29
N1-[(t-Boc)-O-amino-3-propanol-1-yl]diaminoethane

N-(2-azidoethyl)-N-tritylsulfenyl-3-amino-1-O-phthalimidopropanol (5 g, 9.03 mmol) is dissolved in THF (100 mL) and a catalytic amount of H$_2$O is added to the reaction mixture. Triphenylphosphine (2.6 g, 9.93 mmol) is added at room temperature and the reaction mixture is stirred. The reaction is monitored by TLC. The reaction mixture is concentrated in vacuo and the residue partitioned between EtOAc and H$_2$O (100 mL, 1:1). The H$_2$O layer is separated and extracted with EtOAc (3×50 mL). The EtOAc extracts are dried (MgSO$_4$), filtered and concentrated in vacuo. The residue is dissolved in CH$_2$Cl$_2$ (100 mL) and cooled to 0° C. Methylhydrazine (0.42 g, 9.03 mmol) is added and upon completion as indicated by TLC, the reaction mixture is concentrated in vacuo and the residue partitioned between EtOAc and H$_2$O (100 ml, 1:1). The H$_2$O layer is separated and extracted with EtOAc (3×50 mL). The EtOAc extracts are dried (MgSO$_4$), filtered and the filtrate concentrated in vacuo. The resulting residue is purified by silica gel flash column chromatography using MeOH/CH$_2$Cl$_2$ as the eluent. The appropriate fractions are pooled and concentrated in vacuo to give the title compound.

EXAMPLE 30
N-(2-O-Phthalimidoethyl)-N-tritylsulfenyl-3-amino-1-azidopropane

N-(2-O-phthalimidoethyl)-N-tritylsulfenyl-3-amino-1-p-toluenesulfonylpropanol (5.0 g, 9.51 mmol) is dissolved in dry DMF (100 mL). NaN$_3$ (0.74 g, 11.41 mmol) is added to the reaction mixture. The reaction mixture is warmed up to 40° C. The reaction progress is monitored by TLC. The reaction mixture is concentrated in vacuo and the residue partitioned between EtOAc and H$_2$O (100 mL, 1:1). The H$_2$O layer is separated and extracted with EtOAc (3×50 mL). The EtOAc extracts are dried (MgSO$_4$), filtered and concentrated in vacuo. The resultant residue is purified by silica gel flash column chromatography using EtOAc/ hexanes as the eluent. The appropriate fractions are pooled and concentrated in vacuo to give the title compound.

EXAMPLE 31
N-(2-O-aminoethyl)-N-tritylsulfenyl-1,3-diaminopropane

N-(2-O-phthalimidoethyl)-N-tritylsulfenyl-3-amino-1-azidopropane (5.0 g, 9.03 mmol) is dissolved in THF (100 mL) and a catalytic amount of $H_2O$ is added to the reaction mixture. Triphenylphosphine (2.61 g, 9.93 mmol) is added at room temperature and the reaction mixture is allowed to stir. Reaction progress is monitored by TLC. The reaction mixture is concentrated in vacuo and the residue partitioned between EtOAc and $H_2O$ (100 ml, 1:1). The $H_2O$ layer is separated and extracted with EtOAc (3×50 mL). The EtOAc extracts are dried ($MgSO_4$), filtered and concentrated in vacuo. The residue is dissolved in $CH_2Cl_2$ (100 mL) and cooled to 0° C. Methylhydrazine (0.46 g, 9.93 mmol) is added to the reaction mixture drop wise. The reaction mixture is stirred until complete by TLC. The reaction mixture is concentrated in vacuo and the residue partitioned between EtOAc and $H_2O$ (100 mL, 1:1). The $H_2O$ layer is separated and extracted with EtOAc (3×50 mL). The EtOAc extracts are dried ($MgSO_4$), filtered and concentrated in vacuo. The resultant residue is purified by silica gel column chromatography using $MeOH/CH_2Cl_2$ as the eluent. The appropriate fractions are pooled and concentrated in vacuo to give the title compound.

EXAMPLE 32
3-Azido-1-propanol 3-chloro-1-propanol (10 mL, 120 mmol) and sodium azide (8.6 g, 132 mmol) were stirred in DMF (400 mL) with heating to about 60° C. for about 16 hours. The reaction mixture was cooled to room temperature and ethyl ether ( 800 mL) was added. The mixture was stirred for about 15 minutes and water (~1 L) was added. The ethyl ether layer was separated and dried over $Na_2SO_4$. The ether layer was filtered and the filtrate evaporated in vacuo to give about 8.7 g (71.4%) of the title compound. TLC (Rf: 0.3; 20% EtOAc/Hexane, $I_2$). $^1H$ NMR ($CDCl_3$) δ 1.8 (s, 2H, $CH_2$), 2.1 (m, 2H, $CH_2$), 3.5 (t, 2H, $CH_2$), 3.8 (t, 2H, $CH_2$).

EXAMPLE 33
2-(3-azidopropoxy)-4,6-diallyloxy-s-triazine

To 3-azido-1-propanol (8.7 g, 85.7 mmol) in THF (200 mL) was added sodium hydride (5.6 g, 128.6 mmol) at −78° C. The reaction mixture was stirred at −78° C. for about 30 minutes and then allowed to equilibrate at room temperature and stirred for an additional 3 hours. The reaction mixture was recooled to −78° C. and added to a solution of 2,4,6-triallyloxy-1,3,5-triazine (21.4 g, 85.7 mmole) in THF (200 mL). The reaction mixture was stirred at room temperature for about 16 hours. The reaction mixture was evaporated to a brown residue. The residue was purified by flash column chromatography over silica gel using EtOAc/hexane as the eluent. The pure fractions were pooled together and evaporated to dryness to give 8.5 g (36%) of the title compound. TLC (Rf: 0.5; 20% EtOAc/Hexane, $I_2$). $^1H$ NMR ($CDCl_3$) δ 2.1 (m, 2H, $CH_2$), 3.5 (t, 2H, $CH_2$), 4.5 (t, 2H, $CH_2$), 4.9 (m, 4H, $CH_2$), 4.3 (m. 4H, $CH_2$), 6.0 (m, 2H, CH).

EXAMPLE 34
2-(3-azidopropoxy)-4,6-dioxyacetaldehydo-s-triazine

To 2-(3-azidopropoxy)-4,6-diallyloxy-s-triazine (1.16 g, 4.0 mmol), THF (100 mL) and osmium tetroxide (20.4 mL, 3.2 mmole, 4%, aq) is added sodium periodate (8.6 g, 40 mmole). The reaction mixture is stirred at room temperature overnight and about 20 mL of water is added. The aqueous solution is then extracted several times with EtOAc. Sodium chloride is added to the aqueous layer the resulting mixture is extracted with EtOAc. The EtOAc extracts are combined, dried ($Na_2SO_4$), filtered, and concentrated in vacuo. The resulting residue is purified by silica gel flash column chromatography to give the title compound.

EXAMPLE 35
2,4,6-tris(dibromomethyl)-s-triazine

HCL (gas) was bubbled into dibromoacetonitrile (17.3 mL, 0.2 mol) and aluminum bromide (10.7 g, 0.4 mol) for 5 hours. The reaction mixture was held at 0° C. for 3 days. The reaction mixture was heated to 50° C. for 15 minutes, cooled to room temperature and treated with absolute ETOH. The resultant solid was filtered and washed with ETOH. The solid was then washed with $CHCl_3$ and the combined $CHCl_3$ layers were concentrated in vacuo to a solid. The solid was crystallized from ETOH to give the title compound 44 g (37%) (mp 130–131° C.). $^{13}C$ NMR ($CDCl_3$) δ 37.45, 176.57.

EXAMPLE 36
2-Amino-4,6-bis(dibromomethyl)-s-triazine

Concentrated $NH_4OH$ (250 mL) was added at room temperature to a solution of 2,4,6-tris(dibromoethyl)-triazine (15 g, 23.3 mmol) in EtOH (500 mL). The reaction mixture was stirred for 15 minutes and $H_2O$ (3000 mL) was added. The reaction mixture was filtered and the resulting solid was recrystallized to give the title compound 3.5 g (32%) (mp 171–173° C.). $^1H$ NMR (DMSO) δ 6.86 (s, 2H, CH), 8.44 (s, 2H, $NH_2$).

EXAMPLE 37
2,4-bis(dibromomethyl)-6-methyl-s-triazine

A solution of tris(dibromomethyl)triazine (1.5 g, 2.5 mmol) in acetone (10 mL) was added at room temperature to a stirred mixture of sodium iodide (15 g, 0.1 mol) in glacial acetic acid (5 mL) and acetone (50 mL). The resulting reaction mixture was stirred at room temperature for 6 min and poured into a solution of sodium bisulfite ($NaHSO_3$, 2 g) in ice water (100 mL). The mixture was extracted 4 times with diethylether, dried ($Na_2SO_4$), and filtered. The solvent was evaporated and the residue was purified by flash chromatography on a silica gel column (15 cm×3 cm). Elution with hexanes:chloroform (1:1, v/v) afforded 0.46 g (42%) of the title compound as a white solid.

TLC: Rf 0.51; hexanes:chloroform; 1:1, v/v; silica gel. $^1H$ NMR ($CDCl_3$) δ 2.80 (s, 3H), 6.49 (s, 2H).

EXAMPLE 38
6-Methyl-2,4-bis(dimorpholinomethyl)-s-triazine

A mixture of 2-methyl-4,6-Bis-(dibromomethyl)-s-triazine (0.4 g, 0.91 mmol) and morpholine (8 mL) was stirred at room temperature for 2 days and then heated to 70–80° C. and stirred for an additional 2 hours. The precipitate was filtered and the filtrate was evaporated under reduced pressure to remove the excess morpholine. The solid residue was recrystallized from ethyl acetate giving 0.40 g (95%) of the title compound as big cubic colorless crystals.

$^1H$ NMR ($CDCl_3$) δ 2.40–2.54 (m, 8H), 2.56–2.68 (m, 8H), 2.74 (s, 3H), 3.65–3.76 (m, 16H), 3.92 (s, 2H).

EXAMPLE 39
Diethyl pyrrole-3,4-dicarboxylate

Tosylmethyl isocyanide (9.8 g, 50 mmol), diethyl fumarate (8.2 mL, 50 mmol) and dry THF (1000 mL) were added dropwise to a stirred suspension of potassium t-butoxide (11.2 g, 100 mmol) and THF (150 mL). The mixture was stirred for 2 hours, saturated NaCl (500 mL) was added, and the mixture was extracted with THF (2×250 mL). The organic layers were dried ($Na_2SO_4$), filtered and concentrated in vacuo to give a solid. The solid was recrystallized from MeOH to give the title compound 4.6 g (44%) (mp 148–149° C.). $^1$H NMR (DMSO) δ 1.22 (t, 3H, $CH_3$), 4.18 (q, 2H, $CH_2$), 7.39 (s, 2H, ArH), 11.8 (bs, 1H, NH).

EXAMPLE 40
1-N-Propylphthalimido-1H-pyrrole-3,4-dicarboxylate diethyl ester

A solution of diethyl pyrrole-3,4-dicarboxylate (39 g, 0.185 mol) in THF (1600 mL) was treated with NaH (60%, 7.6 g, 0.19 mol). The reaction mixture was heated to reflux for 1 hour. The reaction was then cooled to 30° C. and N-(3-bromopropyl)phthalimide (52 g, 0.19 mol) was added. The reaction mixture was heated to reflux for 1 hour, cooled, filtered, and concentrated in vacuo. The resultant gum was partitioned between ETOAC/$H_2O$ and extracted with EtOAC (2×300 mL). The organic layer was dried ($MgSO_4$), filtered and concentrated in vacuo. The resultant solid was recrystallized from EtOAC to give the title compound 68 g (92%) (mp 100–101° C.). $^1$H NMR (DMSO) δ 1.24 (t, 3H, CH), 2.06 (m, 2H, $CH_3$), 3.57 (t, 2H, $CH_2$), 4.14 (m, 4H, $CH_2$), 7.49 (s, 2H, ArH), 7.86 (m, 4H, ArH).

EXAMPLE 41
1-N-Propylphthalimido-3,4-diformylpyrrole

1-N-Propylphthalimido-1H-pyrrole-3,4-dicarboxylate diethyl ester is treated as per the procedures illustrated in Trofimenko, S,. *J. Org. Chem.*, 1964, 29, 3046, with diisobutylaluminum hydride in dry benzene to afford the title compound.

EXAMPLE 42
1-Propylphthalimido-4,5-dicyanoimidazole

A solution of 4,5-dicyanoimidazole (24.8 g, 0.2 mol) in DMF (500 mL) was treated with NaH (60%, 8.0 g, 0.2 mol) with the temperature maintained below 40° C. The reaction mixture was then stirred at 35° C. for 1 hour. N-(3-bromopropyl)-phthalimide (53.6 g, 0.2 mol) was added and the reaction mixture was stirred for 48 hours at 40° C. The reaction mixture was concentrated in vacuo to a gum and crystallized from EtOAC to give the title compound 33 g (54%) (mp 134–135° C.). $^1$H NMR (DMSO) δ 2.21 (m, 2H, $CH_2$), 3.61 (m, 2H, $CH_2$), 4.30 (m, 2H, $CH_2$), 7.88 (m, 4H, ArH), 8.36 (s, 1H, ArH).

EXAMPLE 43
1-Propylphthalimido-4,5-diformylimidazole

1-Propylphthalimido-4,5-dicyanoimidazole is treated as per the procedures illustrated in Trofimenko, S,. *J. Org. Chem.*, 1964, 29, 3046, with diisobutylaluminum hydride in dry benzene to afford the title compound.

EXAMPLE 44
Diethyl-4-bromo-2,6-pyridinedicarboxylate

To chelidamic acid (2.29 g, 11.38 mmol) was added phosphorus pentabromide (14.7 g, 34.14 mmol), and the mixture was stirred. The reaction mixture was heated to 90° C. for 3 hours. The reaction mixture was cooled and $CHCl_3$ (350 mL) was added and the mixture was filtered. To the filtrate was added absolute ethanol (350 mL), and the mixture was stirred for 2 hours. The volume of the reaction mixture was reduced to approximately 35 mL. The title compound was purified by crystallization upon sitting overnight to give, after a second crop of crystals and purification by silica gel flash column chromatography a yield of 72% (m. p. 95–96° C.). $^1$H NMR ($CDCl_3$) δ 1.49 (t, 6H, 2x $CH_3$), 4.44 (q, 4H, 2x $CH_2$), 8.39 (s, 2H, 2x Ar). $^{13}$C NMR ($CDCL_3$) δ 14.19 ($CH_3$), 62.68 ($CH_2$), 131.02 (Ar), 134.87 (quaternary-Ar), 149.54 (quaternary-Ar), 163.51 (CO).

EXAMPLE 45
Diethyl-4-(3-azidopropoxy)-2,6-pyridinedicarboxylate
METHOD A

3-Azido-1-propanol (0.266 mL, 3.64 mmol) was dissolved in DMF (5 mL) and cooled to 0° C. NaH (146 mg, 3.64 mmol) was added and the mixture was stirred for 15 minutes. Diethyl-4-bromo-2,6-pyridinedicarboxylate was dissolved in DMF (5 mL) an added to the reaction mixture dropwise. The reaction was complete as indicated by TLC in 1 hour. The reaction mixture was partitioned between $CH_2Cl_2$ and water. The water was separated and extracted with $CH_2Cl_2$. The $CH_2Cl_2$ layers were combined, dried ($MgSO_4$) and concentrated to an oil. The oil was purified by silica gel flash column chromatography to give a yield of 40%. $^1$H NMR ($CDCl_3$) δ 1.44 (t, 6H, 2x $CH_2$), 2.11 (m, 2H, $CH_2$), 3.54 (t, 2H, $CH_2$), 4.23 (t, 2H, $CH_2$), 4.45 (q, 4H, 2x $CH_2$), 7.78 (2, 2H, 2x Ar).
METHOD B Sodium hydride (2.8 g, 60% in mineral oil) was added to a stirred solution of 3-azido-1-propanol (5.6 g, 55 mmol) in THF (120 mL). The stirring was continued for 20 min. A solution of diethyl 4-bromopyridine-2,6-dicarboxylate (15 g, 49 mmol) in THF (120 mL) was added dropwise at room temperature to the above stirred mixture. The resulting reaction mixture was stirred at room temperature for 1.5 hours and poured onto ice water (800 mL). The solution was extracted with ethyl acetate. The combined organic extracts were washed with brine, dried ($Na_2SO_4$), and filtered. The solvent was evaporated under reduced pressure and the residue was purified by flash chromatography on a silica gel column (15 cm×5 cm). Elution with hexanes:ethyl acetate (5:1 and 2:1, v/v) afforded 11.3 g (72%) of the title compound as a pale yellow oil.

TLC: Rf 0.42; hexanes:ethyl acetate; 1:1, v/v; silica gel. $^1$H NMR ($CDCl_3$) δ 1.44 (t, 6 H, J=7.0 Hz), 2.02–2.18 (m, 2H), 3.54 (t, 2H, J=6.0 Hz), 4.22 (t, 2H, J=6.0 Hz), 4.46 (q, 4H, J=7.0 Hz), 7.77 (s, 2H).

EXAMPLE 46
4-(3-Azidopropoxy)-2,6-dihydroxymethylpyridine

To a stirred solution of Diethyl-4-(3-azidopropoxy)-2,6-pyridinedicarboxylate (4.2 mmol) in dichloromethane (10 mL) and absolute ethanol (15 mL), was added in portions, $NaBH_4$ (4.2 mmol) at 25° C. Powdered $CaCl_2$ (4.2 mmol) was added cautiously in small portions and the evolution of hydrogen was allowed to cease before each further addition. The reaction mixture was stirred for 2 hours. Water (100 mL) was added and the reaction mixture was extracted several times with ethyl acetate. The ethyl acetate layers were combined, dried ($MgSO_4$) and concentrated in vacuo. The resultant residue was purified by silica gel flash column chromatography to give the title compound. $^1$H NMR (DMSO) δ 2.00 (m, 2H, $CH_2$), 3.52 (t, 2H, $CH_2$), 4.13 (t, 2H, $CH_2$), 4.45 (d, 4H, 2x $CH_2$), 5.36 (t, 2H, 2x OH), 6.87 (s, 2H, 2x AR).

EXAMPLE 47
4-(Azidopropoxy)-2,6-diformyl-pyridine

DMSO (1.21 mL, 17.1 mmol) was diluted with $CH_2Cl_2$ (approximately 25 mL) and cooled to −78° C. Oxalyl chloride (0.745 mL, 8.45 mmol) was added dropwise and the reaction mixture was stirred for 15 minutes. 4-(3- azidopropoxy)-2,6-dihydroxymethylpyridine (1 g, 4.27 mmol) dissolved in $CH_2Cl_2$ (10 mL) was added slowly to the cooled reaction mixture. After 0.5 hour triethylamine (2.77 mL, 19.70 mmol) was added dropwise to the reaction mixture. The dry ice/acetone bath was removed and the reaction mixture was warmed to room temperature for approximately 40 minutes. The reaction mixture was partitioned between $CH_2Cl_2$ and water and extracted several times with $CH_2Cl_2$. The $CH_2Cl_2$ layers were combined, dried ($MgSO_4$) and concentrated in vacuo. The resulting residue was purified by silica gel flash column chromatography to give the title compound. $^1H$ NMR (DMSO) δ 2.02 (m, 2H, $CH_2$), 3.52 (t, 2H, $CH_2$), 4.31 (t, 2H, $CH_2$), 7.64 (s, 2H, 2x Ar), 10.01 (s ,2H, CHO). $^{13}C$ NMR (DMSO) δ 27.61 ($CH_2$), 47.40 ($CH_2$), 66.22 ($CH_2$), 111.58 (Ar), 154.40 (quaternary, Ar), 166,50 (quaternary, Ar), 192.44 (CHO).

EXAMPLE 48

(7-(N-Tritylsulfenyl)-2,7,10-triaza-3-oxaundecane)[11](2,6) pyridinophane

N-(2-Aminoethyl)-N-tritylsulfenyl-3-amino-1-(-O-amino)-propane, 4-(azidopropoxy)-pyridine-2,6-dialdehyde and $MgCl_2$ in equimolar amounts (0.025 molar) are dissolved in dry MeOH. The reaction mixture is stirred at room temperature for 1 hour and at reflux temperature for 2.5 hours. The reaction mixture is cooled to 0° C. and $NaBH_3CN$ (50 eq.) is added and the reaction mixture is stirred at 0° C. for 1.5 hours and then at room temperature for 16 hours. The reaction mixture is concentrated in vacuo and the residue left behind is partitioned between EtOAc and $H_2O$ (100 mL, 1:1). The $H_2O$ layer is separated and extracted with EtOAc (3×50 mL). The EtOAc extracts are dried ($MgSO_4$), filtered and the filtrate is concentrated in vacuo. The resulting residue is purified by silica gel flash column chromatography using $MeOH/CH_2Cl_2$ as the eluent. The appropriate fractions are pooled and concentrated in vacuo to give the title compound.

EXAMPLE 49

Bis-1,3-(2-hydroxyethyl)-5-(2-p-toluensulfenylethyl) cyanuric acid

Tris-1,3,5-(2-hydroxyethyl)-cyanuric acid (10 g, 38.3 mmol) was dissolved in dry pyridine (700 mL). The reaction mixture was cooled in an ice bath, p-toluensulfenylchloride (4.83 g, 23.0 mmol) dissolved in $CH_2Cl_2$ (25 mL) was added dropwise to the above mixture and was stirred for 18 hours. The solvent was reduced to a volume of approximately 30 mL and partitioned between $CH_2Cl_2$ and water. The $CH_2Cl_2$ layer was collected and dried ($MgSO_4$), filtered and concentrated to a yellow oil: The oil was purified by silica gel flash column chromatography to give a 60% yield of the title compound. $^1H$ NMR (DMSO) δ 2.40 (s, 3H, Tosyl-$CH_3$), 3.49 (t, 4H, 2x $CH_2$), 3.72 (t, 4H, 2x $CH_2$), 4.00 (t, 2H, $CH_2$), 4.24 (t, 2H, $CH_2$), 4.79 (bs, 2H, 2x OH), 7.41 (d, 2H, Tosyl-Ar), 7.70 (d, 2H, Tosyl-Ar). $^{13}C$ NMR (DMSO) δ 21.14 ($CH_3$), 40.91 ($CH_2$), 44.29 ($CH_2$), 57,44 ($CH_2$), 66.89 ($CH_2$), 127.47 ( Tosyl-Ar), 130.14 (Tosyl-Ar), 132.09 (Tosyl-Ar), 145.11 (Tosyl-Ar), 148.66 (CO).

EXAMPLE 50

Bis-1,3-(2-hydroxyethyl)-5-(2-azidoethyl) cyanuric acid

Bis-1,3-(2-hydroxyethyl)-5-(2-p-toluensulfenylethyl) cyanuric acid (4.63 g, 11.15 mmol) was dissolved in DMF (150 mL). sodium azide (1.09 g, 16.72 mmol) was added in one portion and the reaction mixture was stirred overnight. The solvent was removed and the residue partitioned between $CH_2Cl_2$/water, the water was extracted 10 times with $CH_2Cl_2$ and the $CH_2Cl_2$ extracts were combined, dried ($MgSO_4$) and concentrated to a yellow oil. The oil was purified by silica gel flash column chromatography to give the title compound in a yield of 91%. $^1H$ NMR (DMSO) δ 3.54 (m, 6H, 3x $CH_2$), 3.86 (t, 4H, 2x $CH_2$), 3.99 (t, 2H, $CH_2$), 4.80 (t, 2H, 2x OH). $^{13}C$ NMR ($CDCl_3$) δ 41.45 ($CH_2$), 45.08 ($CH_2$), 48.36 ($CH_2$), 49.87 ($CH_2$), 149.20 (CO).

EXAMPLE 51

1,3-(Acetaldehydo)-5-(2-azidoethyl) cyanuric acid

Dry DMSO (0.390 mL, 5.49 mmol) and dry $CH_2Cl_2$ (20 mL) are cooled to −78° C. and oxalyl chloride (0.240 mL, 2.75 mmol) was added slowly with stirring for 10 minutes. Bis-1,3-(2-hydroxyethyl)-5-(2-azidoethyl) cyanuric acid (0.263 mg, 1.37 mmol) was dissolved in dry $CH_2Cl_2$ and added to the reaction mixture. The reaction was stirred at −78° C. for 0.5 hour before triethylamine (0.881 mL, 6.32 mmol) was added dropwise and the reaction mixture was warmed to room temperature. The reaction mixture was partitioned between water and $CH_2Cl_2$. The $CH_2Cl_2$ layer was separated, dried ($MgSO_4$), filtered and concentrated in vacuo. The resulting oil was purified by silica gel column chromatography to yield 75% of the title compound. $^1H$ NMR (DMSO) δ 3.55 (t, 2H, $CH_2$), 4.00 (t, 2H, $CH_2$), 4.74 (s, 4H, 2x $CH_2$), 9.58 (s, 1H, CHO).

EXAMPLE 52

2,4,6-Triethoxycarbonyl-1,3,5-triazine

Hydrogen chloride gas was bubbled through neat ethyl-cyanoformate (0.997 ml, 10.1 mmol) until the solution became a white solid, approximately 2 hours. The solid was partitioned between $CH_2Cl_2$ and water. The $CH_2Cl_2$ layer was collected dried ($MgSO_4$) and concentrated to a white solid. The product was crystallized from hot absolute ethanol to give the title compound (m. p. 169–170° C.). $^1H$ NMR ($CDCl_3$) δ 1.42 (t, 9H, 3x $CH_3$), 4.50 (q, 6H, 3x $CH_2$). $^{13}C$ NMR (DMSO) δ 14.06 ($CH_3$), 64.02 ($CH_2$), 161.27 (CO), 166.86 (Triazine Ar).

EXAMPLE 53

2,4,6-Trihydroxymethyl-s-triazine 2,4,6-Triethoxycarbonyl-s-triazine (1 g, 3.36 mmol) is dissolved in dichloromethane (15 mL) and absolute ethanol (25 mL) then cooled to 0° C. before sodium borohydride (127 mg, 3.36 mmol) is added. After 15 minutes calcium chloride (373 mg, 2.97 mmol) is added and the reaction mixture is warmed to room temperature. The reaction mixture is dried to a yellow solid and subjected to soxhlet extraction with ethanol. The ethanol is evaporated to a white solid. The product is crystallized from Methanol and water or purified by silica gel flash column chromatography to give the title compound.

EXAMPLE 54

4-(p-Toluenesulfonylmethyl)-2,6-dihydroxymethyl-s-triazine 2,4,6-Trihydroxymethyl-s-triazine (1 eq.) is dissolved in an excess of pyridine. p-Toluenesulfonylchloride (0.6 eq.) in $CH_2Cl_2$ is added and the reaction mixture is stirred overnight. The solvent volume is reduced to a slurry to which water and dichloromethane are added and the resulting mixture is extracted with $CH_2Cl_2$. The combined $CH_2Cl_2$ layers are dried ($MgSO_4$) and concentrated to an oil. The oil is purified by silica gel flash column chromatography to give the title compound.

EXAMPLE 55

4-(Azidomethyl)-2,6-dialdehyde-s-triazine (via 4-(azidomethyl)-2,6-dihydroxymethyl-s-triazine) (9)

4-(p-Toluenesulfonylmethyl)-2,6-dihydroxymethyl-s-triazine is dissolved in DMF and sodium azide (1.1 eq.) is added. The reaction mixture is heated to 50° C. for 4 hours. The DMF is removed under reduced pressure and the residue is partitioned between $CH_2Cl_2$ and water. The $CH_2Cl_2$ layer is separated and the water layer is extracted several times with $CH_2Cl_2$. The $CH_2Cl_2$ layers are combined, dried ($MgSO_4$), and concentrated. The resultant residue is purified by silica gel flash column chromatography to give 4-(azidomethyl)-2,6-dihydroxymethyl-s-triazine.

DMSO is diluted with $CH_2Cl_2$ and cooled to −78° C. Oxalyl chloride is added slowly and allowed to stir for 0.5 hours. The 4-(azidomethyl)-2,6-dihydroxymethyl-s-triazine dissolved in $CH_2Cl_2$ is added slowly to the reaction mixture. After 1 hour, triethylamine is added dropwise and the reaction is allowed to warm up to room temperature. The reaction mixture is diluted with water and $CH_2Cl_2$. The $CH_2Cl_2$ layer is separated and the water layer is extracted several times with $CH_2Cl_2$. The $CH_2Cl_2$ layers are combined, dried ($MgSO_4$), and concentrated. The resultant oil is purified by silica gel flash column chromatography to give the title compound.

EXAMPLE 56

(7-(N-Tritylsulfenyl)-2,7,10-triaza-3-oxaundecane)[11](2,6)-4- azidoethoxy-s-triazinophane 10b (FIG. 1)

N-(2-aminoethyl)-N-tritylsulfenyl-3-amino-1-(-O-amino)-propanol, 4-(azidomethyl)-2,6-dialdehyde-s-triazine (9) and $NiCl_2$ in equimolar amounts (0.025 molar) are dissolved in dry MeOH. The reaction mixture is stirred at room temperature for 1 hour and at reflux temperature for 5 hours. The reaction mixture is cooled to 0° C. and $NaBH_3CN$ (10 eq.) is added and the reaction mixture is stirred at 0° C. for 1.5 hours and then at room temperature for 16 hours. The reaction mixture is concentrated in vacuo and the residue left behind is partitioned between EtOAc and $H_2O$ (100 mL, 1:1). The $H_2O$ layer is separated and extracted with EtOAc (3×50 mL). The EtOAc extracts are dried ($MgSO_4$), filtered and the filtrate is concentrated in vacuo. The resulting residue is purified by silica gel flash column chromatography using MeOH/30% ammonium hydroxide (100:1, v/v) as the eluent. The appropriate fractions are pooled and concentrated in vacuo to give the title compound.

EXAMPLES 57–61

Synthesis of first round library (polyaza triazinophane 14 a,b,c,d) from (7-(N-tritylsulfenyl)-2,7,10-triaza-3-oxaundecane) [11](2,6)-4-azidoethoxy-s-triazinophane 10b ($R=SC(Ph)_3$) and four letters (benzaldehyde, Aldrich-B133-4 [$L_1$]; m-tolualdehyde, Aldrich-T3,550-5 [$L_2$]; m-anisaldehyde, Aldrich-12,965-8 [$L_3$]; and 3-nitrobenzaldehyde, Aldrich-N1,084-5 [$L_4$]. (FIG. 2)

EXAMPLE 57

Step A
Method 1

(7-(N-Tritylsulfenyl)-2,7,10-triaza-3-oxaundecane)- [11] (2,6)-4-azidoethoxy-s-triazinophane 10b (200 mmol) is divided into four equal parts and each is reacted separately with benzaldehyde ($L_1$), m-tolualdehyde ($L_2$), m-anisaldehyde ($L_3$), or 3-nitrobenzaldehyde ($L_4$). The reactants can be dissolved in a variety of organic solvents such as dichloromethane, dichloroethane, ethyl acetate, toluene, or methanol. 1.5 to 3 equivalents of the aldehyde is employed with 1 to 3% glacial acetic acid added as a catalyst. Reactions are allowed to proceed from 5 to 24 hours then treated directly with $NaCNBH_3$ (2–3 equivalents) . The reduction reaction mixtures should be stirred at room temperature for 1 to 10 hours, filtered, adjusted to neutrality and evaporated to dryness under reduced pressure. The residues are partitioned between ethyl acetate and aqueous $NaHCO_3$. The organic layer is separated, dried ($MgSO_4$) and filtered and the filtrate evaporated to dryness under reduced pressure. The individual residues can be purified by column chromatography if needed. A sample of each pure cyclophane like compound 11 a,b,c,d is saved for use in Example 69 (Fourth Round). Equal molar amounts of each of the four cyclophane like compounds are mixed to provide cyclophane like compound 11 with position 1 combinatorialized with the four selected aromatic aldehydes (reductive alkylation provides benzyl moieties).

Method 2

(7-(N-Tritylsulfenyl)-2,7,10-triaza-3-oxaundecane)- [11] (2,6)-4-azidoethoxy-s-triazinophane 10b (200 mmol) is reacted sequentially, in one pot, with benzaldehyde ($L_1$), m-tolualdehyde ($L_2$), m-anisaldehyde ($L_3$), and 3-nitrobenzaldehyde ($L_4$). The reactants can be dissolved in a variety of organic solvents such as dichloromethane, dichloroethane, ethyl acetate, toluene, or methanol. 50 mmol $L_1$, 50 mmol $L_2$, 50 mmol $L_3$, and 100 mmol $L_4$ are added sequentially to a solution of 10b with 1 to 3% glacial acetic acid included as a catalyst. Reactions are allowed to proceed from 5 to 24 hours then the one-pot is treated directly with $NaCNBH_3$ (2–3 equivalents). The reduction reaction is stirred at room temperature for 1 to 10 hours, filtered, adjusted to neutrality and evaporated to dryness under reduced pressure. The residue is partitioned between ethyl acetate and aqueous $NaHCO_3$. The organic layer is separated, dried ($MgSO_4$), filtered, and evaporated to dryness under reduced pressure. The residue can be purified by column chromatography if needed. This form of one-pot sequential addition of letters provides the cyclophane like compound 11 with position 1 combinatorialized with the four selected aromatic aldehydes (reductive alkylation provides benzyl moieties).

Method 3

(7-(N-Tritylsulfenyl)-2,7,10-triaza-3-oxaundecane)- [11] (2,6)-4-azidoethoxy-s-triazinophane 10b (200 mmol) is reacted in one pot, with one solution of benzaldehyde ($L_1$), m-tolualdehyde ($L_2$), m-anisaldehyde ($L_3$), or 3-nitrobenzaldehyde ($L_4$). The reactants can be dissolved in a variety of organic solvents such as dichloromethane, dichloroethane, ethyl acetate, toluene, or methanol. A solution of 50 mmol $L_1$, 50 mmol $L_2$, 50 mmol $L_3$, and 50 mmol $L_4$ were added simultaneously to a solution of 10b with 1 to 3% glacial acetic acid included as a catalyst. The reaction is allowed to proceed from 5 to 24 hours and treated directly with $NaCNBH_3$ (2–3 equivalents). The reduction reaction is stirred at room temperature for 1 to 10 hours, filtered, adjusted to neutrality and evaporated to dryness under reduced pressure. The residue is partitioned between ethyl acetate and aqueous $NaHCO_3$. The organic layer is separated, dried ($MgSO_4$), filtered, and evaporated to dryness under reduced pressure. The residue can be purified by column chromatography if needed. The simultaneous addition of letters provides the cyclophane like compound 11 with position 1 combinatorialized with the four selected aromatic aldehydes (reductive alkylation provides benzyl moieties).

EXAMPLE 58

Step B (FIG. 2)

Repeat Example 57, Step A, utilizing Method 1, 2, or 3 applied to the cyclophane like compound 11. This will provide the cyclophane like compound 12 with positions 1 and 2 combinatorialized with benzyl moieties. A portion of this material is retained for use in Example 69 (Fourth Round).

EXAMPLE 59

Step C (FIG. 2)

The cyclophane like compound 12 (200 mmol) in ethyl acetate is treated with 0.1 N HCl for 5 to 12 hours, adjusted to neutrality, and evaporated to dryness to provide a residue containing the deprotected cyclophane like compound 13. This material can be purified by column chromatography. A portion of this material is retained for use in Example 62 (Second Round). Repeat the procedure of Example 57, Step A, for the remaining residue, by utilizing Method 1, 2, or 3, to convert cyclophane like compound 12 to cyclophane like compound 13. Cyclophane like compound 13 has positions 1, 2, and 3 combinatorialized with benzyl moieties.

EXAMPLE 60

Step D (FIG. 2)

Cyclophane like compound 13 (200 mmol), is stirred in THF (800 mL), $H_2O$ (3.0 mL) and triphenyl phosphine (232 mmol). The reaction mixture is stirred at 50–80° C. for 12–24 hours under an atmosphere of argon. The reaction mixture is evaporated and the residue is dissolved in 800 mL of 0.5 M $NaH_2PO_4$ solution. The mixture is extracted with EtOAc. The aqueous layer is treated with 3 N NaOH until neutral and then extracted with ether. The $NaSO_4$-dried ether layer is evaporated to provide the amino ethoxy derivative of cyclophane like compound 13. This material is reacted as described in Example 57, utilizing Method 1, (separation of 13 into four equal parts) to provide cyclophane like compound 14 in four equal parts a, b, c and d. These materials (libraries) are utilized in various screening procedures.

EXAMPLE 61

Step E
Method 4 (FIG. 2)

(7-(N-Tritylsulfenyl)-2,7,10-triaza-3-oxaundecane)[- 11] (2,6)-4-azidoethoxy-s-triazinophane 10b (200 mmol), is dissolved in ethyl acetate and treated with 0.1 N HCl for 5–12 hours, adjusted to neutrality and evaporated to dryness under reduced pressure. The resulting deprotected cyclophane like compound 10b is dissolved in ethyl acetate and treated in one portion with an ethyl acetate mixture of 150 mmol each of benzaldehyde ($L_1$), m-tolualdehyde ($L_2$), m-anisaldehyde ($L_3$), and 3-nitrobenzaldehyde ($L_4$) containing 1 to 3% glacial acetic acid. The reaction is allowed to proceed for 5 to 24 hours then treated directly with $NaCNBH_3$ (2–3 equivalents). The reduction reaction is stirred at room temperature for 1 to 10 hours, filtered, adjusted to neutrality and evaporated to dryness under reduced pressure. The residue is partitioned between ethyl acetate and aqueous $NaHCO_3$. The organic layer is separated, dried ($MgSO_4$), filtered, and evaporated to dryness under reduced pressure. The residue may be purified by column chromatography if needed. This procedure provides the cyclophane like compound 13. Treatment of the resulting compounds as per the procedure of Example 60, Step D, described above, will provide a first round library of cyclophane like compounds 14 with position 4 fixed with four separate benzyl moieties and positions 1,2 and 3 combinatorialized with the four benzyl moieties.

EXAMPLES 62–63

Synthesis of second round library (cyclophane like compounds 16 a,b,c,d) from the cyclophane like compound 12 having the 1,3,5-triazine group (R=SC(Ph)$_3$), and four letters (benzaldehyde, Aldrich-B133-4 [L1]; m-tolualdehyde, Aldrich-T3,550-5 [L2]; m-anisaldehyde, Aldrich-12,965-8 [L3]; and 3-nitrobenzaldehyde, Aldrich-N1,084-5 [L4]. Position 4 is assumed to have active letter, L1, determined from screening of round one. Position 3 will be fixed last. (FIG. 3)

EXAMPLE 62

Step A (FIG. 3)

Cyclophane like compound 12 (200 mmol, from first round), in 800 mL of THF, 3.0 mL of $H_2O$ and triphenyl phosphine (232 mmol) is stirred at 50–80° C. for 12–24 hours under an atmosphere of argon. The reaction mixture is evaporated and the residue is dissolved in 0.5 M $NaH_2PO_4$ (800 mL, aq). The mixture is extracted with EtOAc. The aqueous layer is treated with 3 N NaOH until neutral and then extracted with ether. The $NaSO_4$-dried ether layer is filtered and evaporated to provide the amino ethoxy derivative of cyclophane like compound 12. This material is treated with benzyl aldehyde and subsequently reduced, as described in Example 60, Step D to provide the cyclophane like compound 15 (L1=benzyl). The benzyl moiety is assumed to be the active letter at position 4 as found in Round One.

EXAMPLE 63

Step B (FIG. 3)

Cyclophane like compound 15 is deprotected as described in Example 59 and further reacted as described in Example 57, Step A (separation of 13 into four equal parts) to provide cyclophane like compound 16 in four equal parts a, b, c and d. These materials (libraries) are utilized in various screening procedures.

EXAMPLES 64–68

Synthesis of a third round library (cyclophane like compound 21 a,b,c,d) from (7-(N-tritylsulfenyl)-2,7,10-triaza-3-oxaundecane)[11](2,6)-4-azidoethoxy-s-triazinophane 10 (R=t-BOC) and four letters (benzaldehyde, Aldrich-B133-4 [L1]; m-tolualdehyde, Aldrich-T3,550-5 [L2]; m-anisaldehyde, Aldrich-12,965-8 [L3]; and 3-nitrobenzaldehyde, Aldrich-N1,084-5 [L4]. Positions 3 and 4 are assumed to have active letter, L1, benzyl, determined from screening of rounds one and two. Position 1 will be fixed last. (FIG. 4)

EXAMPLE 64

Step A (FIG. 4)

The cyclophane like compound 10c (R=t-BOC, 200 mmol) in $CH_2Cl_2$/pyridine is treated with triphenyl methanesulfenyl chloride (1.1 equivalents) for 12 to 24 hours under an atmosphere of argon. 0.5 M $NaH_2PO_4$ (aq) was added to neutralize the reaction mixture. The aqueous layer is extracted several times with $CH_2Cl_2$. The $Na_2SO_4$-dried $CH_2Cl_2$ layer is evaporated to give an oily residue which can be purified by column chromatography over silica gel using EtOAc/hexane as the eluent. This procedure will provide cyclophane like compound 17.

EXAMPLE 65
Step B (FIG. 4)

Cyclophane like compound 17 is treated as described in Example 57, Step A, Method 1, 2 or 3 to provide cyclophane like compound 18.

EXAMPLE 66
Step C (FIG. 4)

Cyclophane like compound 18 is treated with 50% trifluoroacetic acid in $CH_2Cl_2$ for 5 to 10 hours at room temperature. The solution is neutralized and extracted with $CH_2Cl_2$. The dried organic layer is evaporated to dryness under reduced pressure. The residue is dissolved in $CH_2Cl_2$ and treated as per the procedure of Example 57, Method 1, 2, or 3, with benzyl aldehyde followed by $NaCNBH_3$. This provides the benzyl letter at position 3.

EXAMPLE 67
Step D (FIG. 4)

The cyclophane like compound 19 is treated as described in Example 60, Step D. In this case only the benzyl moiety, which is derived from benzyl aldehyde/$NaCNBH_3$ is placed at position 4. This is the active letter presumed found in the first round library. This procedure provides cyclophane like compound 20.

EXAMPLE 68
Step E (FIG. 4)

The cyclophane like compound 20 is treated with 0.1 N HCl for 5 to 24 hours at room temperature. The solution is neutralized and extracted with ethyl acetate. After drying and evaporating under reduced pressure, the residue is treated as described in Example 57, Method 1, 2 or 3. In this case the benzyl moieties 21 a, b, c, and d which are derived from the appropriate benzyl aldehydes/$NaCNBH_3$, are placed at position 1. These materials (libraries) are utilized in various screening procedures.

EXAMPLES 69–72

Synthesis of fourth round library (polyaza cyclophane 25 a, b, c and d) from (7-(N-tritylsulfenyl)- 2,7,10-triaza-3-oxaundecane)[11](2,6)-4-azidoethoxy-s- triazinophane 10b (R=t-BOC) and four letters (benzaldehyde, Aldrich-B133-4 [L1]; m-tolualdehyde, Aldrich-T3,550-5 [L2]; m-anisaldehyde, Aldrich-12,965-8 [L3]; and 3-nitrobenzaldehyde, Aldrich-N1,084-5 [L4]. Positions 1, 3, and 4 are assumed to have active letter, L1, benzyl, determined from screening of rounds one, two and three. Position 2 will be fixed last. (FIG. 5)

Figure 5:
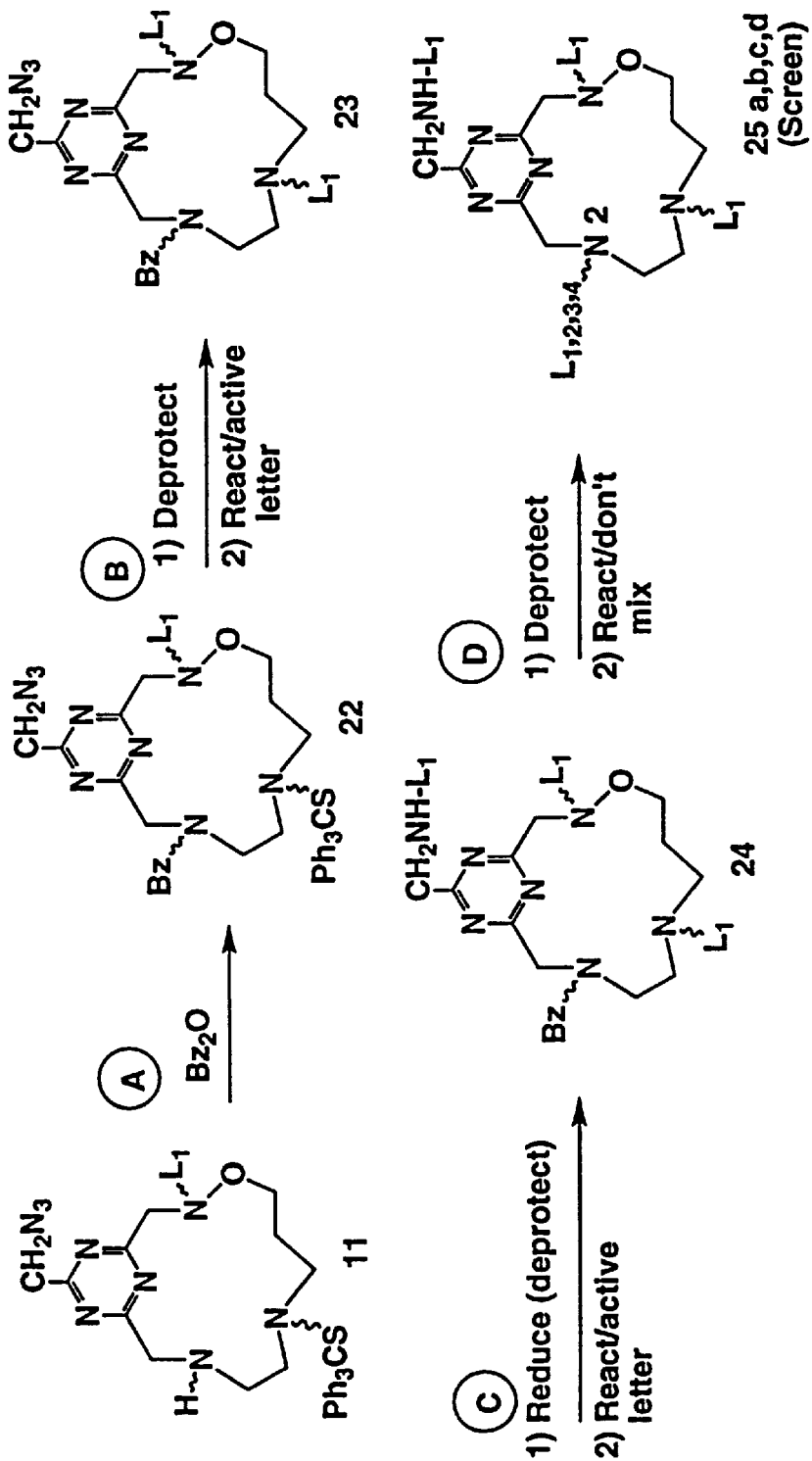
FIG. 5 shows processes for a fourth round of synthesis for preparing libraries of compounds according to the invention.

EXAMPLE 69
Step A (FIG. 5)

The cyclophane like compound 11 a, b, c, or d, saved from Example 57, dependent on which particular letter had the best activity, is benzoylated with benzoic anhydride to provide cyclophane like compound 22.

EXAMPLE 70
Step B (FIG. 5)

Cyclophane like compound 22 is treated as described in Example 59. In this case only the benzyl moiety, which is presumed to be the active letter form Second Round screening, is placed in position 3. This provides the cyclophane like compound 23 with positions 1 and 3 fixed with benzyl moieties.

EXAMPLE 71
Step C (FIG. 5)

The cyclophane like compound 23 is treated as described in Example 60. In this case only the benzyl moiety, which is presumed to be the active letter from the First Round screening, is placed in position 4. This provides the cyclophane like compound 24 with positions 1, 3 and 4 fixed with benzyl moieties.

EXAMPLE 72
Step D (FIG. 5)

The cyclophane like compound 24 is deprotected with NaOMe in methanol. After neutralization, the solution is evaporated to dryness and the residue treated as described in Example 57, Method 1 to provide the cyclophane like compounds 25 a, b, c and d. These materials (libraries) are utilized in various screening procedures.

EXAMPLE 73

Synthesis of libraries from cyclophanes and aldehydes using various selected aldehydes Using the procedure of Examples 57–72, libraries are prepared from nitrogenous macrocycles that are derivatized with one, two, three, four or more of the following aldehydes available from Aldrich Chemical Company, Inc., Milwaukee, Wis. The Aldrich catalog number is given in the left hand column and the compound name is given in the right hand column: Aromatic aldehydes

| | |
|---|---|
| 10793-5 | Phenylacetaldehyde |
| D20425 | Diphenylacetaldehyde |
| 24582-8 | Hydrocinnamaldehyde |
| 24136-9 | Phenylpropionaldehyde |
| 28902-7 | (+/-)-3-Phenylbutyraldehyde |
| 28899-3 | Alpha-amylcinnamaldehyde |
| 16116-0 | Alpha-bromocinnamaldehyde |
| 26813-5 | 4-Stilbenecarboxaldehyde |
| B133-4 | Benzaldehyde |
| 11755-2 | o-Tolualdehyde |
| 25069-4 | Alpha.alpha.alpha-trifluoro-o-tolualdehyde |
| F480-7 | 2-Fluorobenzaldehyde |
| 12497-4 | 2-Chlorobenzaldehyde |
| B5700-1 | 2-Bromobenzaldehyde |
| 10962-2 | o-Anisaldehyde |
| 15372-9 | 2-Ethoxybenzaldehyde |
| N1080-2 | 2-Nitrobenzaldehyde |
| T3550-5 | m-Tolualdehyde |
| 19687-8 | Alpha.alpha.alpha-trifluoro-m-tolualdehyde |
| F500-5 | 3-Fluorobenzaldehyde |
| C2340-3 | 3-Chlorobenzaldehyde |
| B5720-6 | 3-Chlorobenzaldehyde |
| 12965-8 | m-Anisaldehyde |
| 34648-9 | 3-(Trifluoromethoxy)-benzaldehyde |
| 34199-1 | 3-(1,1,2,2-Tetrafluoroethoxy)-benzaldehyde |
| H1980-8 | 3-Hydroxybenzaldehyde |
| N1084-5 | 3-Nitrobenzaldehyde |
| 11528-2 | Isophthaldehyde |
| T3560-2 | p-Tolualdehyde |
| 23363-3 | 4-Ethylbenzaldehyde |
| 13517-8 | 4-Isopropylbenzaldehyde |
| 22494-4 | Alpha.alpha.alpha-trifluoro-p-tolualdehyde |
| 12837-6 | 4-Fluorobenzaldehyde |
| 11221-6 | 4-Chlorobenzaldehyde |
| B5740-0 | 4-Bromobenzaldehyde |
| A8810-7 | p-Anisaldehyde |
| 17360-6 | 4-Ethoxybenzaldehyde |
| 33363-8 | 4-Propoxybenzaldehyde |
| 23808-2 | 4-Butoxybenzaldehyde |

-continued

| | |
|---|---|
| 37060-6 | 4-(Trifluoromethoxy)-benzaldehyde |
| 27486-0 | Terephthaldehyde mono-(diethyl acetal) |
| 14408-8 | 4-Hydroxybenzaldehyde |
| 22277-1 | 4-(Methylthio)benzaldehyde |
| 10976-2 | 4-(Dimethylamino)benzaldehyde |
| D8625-6 | 4-(Dimethylamino)benzaldehyde |
| 33851-6 | 4-(Dibutylamino)benzaldehyde |
| 29355-5 | 4-(3-Dimethylaminopropoxy)benzaldehyde |
| 13017-6 | 4-Nitrobenzaldehyde |
| T220-7 | Terephthaldicarboxaldehyde |
| 34252-1 | 3-Fluoro-2-methylbenzaldehyde |
| 34649-7 | 2-Fluoro-3-(trifluoromethyl)-benzaldehyde |
| 26514-4 | 2,3-Difluorobenzaldehyde |
| 26515-2 | 2,6-Difluorobenzaldehyde |
| 14124-0 | 2-Chloro-6-fluorobenzaldehyde |
| D5650-0 | 2,6-Dichlorobenzaldehyde |
| 25483-5 | 2,3-Dichlorobenzaldehyde |
| D13020-6 | 2,3-Dimethoxybenzaldehyde |
| 29250-8 | 2,6-Dimethoxybenzaldehyde |
| 31980-5 | 3-Fluorosalicylaldehyde |
| 12080-4 | o-Vanillin |
| 18983-9 | 2,3-Dihydroxybenzaldehyde |
| 10604-6 | 2-Chloro-6-nitrobenzaldehyde |
| 16382-1 | 3-methoxy-2-nitrobenzaldehyde |
| 11750-1 | 2,6-Dinitrobenzaldehyde |
| 15104-1 | 2,4-Dimethylbenzaldehyde |
| 15106-8 | 2,5-Dimethylbenzaldehyde |
| 37682-5 | 2-Chloro-5-(trifluoromethyl)benzaldehyde |
| 26516-0 | 3,4-Difluorobenzaldehyde |
| 26517-9 | 2,4-Difluorobenzaldehyde |
| 26518-7 | 2,5-Difluorobenzaldehyde |
| 30600-2 | 3-Chloro-4-fluorobenzaldehyde |
| 34807-4 | 2-Chloro-4-fluorobenzaldehyde |
| 33954-7 | 3-Bromo-3-fluorobenzaldehyde |
| D5660-8 | 3,4-Dichlorobenzaldehyde |
| 14675-7 | 2,4-Dichlorobenzaldehyde |
| 15212-9 | 3-Methyl-p-anisaldehyde |
| 15558-6 | 3-Fluoro-p-anisaldehyde |
| 15429-6 | 5-Bromo-o-anisaldehyde |
| D13040-0 | 2,4-Dimethoxybenzaldehyde |
| D13060-5 | 2,5-Dimethoxybenzaldehyde |
| 14375-8 | 3,4-Dimethoxybenzaldehyde |
| 25275-1 | 3-Ethoxy-4-methoxybenzaldehyde |
| P4910-4 | Piperonal |
| 26459-8 | 1,4-Benzodioxan-6-carboxaldehyde |
| 31691-1 | 4-Hydroxy-3-methylbenzaldehyde |
| 34606-3 | 2-Chloro-4-hydroxybenzaldehyde |
| 25975-4 | 5-Chlorosalicylaldehyde |
| 13728-6 | 5-Bromosalicylaldehyde |
| 14686-2 | 2-Hydroxy-5-methoxybenzaldehyde |
| 16069-5 | 2-Hydroxy-4-methoxybenzaldehyde |
| 14368-5 | 3-Hydroxy-4-methoxybenzaldehyde |
| V110-4 | Vanillin |
| 12809-0 | 3-Ethoxy-4-hydroxybenzaldehyde |
| 34215-7 | 5-(Trifluoromethoxy)salicylaldehyde |
| D10840-5 | 3,4-Dihydroxybenzaldehyde |
| D10820-1 | 2,5-Dihydroxybenzaldehyde |
| 16863-7 | 2,4-Dihydroxybenzaldehyde |
| 22568-1 | 4-(Diethylamino)salicylaldehyde |
| C5880-0 | 5-Chloro-2-nitrobenzaldehyde |
| 13903-3 | 2-Chloro-5-nitrobenzaldehyde |
| C5870-3 | 4-Chloro-3-nitrobenzaldehyde |
| 14432-0 | 4-Hydroxy-3-nitrobenzaldehyde |
| 15616-7 | 3-Hydroxy-4-nitrobenzaldehyde |
| 27535-2 | 2-Hydroxy-5-nitrobenzaldehyde |
| H4810-7 | 5-Hydroxy-2-nitrobenzaldehyde |
| D19360-7 | 2,4-Nitrobenzaldehyde |
| 29013-0 | 3,5-Bis(trifluoromethyl)benzaldehyde |
| 29017-3 | 3,5-Difluorobenzaldehyde |
| 13940-8 | 3,5-Dichlorobenzaldehyde |
| 36811-3 | 3,5-Dihydroxybenzaldehyde |
| 12269-2 | 3,5-Dimethoxybenzaldehyde |
| 36810-5 | 3,5-Dibenzyloxybenzaldehyde |
| M680-8 | Mesitaldehyde |
| 29233-4 | 2,3,5-Trichlorobenzaldehyde |
| 13061-3 | 5-Bromoveratraldehyde |
| 13871-1 | 2,4,6-Trimethoxybenzaldehyde |
| T6840-3 | 3,4,5-Trimethoxybenzaldehyde |
| 14039-2 | 3,5-Dimethyl-4-hydroxybenzaldehyde |

-continued

| | |
|---|---|
| 35768-5 | 2,6-Dimethyl-4-hydroxybenzaldehyde |
| 14040-6 | 3,5-Di-tert-butyl-4-hydroxybenzaldehyde hemihydrate |
| 26181-5 | 3,5-Dichlorosalicylaldehyde |
| 12213-0 | 3,5-Dibromosalicylaldehyde |
| 28344-4 | 3,5-Diiodosalicylaldehyde |
| 13060-5 | 5-Bromovanillin |
| 12948-8 | 5-Iodovanillin |
| 13879-7 | 4,6-Dimethoxysalicylaldehyde |
| 25871-7 | 5-Nitrovanillin |
| S760-2 | 3,5-Dinitrosalicylaldehyde |
| 25959-4 | 2,5-Dimethyl-p-anisaldehyde |
| T6540-4 | 5-Bromo-2,4-dimethoxybenzaldehyde |
| N2800-0 | 4-Nitrovanillin |
| 27680-4 | 3,5-Dinitrosalicylaldehyde |
| 15205-6 | 2,5-Dimethyl-p-anisaldehyde |
| 29251-6 | 5-Bromo-2,4-dimethoxybenzaldehyde |
| 15557-8 | 6-Bromoveratraldehyde |
| 13215-2 | 2,4,5-Trimethoxybenzaldehyde |
| 27960-9 | 6-Nitroveratraldehyde |
| 13765-0 | 6-Nitropiperonal |
| 27679-0 | 2,5-Dichloroterephthaldehyde |
| 33066-3 | 2,3,4-Trifluorobenzaldehyde |
| 29231-1 | 2,3,6-Trichlorobenzaldehyde |
| 15201-3 | 2,3-Dimethyl-p-anisaldehyde |
| 29627-9 | 2,4-Dimethoxy-3-methylbenzaldehyde |
| 15209-9 | 2,3,4-Trimethoxybenzaldehyde |
| 26084-3 | 2,3,4-Trihydroxybenzaldehyde |
| 32893-6 | Tetrafluorobenzaldehyde |
| 10374-8 | Pentafluorobenzaldehyde |
| B3468-0 | 4-Biphenylcarboxaldehyde |
| 19175-2 | 3-Phenoxybenzaldehyde |
| B2700-5 | 3-Benzloxybenzaldehyde |
| 19540-5 | 3-(4-Methylphenoxy)benzaldehyde |
| 19592-8 | 3-(4-tert-Butylphenoxy)benzaldehyde |
| 19539-1 | 3-[3-(Trifluoromethyl)phenoxy]benzaldehyde |
| 19530-8 | 3-(4-Chlorophenoxy)benzaldehyde |
| 19590-1 | 3-(3,4-Dichlorophenoxy)benzaldehyde |
| 19774-2 | 3-(3,5-Dichlorophenoxy)benzaldehyde |
| 19589-8 | 3-(4-Methoxyphonoxy)benzaldehyde |
| 21126-5 | 4-Phenoxybenzaldehyde |
| 12371-4 | 4-Benzyloxybenzaldehyde |
| 16361-9 | 4-Benzyloxy-3-methoxybenzaldehyde |
| 16395-3 | 3-Benzyloxy-4-methoxybenzaldehyde |
| 34603-9 | 3-Methoxy-4-(4-nitrobenzyloxy)benzaldehyde |
| D3600-3 | 3,4-Dibenzyloxybenzaldehyde |
| N10-9 | 1-Naphthaldehyde |
| N20-6 | 2-Naphthaldehyde |
| 15134-3 | 2-Methoxy-1-naphthaldehyde |
| 10324-1 | 4-Methoxy-1-naphthaldehyde |
| H4535-3 | 2-Hydroxy-1-naphthaldehyde |
| 27208-6 | 4-Dimethylamino-1-naphthaldehyde |
| 38201-9 | 2,3-Naphthalendicarboxaldehyde |
| 15014-2 | 2-Fluorenecarboxaldehyde |
| 27868-8 | 9-Anthraldehyde |
| M2965-7 | 10-Methylanthracene-9-carboxaldehyde |
| 15211-0 | 10-Chloro-9-anthraldehyde |
| P1160-3 | Phenanthrene-9-carboxaldehyde |
| 14403-7 | 1-Pyrenecarboxaldehyde |

Aliphatic aldehydes

| | |
|---|---|
| 25254-9 | Fromaldehylde |
| 11007-8 | Acetaldehyde |
| P5145-1 | Propionaldehyde |
| 24078-8 | Isobutyraldehyde |
| T7150-1 | Trimethylacetaldehyde |
| B10328-4 | Butyraldehyde |
| M3347-6 | 2-Methylbutyraldehyde |
| 11009-4 | 2-Ethylbutyraldehyde |
| 14645-5 | Isovaleraldehyde |
| 35990-4 | 3,3-Dimethylbutyraldehyde |
| 11013-2 | Valeraldehyde |
| 25856-3 | 2-Methylvaleraldehyde |
| D19050-0 | 2,4-Dimethylvaleraldehyde |

-continued

| | |
|---|---|
| 11560-6 | Hexanal |
| E2910-9 | 2-Ethylhexanal |
| 30355-0 | 3,5,5-Trimethylhexanal |
| H212-0 | Heptaldehyde |
| 0560-8 | Octyl aldehyde |
| N3080-3 | Nonyl aldehyde |
| 12577-6 | Decyl aldehyde |
| U220-2 | Undecylic aldehyde |
| M8675-8 | 2-Methylundecanal |
| D22200-3 | Dodecyl aldehyde |
| 26923-9 | Tridecanal |
| T1000-6 | Tetradecy aldehyde |
| 11022-1 | Acrolein |
| 13303-5 | Methacrolein |
| 25614-5 | 2-Ethylacrolein |
| 25613-7 | 2-Butylacrolein |
| 13298-5 | Crotonaldehyde |
| 19261-9 | trans-2-Methyl-2-butenal |
| 29468-3 | 2-Ethyl-trans-2-butenal |
| 30407-7 | 3-Methyl-2-butenal |
| 26925-5 | trans-2-pentenal |
| 29466-7 | 2-Methyl-2-pentenal |
| 29097-1 | 2,2-Dimethyl-4-pentenal |
| 13265-9 | trans-2-Hexenal |
| 25176-3 | trans-2-Heptenal |
| 30796-3 | 2,6-Dimethyl-5-heptenal |
| 26995-6 | trans-2-Octenal |
| 34364-1 | (R)-(+)-Citronellal |
| 37375-3 | (S)-(−)-Citronellal |
| 25565-3 | trans-2-Nonenal |
| 37562-4 | cis-4-Decenal |
| 36733-8 | trans-4-Decenal |
| 13227-6 | Undecylenic aldehyde |
| 24911-4 | dis-9-hexadecenal |
| 27221-3 | Cyclopropanecarboxaldehyde |
| 10846-4 | Cyclohexanecarboxaldehyde |
| 10933-9 | Cyclooctanecarboxaldehyde |
| 30441-7 | 3-Cyclohexylpropionaldehyde |
| T1220-3 | Tetrahydrobenzaldehyde |
| 21829-4 | (S)-(−)-Perillaldehyde |
| 26467-9 | 2,6,6-Trimethyl-1-cyclohexene-1-acetaldehyde |
| 10937-1 | 5-Norbornen-2-carboxaldehyde |
| 21824-3 | (1R)-(−)-Myrtenal |
| 37531-4 | Glyoxal-1,1-dimethyl acetal |
| 21877-4 | 7-Methoxy-3,7-dimethyloctanal |
| 23254-8 | 3-Ethoxymethacrolein |
| 27525-5 | 2,5-Dimethoxy-3-tetrahydrofurancarboxaldehyde |
| 26918-2 | 2,2-Dimethyl-3-hydroxypropionaldehyde |
| G480-2 | DL-Glyceraldehyde |
| G478-0 | D-Glyceraldehyde |
| 21665-8 | L-Glyceraldehyde |
| 34140-1 | 3-(Methylthio)propionaldehyde |
| 30583-9 | 3-(Dimethylamino)acrolein |
| 36549-9 | 3-(Dimethylamino)-2-methyl-2-propenal |
| 17733-4 | Pyrubic aldehyde |
| 27706-1 | (S)-(−)-2-(Methoxymethyl)-1-pyrrolidinecarboxaldehyde |
| 29211-7 | 2-Methoxy-1-pyrrolidinecarboxaldehyde |
| 29210-9 | 2-Methoxy-1-piperidinecarboxaldehyde |

EXAMPLE 74

Synthesis of libraries from cyclophanes and aryl bromide using as the illustrative letters, benzyl bromide Aldrich-B133-4 [L1]; 3-methylbenzyl bromide, Aldrich-T3,550-5 (L2); 3-methoxybenzyl bromide, Aldrich-12,965-8 [L3]; and 3-nitrobenzyl bromides, Aldrich-N1,08 4-5 [L4]. Preparation of library subsets using benzyl halides in place of benzyl aldehydes.

Library subsets 14 a–d, 16 a–d, 21 a–d, and 25 a–d are prepared by utilizing benzyl halides [benzyl bromide (L1), 3-methylbenzyl bromide (L2), 3-methoxybenzyl bromide (L3), and 3-nitro-benzyl bromide (L4)] corresponding to benzyl aldehydes employed in the above described synthesis and deconvolution. In this example, direct alkylation provides the combinatorialized positions directly (reduction procedures are not used).

Combinatorialization is effected as previously described with the exception that alkylation reactions with aryl bromides are used in place of the described Schiff's base reductive alkylations. Alkylation procedures provide libraries comparable to libraries synthesized by reductive alkylations. Benzyl halides are readily available from various commercial chemical suppliers.

EXAMPLE 75

Synthesis of libraries from cyclophanes and halides using various selected halides Using the procedure of Example 74, libraries are prepared from nitrogenous macrocycles that are derivatized with one, two, three, four or more of the following halides available from Aldrich Chemical Company, Inc., Milwaukee, Wis. The Aldrich catalog number is given in the right hand column and the compound name is given in the left hand column:

| | |
|---|---|
| 13925-4 | Alpha,2,4-trichlorotoluene |
| 19349-6 | 2-Iodobenzyl chloride |
| 25917-9 | Alpha-3,4-trichlorotoluene |
| 10733-6 | 2-Nitrobenzyl chloride |
| 10030-7 | Alpha-bromo-2,6-dichlorotoluene |
| T5630-8 | Alpha-2,6-trichlorotoluene |
| 14011-2 | 4-Nitrobenzyl chloride |
| 19164-7 | 3,5-Dinitrobenzyl chloride |
| 13672-7 | 3-Chlorobenzyl bromide |
| 19166-7 | 3-Nitrobenzyl chloride |
| 30726-2 | 2,4-Dinitrobenzyl chloride |
| 25225-5 | 2-Chlorobenzyl bromide |
| C5490-2 | 2-Chloromethyl-4-nitrophenol |
| 42369-6 | 3,5-Dinitrobenzyl chloride |
| F760-1 | 2-Fluorobenzyl chloride |
| 11196-1 | 4-Chlorobenzyl chloride |
| 21811-1 | 2-Chloro-6-fluorobenzyl chloride |
| F780-6 | 3-Fluorobenzyl chloride |
| 11522-3 | 3-Chlorobenzyl chloride |
| 19625-8 | 4-Chloro-2-nitrobenzyl chloride |
| F800-4 | 4-Fluorobenzyl chloride |
| 11588-6 | 3-Chlorobenzyl chloride |
| 27250-7 | 2-Chloro-2',4'-difluoroacetophenone |
| 19425-5 | 2-Chlorobenzyl chloride |
| 24118-0 | 2-Chlorobenzyl chloride |
| 15907-7 | Alpha-4-dichloroanisole |
| 13359-0 | Benzyl chloride |
| S62774-7 | 2-(Chloromethyl)benzonitrile |
| S77343-3 | N-(2-Chloroethylidene)-2,4-dinitroaniline |
| 16770-3 | Alpha'-chloro-alpha,alpha,alpha-trifluoro-m-xylene |
| 25070-8 | Alpha'-chloro-alpha,alpha,alpha-trifluoro-o-xylene |
| 36581-5 | Alpha'-chloro-alpha,alpha,alpha-trifluoro-p-xylene |
| 19875-7 | 4-Bromophenyl 2-chloroethyl ether |
| 30511-1 | 2-Chlorophenyl 2-bromoethyl ether |
| S67805-8 | 2-(2-Bromoethoxy)-5-chloro-1-nitrobenzene |
| S60515-8 | 2-Bromoethyl-4-chlorophenyl ether |
| S45235-1 | 1-(2-Chloroethyl)-4-fluorobenzene |
| 19177-9 | 5-Methyl-2-nitrobenzyl chloride |
| 19232-5 | 5-Methyl-3-nitrobenzyl chloride |
| 19536-7 | 2-Methyl-3-nitrobenzyl chloride |
| C7330-3 | Alpha-chloro-o-xylene |
| S43061-7 | Beta-chlorophenetole |
| S92214-5 | 3-Methyl-4-nitrobenzyl chloride |
| C7335-4 | Alpha-chloro-m-xylene |
| C7340-0 | Alpha-chloro-p-xylene |
| 20938-4 | 3-Methoxybenzyl chloride |
| 41760-2 | 2-Chloroethylphenyl sulfide |
| 27024-5 | 4-Methoxybenzyl chloride |
| 26340-0 | 3,5-Bis(trifluoromethyl)benzyl chloride |
| S61404-1 | 2-Chloroethyl-4-chlorophenyl sulfide |
| C4040-5 | (2-chloroethyl)benzene |

-continued

| | |
|---|---|
| S44579-7 | 4'-Bromo-3-chloropropiophenone |
| S65169-9 | 2-Chloroethyl-4-nitrobenzoate |
| 13515-1 | 3-Chloro-4'-fluoropropiophenone |
| 33561-4 | 3-Chloropropiophenone |
| S88196-1 | Benzyl-2-chloroacetate |
| S83340-1 | 3-Chloropropyl-2,4-dichlorophenyl ether |
| S53571-0 | 3-Chloropropyl-4-fluorophenyl ether |
| 12640-3 | 2,5-Dimethylbenzyl chloride |
| C6810-5 | 1-Chloro-3-phenylpropane |
| S80872-5 | 2,5-Dimethoxybenzyl chloride |
| D15060-6 | 3,4-Dimethylbenzyl chloride |
| S56939-9 | 3-Chloropropyl-4-nitrophenyl ether |
| S79921-1 | 3-Chloropropyl-phenyl sulfide |
| S79298-5 | 3-Chloropropyl-phenyl ether |
| S83280-4 | 2-Chloroethyl-p-tolyl sulfide |
| S63793-9 | 4-Chlorobenzyl-2-chloroethyl sulfide |
| 33026-4 | 3,5-Dimethoxybenzyl chloride |
| S37787-2 | N-(2-Chloroethyl)benzylalanine HCl |
| 36344-8 | 4-Chlorobutyrophinone |
| S55923-7 | 7-Chloro-p-cymene |
| S66335-2 | 2,4,5-Trimethylbenzyl chloride |
| S56937-2 | 1-(2-(2-Chloroethoxy)-ethoxy)-4-nitrobenzene |
| P1530-7 | 4-Phenoxybutyl chloride |
| S40755-0 | 4,6-Bis(chloromethyl)-m-xylene |
| 13698-0 | Alpha-2-chloroisodurene |
| 24650-6 | 1-Chloro-2-methyl-2-phenylpropane |
| S34433-8 | 4-Chloro-4'-methylbutyrophenone |
| S95372-5 | 4-Bromophenyl-3-chloro-2,2-dimethylpropionate |
| 39086-0 | 4-Chlorobutylbenzoate |
| S79927-0 | 3-Chloro-1-methylpropylphenyl sulfide |
| S34430-3 | 4-Chloro-4'-methoxybutyrophenone |
| S79928-9 | 3-Chloropropyl-m-toluyl sulfide |
| S42717-9 | N-(2-Chloroethyl)-N-methylbenzylamine hydrochloride |
| S52026-8 | 4-tert-Butyl-1-chloromethyl-2-nitrobenzene |
| D6560-7 | 2,4-Bis(chloromethyl)-1,3,5-trimethylbenzene |
| 19153-1 | 4-(tert-Butyl)benzyl chloride |
| S62686-4 | 2,3,5,6-Tetramethylbenzyl chloride |
| S87624-0 | (+)-1-Chloro-3-methyl-2-phenylbutane |
| S35320-5 | 4-(2-Methylphenoxy)butyl chloride |
| S37684-1 | N-(2-chloroethyl)-N-ethylbenzylamine HCl |
| S36329-4 | 3-Methoxy-3-(4-tolyl)-propyl chloride |
| S42735-7 | N-(3-Chloropropyl)-N-methylbenzylamine HCl |
| S34414-1 | 4-Chloro-3',4'-dimethylbutyrophenone |
| S36370-7 | 4-(3-Methylphenoxy)butyl chloride |
| S66008-6 | N-(2-Chloroethyl)-N-ethyl-m-toluidine |
| S34420-6 | 4-Chloro-4'-ethylbutyrophenone |
| S36371-5 | 4-(4-methylphenoxy)butyl chloride |
| S34409-5 | 4-Chloro-2',4'-dimethoxybutyrophenone |
| S79934-3 | 5-Chloropentylphenyl sulfide |
| S52555-3 | 5-Chloro-2-(o-tolyl)-valeronitrile |
| S52133-7 | Alpha-chloro-4-(tert-pentyl)-toluene |
| S87628-3 | (+)-1-Chloro-3,3-dimethyl-2-phenylbutane |
| S35168-7 | 3-Isopropoxy-3-phenylpropyl chloride |
| 10086-2 | 3,6-Bis(chloromethyl)durene |
| S37754-6 | 1-Chloro-3-mesityloxy-2-propanol |
| S66289-5 | Alpha,alpha-3-dichlorohexamethylbenzene |
| S86989-9 | 1,2-Bis(chloromethyl)-3,4,5,6-tetramethylbenzene |
| S86009-3 | 1,4-Bis(chloromethyl)-2,5-diethoxybenzene |
| S52500-6 | 2-Chloromethyl-4-nitrophenylheptyl ether |
| S54873-1 | 2-(2-Chloroethyl)-2-phenylpentanenitrile |
| S36287-5 | 3-Isopropoxy-3-(p-toluyl)propyl chloride |
| B9140-4 | 4'-tert-Butyl-4-chlorobutyrophenone |
| C8,121-7 | cinnamyl bromide |
| 18,706-2 | 3-bromobenzylbromide |
| 15,791-0 | methyl bromoacetate |
| 24,248-9 | bromoacetonitrile |
| 30,127-2 | bromoacetamide |
| 36,242-5 | 2-chloro-N-methoxy-N-methylacetamide |
| 17568 | 3-bromomethylbenzonitrile (Fluka) |

EXAMPLE 76

Synthesis of libraries from cyclophanes and aryl acid halides using as the illustrative letters, benzoyl chloride Aldrich-[L1]; 3-methylbenzoyl chloride Aldrich-T3,550-5 [L2]; 3-methoxybenzoyl chloride, Aldrich-12,965-8 [L3]; and 3-nitrobenzoyl chloride Aldrich-N1,084-5 [L4].

Preparation of library subsets 14 a–d, 16 a–d, 21 a–d, and 25 a–d using benzoic acids and benzoic acid derivatives is effected in place of benzyl aldehydes or benzyl halides described above.

Library subsets 14 a–d, 16 a–d, 21 a–d, and 25 a–d are prepared by utilizing benzoic acid halide moieties to acylate the primary amine and secondary and primary oxyamines followed by reduction of the resultant amide bond to afford a benzyl moiety combinatorialized at each selected site in the polyamine/oxyamine. Benzoic acid chloride (L1), 3-methyl-benzoic chloride (L2), 3-methoxybenzoic chloride (L3), and 3-nitro-benzoic chloride (L4)] corresponding to benzyl bromides and benzaldehydes employed in the initial synthesis are employed in this approach.

Combinatorialization is continued as described above except acylation reactions with benzoic acid chlorides are used in place of Schiff's base reductive alkylations. Acylation procedures provide libraries comparable to libraries synthesized by reductive alkylation or direct alkylation. Benzoic acid halides are readily available from various commercial chemical suppliers.

EXAMPLE 77

Synthesis of libraries from cyclophanes and aryl acid halides using various selected acid halides Using the procedure of Example 76, libraries are prepared from nitrogenous macrocycles that are derivatized with one, two, three, four or more of the following acid halides available from Aldrich Chemical Company, Inc., Milwaukee, Wis. The Aldrich catalog number is given in the left hand column and the compound name is given in the right hand column:

| | |
|---|---|
| 10663-1 | p-Toluoyl chloride |
| 30253-8 | 3-Cyanobenzoyl chloride |
| 13096-6 | (+/−)-2-Cloro-2-phenylacetyl chloride |
| 26366-4 | 3-(Chloromethyl)benzoyl chloride |
| 27078-4 | 4-(Chloromethyl)benzoyl chloride |
| 24947-5 | 4-(Trifluoromethyl)benzoyl chloride |
| 19394-1 | 4-Chlorophenoxyacetyl chloride |
| 24948-3 | 2-(Trifluoromethyl)benzoyl chloride |
| 19394-1 | 4-Chlorophenoxyacetyl chloride |
| 24948-3 | 2-(Trifluoromethyl)benzoyl chloride |
| 10663-1 | p-Toluoyl chloride |
| 25027-9 | 3-(Trifluoromethyl)benzoyl chloride |
| S67828-7 | 2-(2,4,5-Trichlorophenoxy)acetyl chloride |
| 12201-7 | o-Toluoyl chloride |
| 40248-6 | 4-(Trifluoromethoxy)benzoyl chloride |
| 37502-0 | 3-(Dichloromethyl)benzoyl chloride |
| 12225-4 | m-Toluoyl chloride |
| 12482-6 | 4-Cyanobenzoyl chloride |
| P1675-3 | Phenylacetyl chloride |
| S88415-4 | 2-(Phenylthio)propionyl chloride |
| 15802-3 | Phenoxyacetyl chloride |
| 36475-4 | trans-4-Nitrocinnamoyl chloride |
| 28882-9 | 4-Ethoxybenzoyl chloride |
| 23024-3 | m-Anisoyl chloride |
| S67595-4 | 2,3-Dibromo-3-phenylpropionyl chloride |
| 30101-9 | Benzyloxyacetyl chloride |
| 25470-3 | o-Anisoyl chloride |
| C8110-1 | Cinnamoyl chloride |
| 31693-8 | 3-Methoxyphenylacetyl chloride |
| A8847-6 | p-Anisoyl chloride |
| 16519-0 | Acetylsalicyloyl chloride |
| 36569-6 | 4-Methoxyphenylacetyl chloride |
| 24944-0 | Hydrocinnamoyl chloride |
| 26528-4 | 3,5-Bis(trifluoromethyl)benzoyl chloride |
| 28350-94 | Ethylbenzoyl chloride |

-continued

| | |
|---|---|
| S40503-5 | 2-Phenoxypropionyl chloride |
| 33304-2 | 2,5-Bis(trifluoromethyl)benzoyl chloride |
| S62043-2 | p-Tolylacetyl chloride |
| 16171-3 | 3,5-Dimethoxybenzoyl chloride |
| 42339-4 | (R)-(-)-A-Methoxy-A-(trifluoromethyl)-phenylacetyl chloride |
| 26480-6 | 2,5-Dimethoxyphenylacetyl chloride |
| 25804-0 | 3,4-Dimethoxybenzoyl chloride |
| T6980-9 | 3,4,5-Trimethoxybenzoyl chloride |
| 26242-0 | 2,6-Dimethoxybenzoyl chloride |
| 13430-9 | trans-2-Phenyl-1-cyclopropanecarbonyl chloride |
| S62264-8 | 5-(Dimethylsulfamoyl)-2-methoxybenzoyl chloride |
| 37383-4 | 2,4-Dimethoxybenzoyl chloride |
| A1740-4 | o-Acetylmandelic chloride |
| 24945-9 | 4-Phenyl-1,2,3,4-tetrachloro-1,3-butadiene-1-carbonyl cloride |
| 36848-2 | trans-3-(trifluoromethyl)cinnamoyl chloride |
| 15712-0 | 4-tert-butylbenzoyl chloride |
| S42860-4 | 2-Phenylbutyryl chloride |
| 22203-8 | 4-Butylbenzoyl chloride |
| 23747-7 | 3,4-Dimethoxyphenylacetyl chloride |
| 22204-6 | 4-Butoxybenzoyl chloride |
| S65659-3 | 2-(4-Chlorobenzoyl)benzoyl chloride |
| 22214-3 | 4-Pentylbenzoyl chloride |
| C3928-8 | 2-Chloro-2,2-diphenylacetyl chloride |
| S43639-9 | 4(4-Nitrophenylazo)benzoyl chloride |
| 33158-9 | Diphenylacetyl chloride |
| S80926-8 | 4-(Phenylazo)benzoyl chloride |
| S61661-3 | 2-Diphenylacetyl chloride |
| 16114-4 | 4-Biphenylcarbonyl chloride |
| 22209-7 | 4-Hexylbenzoyl chloride |
| 22205-4 | 4-Heptyloxybenzoyl chloride |
| 22211-9 | 4-Hexyloxybenzoyl chloride |
| 22206-2 | 4-Heptyloxybenzoyl chloride |

EXAMPLE 78

Preparation of 1,2,5,8-tetraaza-9-oxa-1-methyl-5-(tosyl)undecano-[2,4]-6-azidoethoxy-s-triazinophane
(Step 1)
1,3,5-triazine-2-azidoethoxy-4-aminooxy-6-(1-methylhydrazine)

A cold solution of cyanuric chloride in acetonitrile is treated sequentially in the following order with the following solutions: one equivalent of azidoethanol one equivalent of sodium hydride in acetonitrile; one equivalent of N-hydroxyphthalimide/one equivalent of sodium hydride; and 3.5 equivalents of methylhydrazine. The sequential reactions are each cooled prior to addition of the reactants and then allowed to warm to room temperature and stirred at ambient temperature for 5–24 hours before adding the next reactant. The reaction with methyl hydrazine is refluxed for 3–24 hours to obtain final chlorine displacement and removal of the phthaloyl protecting group. The reaction mixture is cooled, filtered and taken to dryness by evaporation under reduced pressure. Purification by silica gel flash column chromatography will provide the title compound.
Step 2
Disuccinimidyl N-(t-boc)iminodiacetate Prepared according to a synthesis described by T. J. McMurry, et al., *Bioconjugate Chem.*, 1992, 3, 108–117. Disuccinimidyl derivatives of imino-di-acids can be prepared as described by this general procedure.
Step 3
1,2,5,8-tetraaza-9-oxa-1-methyl-5-(p-methylsulfonyl)undecano-[2,4]-6-azidoethoxy-s-triazinophane A solution of 1,3,5-triazine-2-azidoethoxy-4-aminooxy-6-(1-methylhydrazine) (one equivalent) in DMF is reacted with a solution of disuccinimidyl N-(t-boc)iminodiacetate (one equivalent) in DMF and triethylamine (two equivalents) under high dilution conditions at 20–100° C. for over 5 to 24 hours. The solution is evaporated to dryness under reduced pressure. The residue is dissolved in HCl/MeOH and kept at ambient temperature for 5 to 24 hours before evaporating to dryness. The residue is treated with pyridine/p-toluene sulfonyl chloride. After heating at ambient temperature to 80° C. for 5 to 24 hours the solution is evaporated to dryness. The residue is dissolved in dry THF and treated with $BH_3$.THF at 0° C. for one hour and then at 45° C. to ambient temperature for 24 to 48 hours. The solution is treated with MeOH and then evaporated to dryness. This process is repeated. The final residue is dissolved in EtOH and the solution is saturated with gaseous HCl at 0° C. This solution is refluxed for 5 to 24 hours and evaporated to dryness. The residue is triturated with ether and then dissolved in $H_2O$ and treated with saturated $NaHCO_3$. The mixture is extracted with ethyl acetate several times. The ethyl acetate solution is treated with HCl/MeOH and evaporated to dryness to provide the title compound as its hydrochloride salts.

EXAMPLE 79

Figure 6:
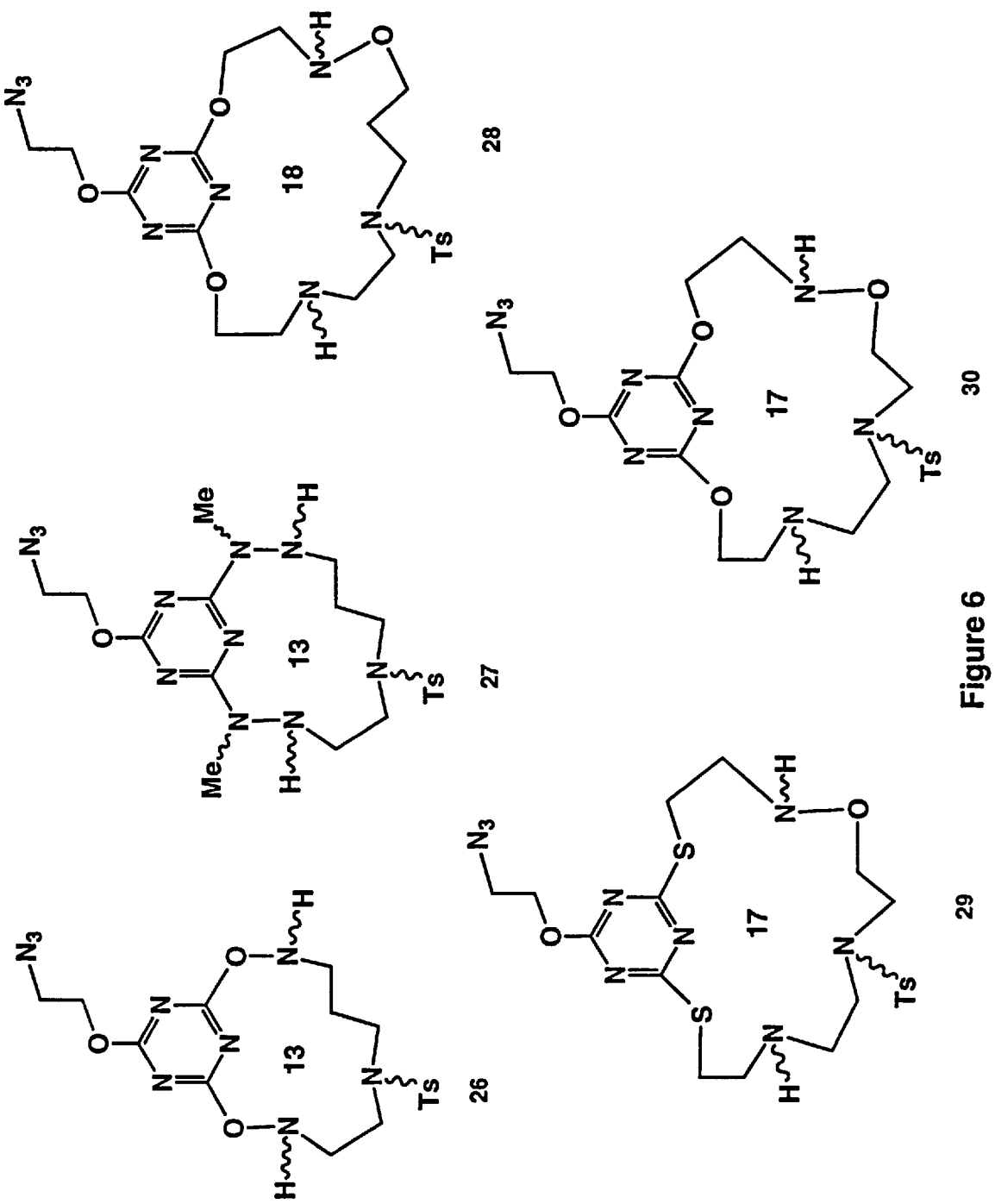
FIG. 6 depicts certain embodiments in accordance with the invention.

Preparation of 2,5,9-triaza-1,10-dioxa-5-(tosyl)-decano-[2,6]-4-azidoethoxy-1,3,5-triazinophane 26 (FIG. 6)

The title compound is prepared as per the general procedure of Example 78. The heterocycle used is 2-azidoethoxy-4,6-di-(O-phthalimido)-s-triazine. It is reacted with succinimidyl-N-tosyl-(N-hydroxysuccinimidylacetate)-β-alanine to give the title compound. The intermediate diamide compound can be used if it is desired to include amide type nitrogenous moieties in the bridge. Alternately, it can be reduced as per Example 78 to a bridge that includes two hydroxyamine moieties.

EXAMPLE 80

Preparation of 1,2,5,9,10-penta-aza-1,10-dimethyl-5-(tosyl)- decano-[2,6]-4-azidoethoxy-1,3,5-triazinophane 27 (FIG. 6)

The title compound is prepared as per the general procedure of Example 74. The heterocycle used is 2-azidoethoxy-4,6-di-(N-methyl hydrazino)-s-triazine. It is reacted with succinimidyl-N-tosyl-(N-hydroxysuccinimidylacetate)-β-alanine to give the title compound.

The intermediate dihydrazide compound can be used if it is desired to include hydrazide type nitrogenous moieties in the bridge. Alternately, it can be reduce as per Example 74 to a bridge that includes two hydrazine moieties.

EXAMPLE 81

Preparation of 4,9,12-triaza-1,5,15-trioxa-9-(tosyl)-pentadecano-[2,6]-4-azidoethoxy-1,3,5-triazinophane 28 (FIG. 6)

The title compound is prepared as per the general procedure of Example 78. The heterocycle used is 4-aminopropoxy-2-azidoethoxy-6-hydroxylaminoethoxy-s-triazine. It is reacted with succinimidyl-N-tosyl-(N-hydroxysuccinimidylacetate)-β-alanine to give the title compound. The intermediate amide-N-(hyroxyamide) compound can be used if it is desired to include amide and N-hydroxyamide type nitrogenous moieties in the bridge. Alternately, it can be reduced as per Example 78 to a bridge that include an amine and a hydroxyamine moiety.

EXAMPLE 82

Preparation of 4,7,11-triaza-10-oxa-1,14-dithia-7-(tosyl)-tetradecano-[2,6]-4-azidoethoxy-s-triazinophane 29 (FIG. 6)

The title compound is prepared as per the general procedure of Example 78. The heterocycle used is 4-aminopropanthial-2-azidoethoxy-6-hydroxylaminoethanthial-s-triazine. It is reacted with succinimidyl-N-tosyl-(N-hydroxysuccinimidylacetate)-β-alanine to give the title compound. The intermediate amide-N-(hyroxyamide) compound can be used if it is desired to include amide and N-hydroxyamide type nitrogenous moieties in the bridge. Alternately, it can be reduced as per Example 78 to a bridge that includes an amine and a hydroxyamine moiety.

EXAMPLE 83
Preparation of 4,7,11-Triaza-1,10,14-trioxa-7-(tosyl)tetradecano-[2,6]-4-azidoethoxy-1,3,5-triazinophane 30 (FIG. 6)

The title compound is prepared as per the general procedure of Example 78. The heterocycle used is 2-azidoethoxy-4,6-diaminoethoxy-s-triazine. It is reacted with succinimidyl-N-tosyl-(N-hydroxysuccinimidylacetate)-β-alanine to give the title compound. The intermediate diamide compound can be used if it is desired to include amide type nitrogenous moieties in the bridge. Alternately, it can be reduced as per Example 78 to form a bridge that includes amine moieties.

EXAMPLE 84
N1-(t-Boc)-N2-tosyl-diaminoethane

To a solution of N-(t-Boc)-diaminoethane (153 g, 0.95 mol) and triethylamine (202 mL) in $CH_2Cl_2$ (1400 mL) at room temperature, was added p-toluenesulfonyl chloride (190 g, 1.0 mol). The reaction was stirred for 16 hours, partitioned with water and separated. The organic phase was dried (MgSO4), filtered, and concentrated. The resulting residue was triturated with hexane to give 36 g, (84%) of the title compound as a white solid.

$^1$H NMR ($CDCl_3$) δ 1.41 (s, 9H, $(CH_3)_3$); 2.40 (s, 3H, $CH_3$); 3.03 (m, 2H, $CH_2$); 3.21 (m, 2H, $CH_2$); 5.2 (brs, 1H, NH); 7.29 (d, 2H, Ar); 7.34 (d, 2H, Ar).

EXAMPLE 85
N1-(t-Boc)-N2-[(3-chloropropyl)tosyl]diaminoethane

A solution of N1-(t-Boc)-N2-tosyl-diaminoethane (297 g, 0.94 mol), 1-(methanesulfonyl)-3-chloropropanol (188 g, 1.09 mol) and $Cs_2CO_3$ (344 g, 1.06 mol) in acetone(9 L) was heated at reflux for 16 hours. The reaction mixture was concentrated, partitioned between $CH_2Cl_2$ and $H_2O$, separated, dried ($MgSO_4$), filtered and concentrated. Trituration of the resulting white solid with ether:hexane (1/1, v/v), gave 327 g (89%), of the title compound. mp 95–96° C. $^1$H NMR ($CDCl_3$) δ 1.42 (s, 9H, t-Butyl); 2.0 (m, 2H, $CH_2$); 2.41 (s, 3H, $CH_3$), 3.22 (m, 6H, $CH_2$); 3.55 (m, 2H, $CH_2$); 4.91 (bs, 1H, NH); 7.30 (d, 2H, ArH); 7.66 (d, 2H, ArH).

EXAMPLE 86
N1-(t-Boc)-N2-[(3-phthalimidooxypropyl)tosyl]diaminoethane

A suspension of N1-(t-Boc)-N2-[(3-chloropropyl)-tosyl]diaminoethane (27 g, 0.69 mol), sodium iodide (13.5 g, 0.09 mol), sodium carbonate (10.8 g, 0.10 mol) and N-hydroxyphthalimide (97%, 16.5 g, 0.1 mol) in DMF (1000 mL) was stirred vigorously at 80° C. for 24 hours. The reaction was concentrated, partitioned between $CH_2Cl_2$ and $H_2O$ and washed thoroughly with $H_2O$ (3×200ml). The organic layer was separated, dried ($MgSO_4$), filtered and concentrated. The resulting solid was recrystallized from methanol to give 20.0 g (56%) of the title compound as solid.

mp 111–112° C. $^1$H NMR ($CDCl_3$) δ 1.41 (s, 9h, t-butyl); 2.0 (m, 2H, $CH_2$); 2.41 (s, 3H, Ar—$CH_3$); 3.20 (m, 6H, $CH_2$); 4.25 (t, 2H, $CH_2$); 5.07 (bs, 1H, NH); 7.29 (d, 2h, ArH); 7.67 (m, 6H, ArH).

EXAMPLE 87
N1-(t-Boc)-N2-[(3-O-aminopropanol-1-yl)tosyl]diaminoethane

A solution of N1-(t-Boc)-N2-[(3-phthalimidooxypropyl)-tosyl]diaminoethane (49 g, 95 mmol) and hydrazine (30 mL, 0.94 mol) in methanol (1500 mL) was stirred at 35° C. for 3 hours. The solid was then filtered off, toluene was added to the mother liquor, and the mother liquor was concentrated. The resultant oil was chromatographed on silica gel (EtOAC) to afford 27 g. (73%) of the title compound.

$^1$H NMR ($CDCl_3$) δ 1.39 (s, 9H, $(CH_3)_3$); 1.78 (m, 2H, $CH_2$); 2.32 (s, 3H, $CH_3$); 3.06–3.23 (m, 6H, $CH_2$); 3.59 (m, 2H, $CH_2$); 5.21 (bs, 1H, NH); 5.34 (s, 2H, $NH_2$); 7.20 (d, 2H, Ar); 7.66 (d, 2H, Ar).

EXAMPLE 88
N2-[(3-O-aminopropanol-1-yl)tosyl]diaminoethane.HCL

A solution of N1-(t-Boc)-N2-[(3-O-aminopropanol-1-yl)tosyl]diaminoethane (11.5 g, 30 mmol) in ethyl acetate (50 mL) was added to a solution of HCl (gas) (88 g) dissolved in ethyl acetate (1000 mL). After 1 hour the product was filtered off and washed with ether. After drying 9.8 g (92%) of the title compound was isolated.

$^1$H NMR (DMSO) δ 1.84 (m, 2H, $CH_2$); 2.42 (s, 3H, $CH_3$); 2.95 (m, 2H, $CH_2$); 3.17 (m, 2H, $CH_2$), 3.29 (m, 2H, $CH_2$); 4.07 (m, 2H, $CH_2$); 7.47 (d, 2H, Ar); 7.73 (d, 2H, Ar); 8.24 (bs, 2H, $NH_2$); 11.1 (bs, 2H, $ONH_2$)

Figure 7:
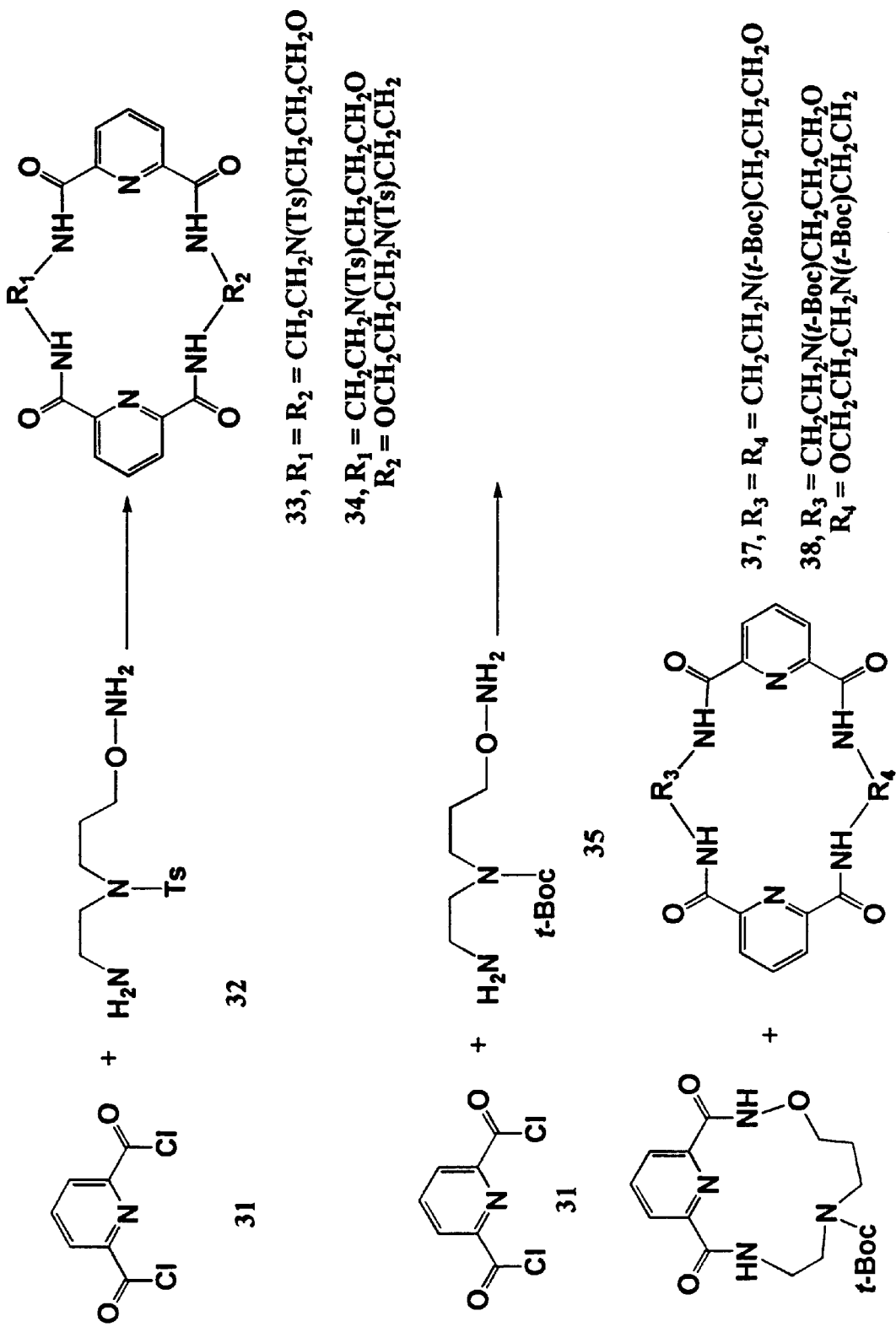
FIG. 7 is a synthetic scheme for the synthesis of macrocyclic compounds according to the invention.

EXAMPLE 89
Preparation of N1-[(tosyl)-O-aminopropanol-3-yl]diaminoethane 32 (FIG. 7)

The hydrochloride salt of N1-[(tosyl)-O-aminopropanol-3-yl]diaminoethane.2HCl (9.0 g, 22.7 mmol) was treated with a solution of sodium hydroxide (5 g, 0.125 mol) in water (150 mL) for 1 hour. The solution was diluted with brine (100 mL) and then extracted with ethyl acetate. The combined organic extract was dried ($Na_2SO_4$) and filtered. The solvent was evaporated under reduced pressure and the residue was dried under high vacuum. The title compound 6.5 g (99%) was obtained as a colorless oil.

$^1$H NMR ($CDCl_3$) δ 1.75–1.92 (m, 2H), 2.41 (s, 3H), 2.85 (t, 2H, J=6.2 Hz),3.09–3.24 (m, 4H), 3.65 (t, 2H, J=6.0 Hz), 7.29 (d, 2H, J=8.4 Hz), 7.68 (d, 2H, J=9.0 Hz).

EXAMPLE 90
Preparation of 1,11,18,28-tetracarboxy-2,10,19,27-tetraaza-7,22-bis-(tosyl)aza-3,26-dioxa-[11.11]pyridinophane 33, and 1,11,18,28-tetracarboxy-2,10,19,27-tetraaza-7,24-bis-(tosyl)aza-3,20-dioxa-[11.11]pyridinophane 34 (FIG. 7)

A solution of N1-[(tosyl)-O-aminopropanol-3-yl]diaminoethane 32 (1.44 g, 5.0 mmol) and proton sponge (3.5 g, 16.0 mmol) in benzene (125 mL), and a solution of 2,6-pyridinedicarbonyl dichloride (Aldrich) (1.02 g, 5.0 mmol) in acetonitrile (20 mL) and benzene (105 mL) were simultaneously added at room temperature to a flask containing benzene (350 mL) with stirring for 5 hours. The resulting reaction mixture was stirred at room temperature for 40 hours. The solvent was evaporated and the residue was purified by flash chromatography on a silica gel column (15 cm×5 cm). Elution with hexanes:ethyl acetate (1:2, v/v), ethyl acetate and then ethyl acetate:methanol (2:1, v/v), afforded 1.0 g (48%) of an isomeric mixture of the title compounds as a white foam.

TLC: Rf 0.26; ethyl acetate:methanol; 4:1, v/v; silica gel.
$^1$H NMR ($CDCl_3$) δ 1.90–2.10 (m, 4 H), 2.37 (s, 6 H), 3.36

(t, 4 H, J=6.8 Hz), 3.42–3.55 (m, 4 H), 3.57–3.70 (m, 4 H), 3.95–4.12 (m, 4 H), 7.22 (d, 4 H, J=8.2 Hz), 7.71 (d, 4 H, J=8.2 Hz), 7.95–8.10 (m, 2 H), 8.24–8.48 (m, 4 H), 8.68 (bs, 2H, disappeared in $D_2O$), 10.96 (s, 2H, disappeared in $D_2O$). $^{13}C$ NMR ($CDCl_3$) δ 21.32, 27.20, 38.95, 45.68, 45.88, 47.43, 72.98, 124.64, 125.26, 127.25, 130.01, 135.32, 139.11, 144.15, 147.88, 148.39, 160.95, 164.05. Mass spectrum (FAB), m/z 837 $(M+1)^+$. Mass spectrum (HRFAB), m/z 969.164 $(M+Cs)^+$ ($C_{38}H_{44}N_8S_2O_{10}Cs$ requires 969.167).

EXAMPLE 91

N-Benzyl-3-amino-1-propanol

To a solution of benzaldehyde (10 g, 94.23 mmol) and trimethylorthoformate (15.5 mL, 141 mmol) in MeOH (300 mL) was added dropwise 3-amino-1-propanol (7.21 ml, 94.23 mmol) at room temperature. The reaction was allowed to stir at room temperature for 5 hours followed by cooling to 0° C. in an ice bath. Sodium borohydride (3.56 g, 94.23 mmol) was added in two portions and when the bubbling stopped the solvent was evaporated. The resulting residue was partitioned between ethyl acetate (75 mL) and water (75 ml). The aqueous layer was extracted twice with ethyl acetate (75 mL). The ethyl acetate extracts were collected and washed twice with Brine (50 mL), dried over $MgSO_4$, filtered, and concentrated. Drying afforded 14.42 g (93%) of the compound which was used in the next step of synthesis without further purification.

EXAMPLE 92

N-Phthalimidoethyl(benzyl)-3-amino-1-propanol

N-Benzyl-3-amino-1-propanol (6 g, 36.76 mmol) was dissolved in DMF (300 mL). To this solution was added $K_2CO_3$ (1.52 g, 11.03 mmol) and KI (0.915 mg, 0.551 mmol) and the reaction mixture was heated to 65° C. for 10 hours. The reaction had gone to completion as indicated by TLC using ethyl acetate:dichloromethane (2:3, v/v). The solvent volume was reduced by evaporation under vacuo and the resulting residue was partitioned between ethyl acetate (100 mL) and water (100 mL). The water layer was extracted 3x with 50 mL of ethyl acetate. The ethyl acetate layers were combined and washed twice with brine (50 mL), dried over $MgSO_4$, filtered and concentrated. The title compound was purified by silica gel flash column chromatography using ethyl acetate:Hexanes (2:5, v/v) as the eluent. The appropriate fractions were collected and concentrated to afford 7.0 g (56%) of the title compound.

EXAMPLE 93

N-Phthalimidoethyl-3-amino-1-propanol

N-Phthalimidoethyl(benzyl)-3-amino-1-propanol (4.62 g, 11.95 mmol), Pd/C 10% (1 g) and MeOH:acetic acid (95:5, v/v) (100 mL) was transferred to a 250 mL par hydrogenation flask. The flask was purged and filled with $H_2$ three times and then left under $H_2$ at 55 psi with shaking. The mixture absorbed 20 psi of $H_2$ in 30 minutes. The shaking was stopped and the pressure was raised to 55 psi again. After 3 hrs the pressure was 45 psi so the pressure was increased to 55 psi once more. The reaction was complete as indicated by TLC dichloromethane:MeOH (9:1, v/v) in 4 hours. The reaction mixture was filtered though a bed of celite and the solvent evaporated under vacuo to leave a yellowish oil. The oil was purified by silica gel flash column chromatography using dichloromethane:MeOH (9:1, v/v) as the eluent. The appropriate fractions were combined and concentrated under vacuo to afford 2.51 g (68%) of the title compound.

EXAMPLE 94

N-[Phthalimidoethyl-(t-Boc)]-3-amino-1-propanol

N-Phthalimidoethyl-3-amino-1-propanol (2.51 g, 8.14 mmol) and triethylamine were added to dichloromethane (40 mL). Di-tert-butyl-dicarbonate (3.55 g, 16.28 mmol) was added in one portion. The reaction went to completion in 4 hours as indicated by TLC using ethyl acetate:hexanes (1:1, v/v). The reaction mixture was washed 3x with water and once with brine, dried over $MgSO_4$, filtered, and concentrated. The residue was purified by silica gel flash column chromatography using hexanes:ethyl acetate (8:2 to 1:1, v/v). The appropriate fractions were combined and evaporated to afford 2.31 g (81%) of the title compound.

EXAMPLE 95

N-[Phthalimidoethyl(t-Boc)]-3-amino-1-(O-phthalimido)-propanol

N-[Phthalimidoethyl(t-Boc)]-3-amino-1-propanol (1.16 g, 3.33 mmol), triphenylphosphine (959 mg, 3.66 mmol) and N-hydroxyphthalimide (597 mg, 3.66 mmol) were dissolved in distilled THF (30 mL). The solution was cooled to 0° C. in an ice bath and diethylazodicarboxylate (DEAD, 0.629 mL, 4.00 mmol) was added dropwise. Five drops of DEAD were added and the next five were added after the orange color had dissipated, this procedure was repeated until all the DEAD was added over a period of about 2 hours. The reaction mixture was allowed to warm up to room temperature overnight. The end point of the reaction was detected by TLC using ethyl acetate: hexanes (1:1, v/v). The solvent was removed under vacuo and dry diethyl ether (100 mL) was added. The title compound precipitated out of the solution to afford 1.23 g (75%) after drying.

EXAMPLE 96

N1[(t-Boc)-1-(O-amino)propanol-3-yl]diaminoethane 35 (FIG. 7)

N-[Phthalimidoethyl(t-Boc)]-3-amino-1-(O-phthalimido)-propanol (10.35 g, 20.97 mmol) was suspended in Ethanol (absolute, 300 mL). To this solution was added hydrazine (5 eq. 105 mmol, 3.3 mL) in one portion. The reaction mixture was stirred for 6 hours at which time the resulting white precipitate was filtered off. The filtrate was concentrated under vacuo to a white solid with a yellowish green oil. To the residue was added ethyl ether (150 ml), the white solid was filtered, and the filtrate was concentrated to a white solid with a yellowish green oil. The target compound was purified from this mixture by silica gel flash column chromatography using dichloromethane:MeOH (9:1, v/v) followed by dichloromethane:$NH_4OH$:MeOH (85:10:5, v/v) as the eluents. The desired fractions were combined, concentrated, and dried to afford 3.1 g (63%) of the title compound.

EXAMPLE 97

Preparation of 1,11-dicarboxy-2,10-diaza-7-(t-Boc)aza-3-oxa[2.6]pyridinophane 36; 1,11,18,28-tetracarboxy-2,10,19,27- tetraaza-7,22-bis-(t-Boc)aza-3,26-dioxa-[11.11]pyridinophane 37; and 1,11,18,28-tetracarboxy-2,10,19,27-tetraaza-7,24-bis- (t-Boc)aza-3,20-dioxa-[11.11]pyridinophane 38 (FIG. 7)

The cyclization of N1-[(t-Boc)-O-amino-3-propanol-1-yl]diaminoethane 35 (0.70 g, 3.0 mmol) with 2,6-pyridinedicarbonyl dichloride (Aldrich) (0.61 g, 3.0 mmol) was carried out following the procedure of Example 90. After work-up the residue was purified by flash chromatography on a silica gel column (15 cm×2 cm). Elution with ethyl acetate, and then ethyl acetate:methanol (50:1 and 20:1, v/v) afforded 0.37 g (34 %) of the [1+1] cyclized product 36, and 0.18 g (16%) of an isomeric mixture of [2+2] cyclized products 37 and 38 as white foams.

Product 36: TLC: Rf 0.52; ethyl acetate:methanol; 10:1, v/v; silica gel. $^1$H NMR (CDCl$_3$) δ 1.48 (s, 9H), 1.55–1.75 (m, 2H), 3.24–3.42 (m, 4H), 3.75–3.90 (m, 2H), 4.28–4.41 (m, 2H), 7.95–8.08 (m, 2H), 8.24 (bs, 1H), 8.34 (dd, 1 H, J=1.9, 7.0 Hz), 8.62 (bs, 1 H). Mass spectrum (electron impact), m/z 364 (M)$^+$. Mass spectrum (CI), m/z 365 (M+1)$^+$. Mass spectrum (HRFAB); m/z 364.175 (M)$^+$ (C$_{17}$H$_{24}$N$_4$O$_5$ requires 364.174).

Products 37 and 38: $^1$H NMR (CDCl$_3$) δ 1.31 (s, 18 H), 1.75–2.02 (m, 4 H), 3.30–3.80 (m,12 H), 3.95–4.20 (m, 4H), 8.00 (t, 2 H, J=8.2 Hz), 8.15–8.38 (m, 4 H); mass spectrum (FAB), m/z 729 (M+1)$^+$.

EXAMPLE 98

Figure 8:
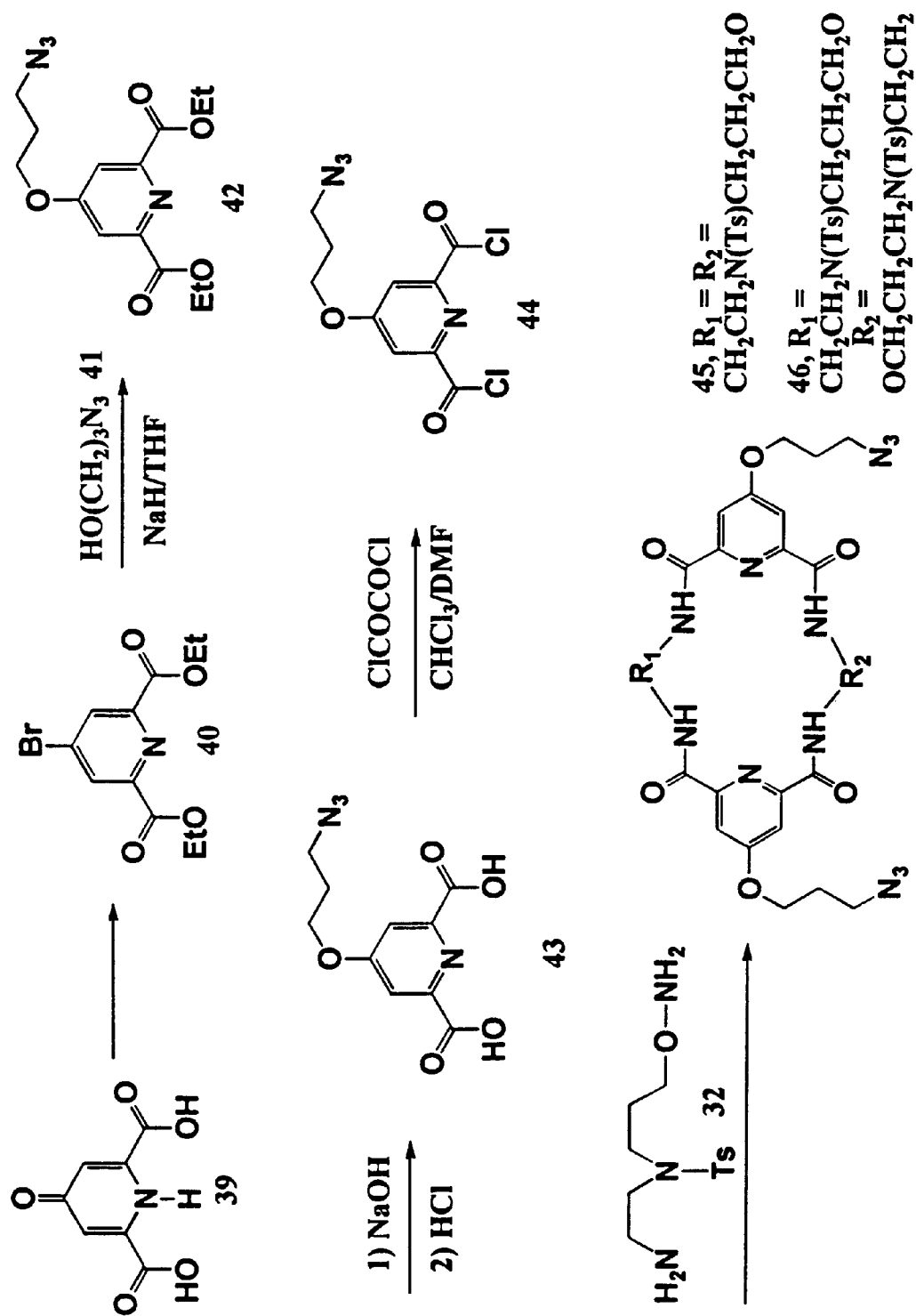
FIG. 8 is a synthetic scheme for the synthesis of macrocyclic compounds according to the invention.

4-(3-azidopropoxy)-pyridine-2,6-dicarboxylic acid 43 (FIG. 8)

Diethyl-4-(3-azidopropoxy)-2,6-pyridinedicarboxylate, prepared above, (11.0 g, 34 mmol) was treated with a solution of sodium hydroxide (4.0 g, 0.10 mol) in water (120 mL) at 90–100° C. for 40 min. The reaction mixture was cooled to 10° C. and acidified to pH 1–2 with concentrated hydrochloric acid. The mixture was heated to dissolve the resulting white precipitate. Upon cooling 6.8 g (75 %) of the title compound was obtained as white crystals.

$^1$H NMR (CDCl$_3$) δ 1.97–2.15(m, 2 H), 3.54 (t, 2 H, J=6.0 Hz), 4.30 (t, 2 H, J=6.0 Hz), 7.73 (s, 2 H).

EXAMPLE 99

Preparation of 16,33-(bis)azidopropoxy-1,11,18,28-tetracarboxy-2,10,19,27-tetraaza-7,22-bis-(tosyl)aza-3,26-dioxa-[11.11](2,6)pyridinophane 45, and 16,33- (bis) azidopropoxy-1,11,18,28-tetracarboxy-2,10,19,27-tetraaza-7,24-bis-(tosyl)aza-3,20-dioxa-[11.11](2,6)pyridinophane 46 (FIG. 8)

4-(3-azidopropoxy)-pyridine-2,6-dicarboxylic acid 43 (1.33 g, 5.0 mmol) was suspended in chloroform (80 mL) and DMF (0.4 mL). Oxalyl chloride (2.7 mL, 3.9 g, 30.7 mmol) was added dropwise to the above stirred suspension. The resulting reaction mixture was stirred at room temperature for 2 days. The solvent was evaporated and the residue was dried under high vacuum for 24 hours. The 4-(3-azidopropoxy)-pyridine-2,6-dicarbonyldichloride obtained was used for the next coupling reaction directly without further purification.

A solution of N1-[(tosyl)-O-aminopropanol-3-yl] diaminoethane (1.43 g, 5.0 mmol) proton sponge (1.1 g, 5.1 mmol) and triethylamine (0.5 mL) in benzene (125 mL), and a solution of 4-(3-azidopropoxy)-pyridine-2,6-dicarbonyldichloride (5.0 mmol) in acetonitrile (50 mL) and benzene (75 mL) were added simultaneously at room temperature to a flask containing benzene (350 mL) with stirring for 5 hours. The stirring was continued for 2 days. The resulting precipitate was filtered off and the filtrate was concentrated under reduced pressure. The residue was purified by flash chromatography on a silica gel column (15 cm×5 cm). Elution with ethyl acetate, ethyl acetate:methanol (20:1 and 10:1, v/v) afforded 0.90 g (43%) of an isomeric mixture of [2+2] cyclized products 45 and 46 as a white foam.

TLC: Rf 0.49; ethyl acetate:methanol; v/v; silica gel. $^1$H NMR (CDCl$_3$) δ 1.85–2.15 (m, 4H), 2.35 (s, 3 H), 3.20–3.70 (m, 8 H), 3.90–4.08 (m, 2 H), 4.12–4.28 (m, 2 H), 7.21 (d, 2H, J=8.0 Hz), 7.60–6.80 (m, 4 H), 8.63 (bs, 1H), 10.87 (s, 1H). Mass spectrum (FAB), m/z 1035 (M+1)$^+$. Mass spectrum (HRFAB), m/z 1167.259 (M+Cs)$^+$ (C$_{44}$H$_{54}$N$_{14}$S$_2$O$_{12}$Cs requires 1167.254).

EXAMPLE 100

N1-[(3-trifloroacetamido)propan-1-yl]-N2-trifloroacetyl-1,4- diaminobutane(trifloroacetyl salt, N1) 50; N1-[(3-trifloro- acetamido)propan-1-yl]-N1-t-Boc-N2-trifloroacetyl-1,4-diamino- butane 52; and N1-[t-Boc(3-aminopropyl)]-1,4-diaminobutane 54 (FIG. 9)

The title compounds were prepared according to the reported procedures of M. C. O'Sullivan, D. M. Dalrymple, Tet. Lett. 1995, 36, 345).

EXAMPLE 101

Figure 9:
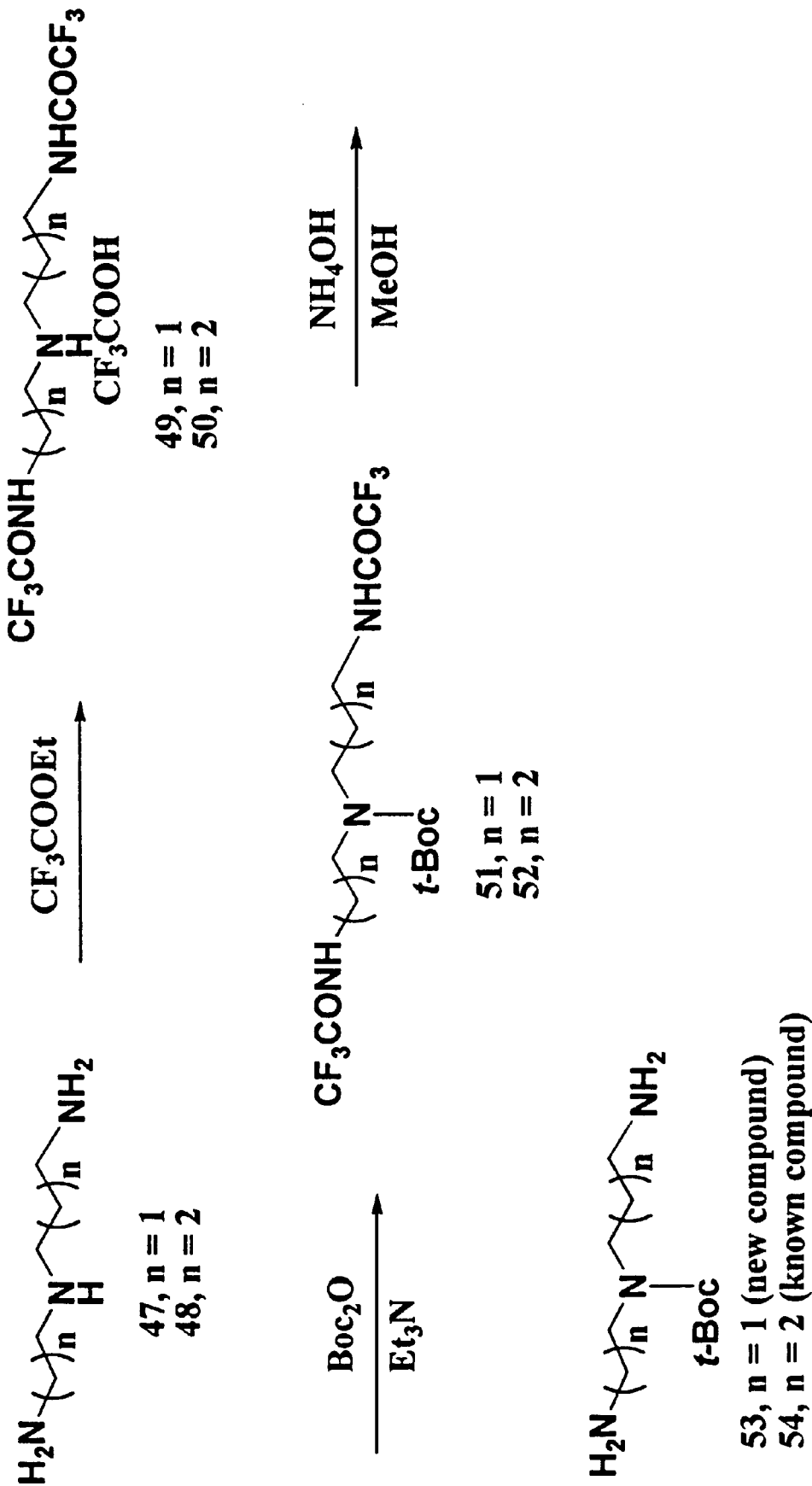
FIG. 9 is a synthetic scheme for the synthesis of certain bridges according to the invention.

N1-[(2-trifloroacetamido)ethan-1-yl]-N2-(trifluoroacetyl)-1,3- diaminopropane(trifloroacetyl salt, N1) 49 (FIG. 9)

Ethyl trifluoroacetate (16.7 mL, 19.89 g, 0.14 mol, 3.5 eq) was added to a solution of N-(2-aminoethyl)-1,3-propanediamine (Aldrich) (4.7 g, 40 mmol) in acetonitrile (25 mL) followed by water (0.72 g, 40 mmol, 1 eq). The resulting reaction mixture was refluxed overnight and the solvent was evaporated under reduced pressure. The residue was dried under high vacuum to give 16.8 g (99.4%) of the title compound as a white solid.

$^1$H NMR (CD$_3$OD+D$_2$O ) δ 1.88–2.05 (m, 2H), 3.08 (t, 2H, J=7.6 Hz), 3.23 (t, 2H, J=6.0 Hz), 3.40 (t, 2H, J=6.8 Hz), 3.63 (t, 2H, J=6.0 Hz).

EXAMPLE 102

N1-[(t-Boc)2-trifloroacetamidoethan-1-yl]-N2-trifloroacetyl- 1,3-diaminopropane 51 (FIG. 9)

Di-t-butyldicarbonate (13.2 g, 60 mmol, 1.5 eq) was added to a cooled solution of N1-[(2-trifloroacetamido) ethan- 1-yl]-N2-(trifloroacetyl)-1,3-diaminopropane (trifloroacetyl salt, N1) 49 (16.8 g, 40 mmol) and triethylamine (10.9 g, 108 mmol, 2.7 eq) in THF (140 mL). The resulting reaction mixture was stirred at room temperature overnight. Saturated ammonium chloride (270 mL) was added and the mixture was extracted with chloroform. The chloroform extract was washed with brine, dried (Na$_2$SO$_4$, and filtered. The solvent was evaporated and the residue was purified by flash chromatography on a silica gel column (17 cm×7 cm). Elution with dichloromethane and dichloromethane:methanol (20:1, v/v) afforded 16.4 g (100%) of the title compound as a white solid.

TLC: Rf 0.37; dichloromethane:methanol; 50:1, v/v; silica gel. $^1$H NMR (CDCl$_3$) δ 1.49 (s, 9 H), 1.65–1.88 (m, 2H), 3.20–3.37 (m, 4 H), 3.40–3.55 (m, 4H), 7.00 (bs, 1H), 8.10 (bs, 1H).

EXAMPLE 103

N1-[(t-Boc)-2-aminoethyl]-1,4-diaminopropane 53 (FIG. 9)

N1-[(t-Boc)2-trifloroacetamidoethan-1-yl]-N2-trifloroacetyl-1,3-diaminopropane 51 (16.4 g, 40 mmol) was treated with a mixture of methanol:30% aqueous ammonium hydroxide (270 mL) (1:2, v/v) and refluxed for 20 hours. The solvent was evaporated under reduced pressure and the residue was purified by flash chromatography on a silica gel column (25 cm×7 cm). Elution with methanol:30% aqueous ammonium hydroxide(50:1, 20:1 and 5:1, v/v) gave 6.0 g (69%) of the title compound as a colorless oil.

TLC: Rf 0.47; methanol:30% aqueous ammonium hydroxide; 10:1, v/v; silica gel. $^1$H NMR (CDCl$_3$) δ 1.45 (s, 9 H), 1.56–1.72 (m, 2H), 1.54 (bs, 4H, disappeared in D$_2$O), 2.68 (t, 2H, J=6.6 Hz), 2.81 (t, 2H, J=6.4 Hz), 3.18–3.35 (m, 4 H). $^{13}$C NMR (CDCl$_3$) δ 28.22, 31.75, 38.96, 40.43, 44.71, 49.81, 79.32, 155.73. Mass spectrum (HRFAB), m/z 218.186 (M+1)$^+$ (C$_{10}$H$_{24}$N$_3$O$_2$ requires 218.187).

Figure 10:
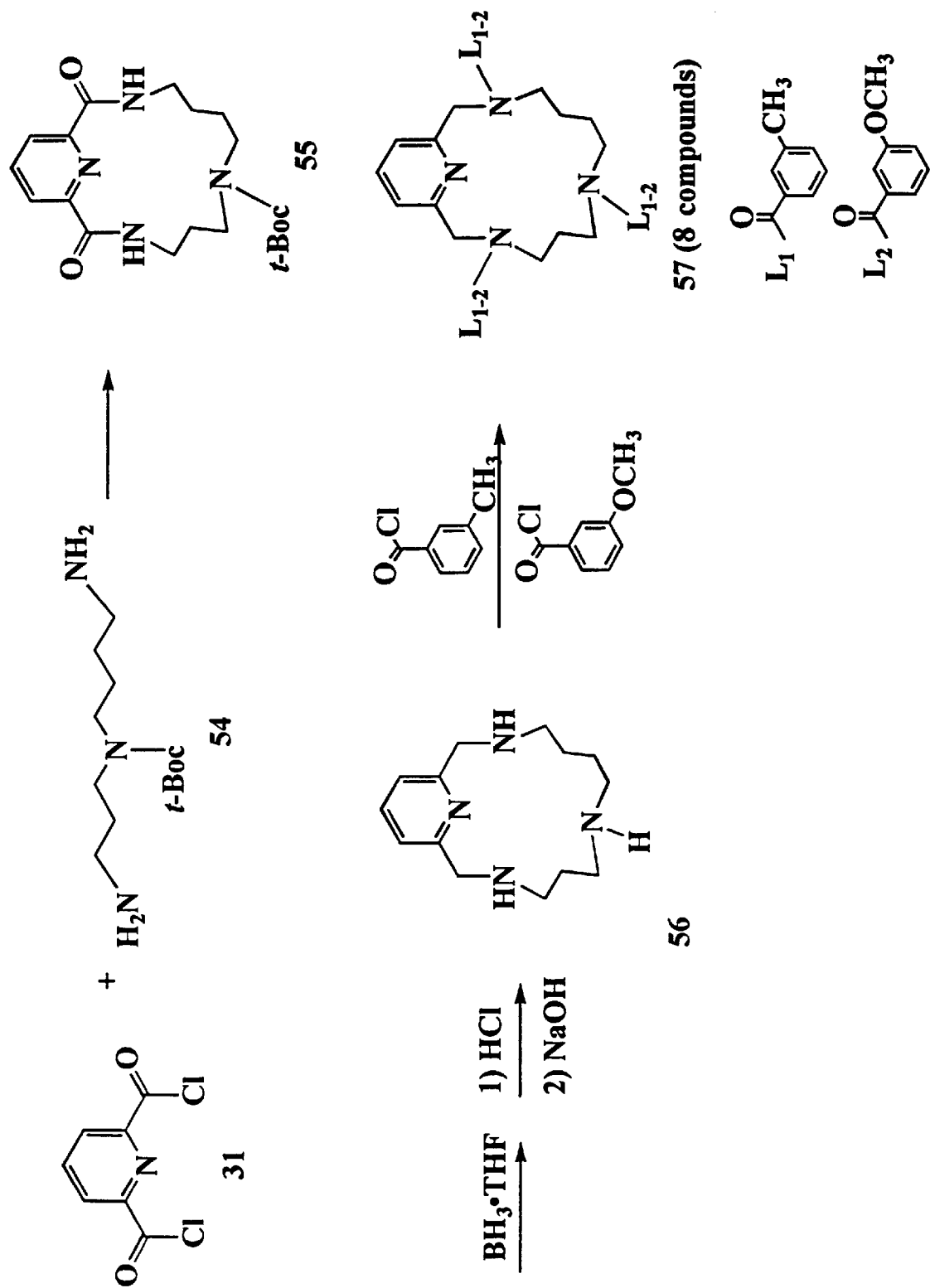
FIG. 10 is a synthetic scheme for the synthesis of a macrocyclic compound according to the invention and the processes for the preparation of libraries utilizing this macrocyclic compound.

EXAMPLE 104
1,12-dicarboxy-2,11-diaza-7-(t-Boc)aza-[2.6]pyridinophane 55 (FIG. 10)

A solution of N1-[(t-Boc)3-aminopropyl]-1,4-diaminobutane 54 (3.58 g, 14.6 mmol), proton sponge (3.0 g, 14 mmol) and Hunig's base (4.9 mL, 3.62 g, 28 mmol) in benzene (250 mL), and a solution of pyridine-2,6-dicarbonyl dichloride (Aldrich) (2.86 g, 14 mmol) in acetonitrile (100 mL) and benzene (150 mL) were simultaneously added at room temperature to a flask containing benzene (800 mL) with stirring for 7 hours. The stirring was continued for 2 days. The solvent was evaporated and the residue was purified by flash chromatography on a silica gel column (20 cm×5 cm). Elution with ethyl acetate and ethyl acetate-:methanol (20:1, v/v) afforded 1.93 g (37%) of the title compound as a white foam.

TLC: Rf 0.51; ethyl acetate:methanol; 20:1, v/v; silica gel. $^1$H NMR (CDCl$_3$) δ 1.42 (s, 9H), 1.55–1.70 (m, 2H), 1.75–2.05 (m, 4H), 3.30–3.60 (m, 8H), 7.88 (bs, 1H), 8.00 (t, 1H, J=8.0 Hz), 8.13–8.22 (m, 2H), 8.40 (bs, 1H). $^{13}$C NMR (CDCl$_3$) δ 24.91, 25.39, 28.39, 37.00, 38.52, 45.29, 48.02, 80.11, 123.91, 124.31, 139.59, 148.50, 149.43, 156.00, 163.45. Mass spectrum (HRFAB), m/z 509.118 (M+Cs)$^+$ (C$_{19}$H$_{28}$N$_4$O$_4$Cs requires 509.116).

EXAMPLE 105
2,7,11-triazadodecane-[2.6]pyridinophane 56 (FIG. 10)

Method A

Borane-tetrahydrofuran complex (1.0 M, 270 mL) was added to a solution of 1,12-dicarboxy-2,11-diaza-7-(t-Boc)aza- [2.6]pyridinophane 55 (1.51 g, 4.0 mmol) in THF (60 mL). The resulting mixture was heated to reflux under stirring for 24 hours and cooled to 0° C. Water (50 mL) was added dropwise to destroy excess borane. The solvent was evaporated and the residue was dissolved in a mixture of water (150 mL) and concentrated hydrochloric acid (260 mL). The mixture was stirred at room temperature overnight and at 90° C. for 20 min. The mixture was concentrated to a volume of about 200 mL and made basic (e.g. pH 13–14) with aqueous sodium hydroxide and then extracted with chloroform. The chloroform extracts were dried and the solvent was evaporated under reduced pressure. The residue was purified by flash chromatography on a silica gel column (18 cm×3 cm). Elution with methanol:30% aqueous ammonium hydroxide (30:1, 10:1 and 5:1, v/v) gave 0.45 g (46%) of the title compound as a pale yellow oil.

Method B

Trifluoroacetic acid (8.0 mL) was added dropwise to a stirred solution of 2,11-diaza-7-(t-Boc)azadodecane[2.6]-pyridinophane (349 mg, 1.0 mm), compound 64 (FIG. 11), in chloroform (3.0 mL) at 0° C. The resulting reaction mixure stirred at room temperature for 4 hours. The solvent was evaporated and the residue was dissolved in water and made basic (pH 14) by the addition of an aqueous solution of NaOH. The mixture was extracted with chloroform and the extract was washed with brine, dried (Na$_2$SO$_4$) and concentrated. The residue was purified by flash chromatography on a silica gel column (11 cm by 2 cm). Elution with methanol and then methanol:30% ammonium hydroxide, 10:1, v/v, afforded 180 mg (73%) of the title compound as a colorless oil.

TLC: Rf 0.41; methanol:30% aqueous ammonium hydroxide; 5:1, v/v; silica gel. $^1$H NMR (CDCl$_3$) δ 1.24–1.38 (m, 2H), 1.39–1.58 (m, 4H), 2.10 (bs, 3H, disappeared in D$_2$O), 2.30–2.57 (m, 8H), 3.64 (s, 2H), 3.71 (s, 2H), 6.83 (d, 2H, J=7.6 Hz), 7.35 (t, 1H, J=7.6 Hz). $^{13}$C NMR (CDCl$_3$) δ 26.76, 27.21, 29.34, 48.16, 48.23, 48.63, 48.84, 53.99, 55.20, 120.47, 136.32, 159.04, 159.75. Mass spectrum (HRFAB), m/z 249.207 (M+1)$^+$ (C$_{14}$H$_{25}$N$_4$ requires 249.207).

EXAMPLE 106
Preparation of Library 57 (FIG. 10)

A solution of m-toluoyl chloride (0.36 mL, 0.42 g, 2.7 mmol) and m-anisoyl chloride (0.38 mL, 0.46 g, 2.7 mmol) in dichloromethane (20 mL) was added dropwise to a stirred solution of 2,7,11-triaza-[2.6]pyridinophane 56 (0.37 g, 1.49 mmol) and Hunig's base (2 mL, 1.48 g, 11.5 mmol) in dichloromethane (50 mL). The resulting reaction mixture was stirred at room temperature overnight. The dichloromethane solution was washed with water and brine. The dried (Na$_2$SO$_4$) dichloromethane solution was concentrated and the residue was purified by flash chromatography on a silica gel column (12 cm×3 cm). Elution with ethyl acetate and then ethyl acetate:methanol (20:1, v/v) afforded 0.89 g (95%) of the library 57 as a white foam.

TLC: Rf 0.50; ethyl acetate:methanol; 20:1, v/v; silica gel. $^1$H NMR (CDCl$_3$) δ 1.15–1.90 (m, 6H), 1.28–1.62 (m, 4.5H), 2.95–3.60 (m, 8H), 3.78 (s, 4.5H), 4.48–4.70 (m, 2H), 4.80–5.05 (m, 2H), 6.78–7.80 (m, 15H). Mass spectrum (electrospray), m/z 603, 619, 635, 651 (M+1)$^+$; 625, 641, 657, 673 (M+Na)$^+$.

Figure 11:
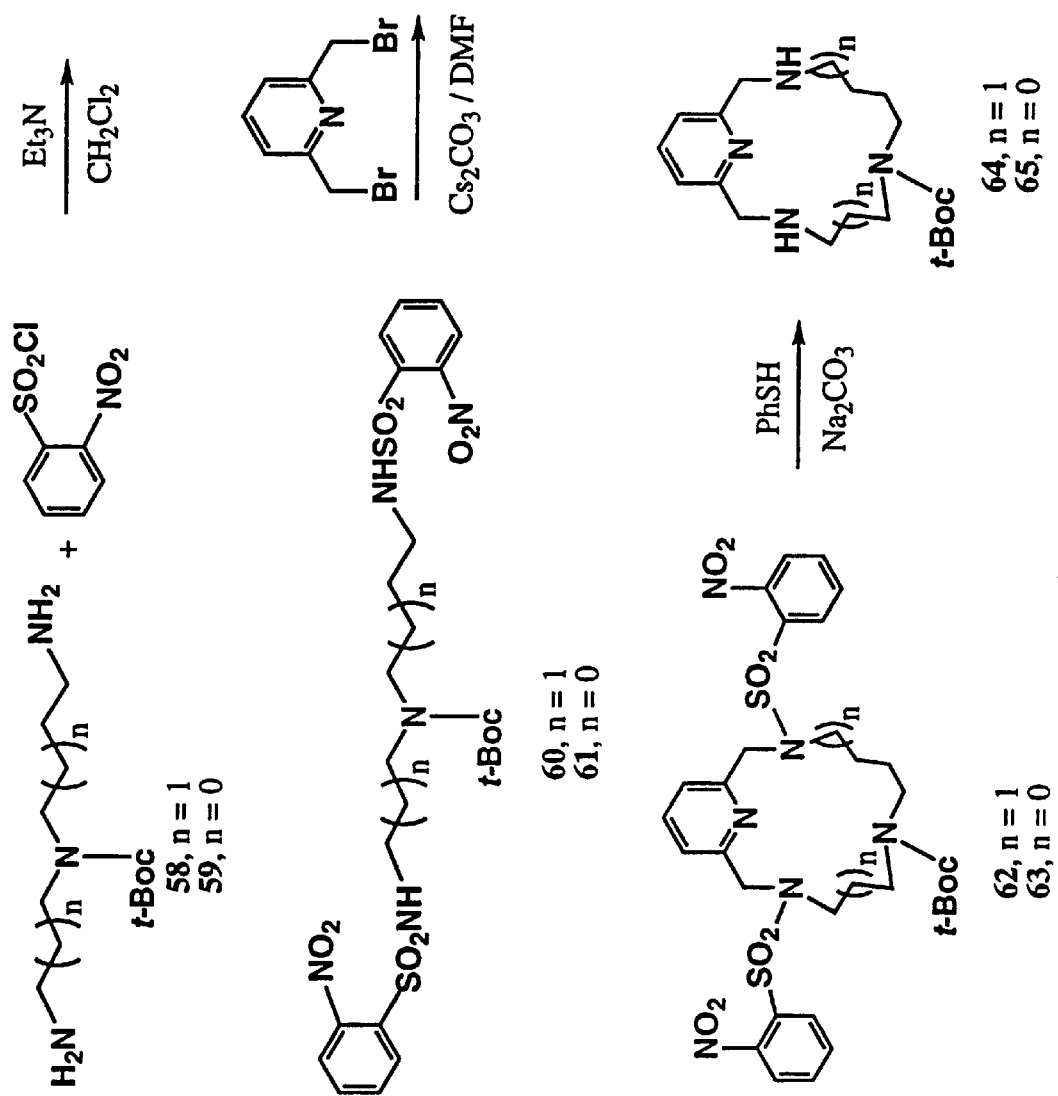
FIG. 11 is a synthetic scheme for the synthesis of a macrocyclic compound according to the invention and the processes for the preparation of libraries utilizing this macrocyclic compound.

EXAMPLE 107
N1-[N-(2-nitrobenzenesulfonyl)-3-aminopropan-1-yl]-N4-(2- nitrobenzenesulfonyl)-1,4-diaminobutane 60 (FIG. 11)

A solution of 2-nitrobenzenesulfonyl chloride (Aldrich, 5.32 g, 24 mmol, 2.4 eq) in dichloromethane (30 mL) was added dropwise to a stirred solution of N1-[t-Boc(3-aminopropyl)]-1,4-diaminobutane 58 (2.45 g, 10 mmol) and triethylamine (8 mL) in dichloromethane (30 mL) at 0° C. The resulting reaction mixture was allowed to warm to room temperature and further stirred for 1 hour. The mixture was diluted with chloroform and washed with water and brine. The organic phase was dried (Na$_2$SO$_4$) and the solvent was evaporated under reduced pressure. The residue was purified by flash chromatography on a silica gel column (20 cm×3 cm). Elution with hexanes:ethyl acetate (2:1 and 1:1, v/v) afforded 5.62 g (91%) of the title compound as a pale yellow sticky oil.

TLC: Rf 0.57;hexanes-ethyl acetate; 1:2, v/v; silica gel. $^1$H NMR (CDCl$_3$) δ 1.36 (s, 9H), 1.40–1.52 (m, 4 H), 1.58–1.74 (m, 2H), 2.98–3.25 (m, 8H), 5.45 (bs, 1H, disappeared in D$_2$O), 6.31 (bs, 1H, disappeared in D$_2$O), 7.65–7.85 (m, 6H), 8.00–8.11 (m, 2H). $^{13}$C NMR (CDCl$_3$) δ 25.37, 26.87, 28.35, 40.81, 43.45, 46.39, 79.92, 125.18, 125.33, 130.78, 130.94, 132.77, 132.92, 133.51, 133.79, 148.02, 156.00. Mass spectrum (HRFAB), m/z 748.075 (M+Cs)$^+$, (C$_{24}$H$_{33}$N$_5$O$_{10}$S$_2$Cs requires 748.072).

EXAMPLE 108
N1-[N-(2-nitrobenzenesulfonyl)-2-aminoethyl]-N3-(2-nitrobenzenesulfonyl)-1,3-diaminopropane 61 (FIG. 11)

A solution of 2-nitrobenzenesulfonyl chloride (Aldrich, 15.2 g, 68.2 mmol, 2.33 eq) in dichloromethane (90 mL) was added dropwise to a stirred solution of N1-[(t-Boc)-2-aminoethyl]-1,4-diaminopropane (6.35 g, 29.2 mmol) and triethylamine (24 mL) in dichloromethane (90 mL) at 0° C. The resulting reaction mixture was allowed to warm to room temperature and stirred for 1 hour. The mixture was diluted with chloroform and washed with water and brine. The organic phase was dried (Na$_2$SO$_4$) and the solvent was evaporated under reduced pressure. The residue was purified by flash chromatography on a silica gel column (20 cm×5 cm). Elution with hexanes:ethyl acetate (2:1 and 1:1, v/v) afforded 11.5 g (67%) of the title compound as a pale yellow sticky oil.

TLC: Rf 0.52; hexanes:ethyl acetate; 1:2, v/v; silica gel. $^1$H NMR (CDCl$_3$) δ 1.40 (s, 9H), 1.56–1.75 (m, 2H), 2.98–3.10 (m, 2H), 3.14–3.36 (m, 6H), 5.60 (bs, 1H, disappeared in D$_2$O), 6.20 (bs, 1H, disappeared in D$_2$O), 7.66–7.88 (m, 6H), 8.02–8.13 (m, 2H). $^{13}$C NMR (CDCl$_3$) δ 23.25, 40.68, 42.43, 44.18, 45.17, 46.89, 80.64, 125.32, 130.07, 132.94, 133.13, 133.99, 147.85, 156.07. Mass spectrum (HRFAB), m/z 720.039 (M+Cs)$^+$ (C$_{22}$H$_{29}$N$_5$O$_{10}$S$_2$Cs requires 720.041).

EXAMPLE 109
2,11-bis(2-nitrobenzenesulfonyl)diaza-7-(t-Boc)azadodecane-[2.6]pyridinophane 62 (FIG. 11)

A mixture of 2,6-bis(bromomethyl)pyridine (Aldrich, 1.33 g, 5.0 mmol), cesium carbonate (6.52 g, 29 mmol, 4 eq) and N1-[N-(2-nitrobenzenesulfonyl)-3-aminopropan-1-yl]-N4-(2- nitrobenzenesulfonyl)-1,4-diaminobutane (3.23 g, 5.0 mmol, 1 eq) in anhydrous DMF (160 mL) was stirred at room temperature for 24 hours. The solvent was evaporated under reduced pressure and the residue was dissolved in a mixture of water and chloroform. The layers were separated and the aqueous phase was extracted with chloroform. The organic extract was washed with brine, dried (Na$_2$SO$_4$) and concentrated. The residue was purified by flash chromatography on a silica gel column (18 cm×5 cm). Elution with hexanes: ethyl acetate (1:1, 1:2 and 1:4, v/v) gave 2.63 g (73%) of the title compound as a white foam.

TLC: Rf 0.48; hexanes:ethyl acetate; 1:4, v/v; silica gel. $^1$H NMR (CDCl$_3$) δ 1.15–1.30 (m, 4H), 1.36 (s, 9H), 1.58–1.74 (m, 2H), 2.98–3.10 (m, 4H), 3.16–3.40 (m, 4H), 4.48 (S, 2H), 4.62 (s, 2H), 7.43 (d, 2H, J=7.6 Hz), 7.61–7.78 (m, 7H), 7.98–8.10 (m, 2H). $^{13}$C NMR (CDCl$_3$) δ 26.14, 26.68, 28.37, 46.72, 47.00, 48.67, 48.84, 53.69, 54.42, 79,60, 122.58, 122.85, 124,27, 130.77, 131.83, 133.77, 138.06, 148.24, 155.67, 156.00, 156.12. Mass spectrum (HRFAB), m/z 851.118 (M+Cs)$^+$ (C$_{31}$H$_{38}$N$_6$O$_{10}$S$_2$Cs requires 851.115).

EXAMPLE 110
2,9-bis(2-nitrobenzenesulfonyl)diaza-6-(t-Boc)azadecane-[2.6]pyridinophane 63 (FIG. 11)

The title compound was synthesized following the procedure of Example 109 using 2,6-bis(bromomethyl)pyridine (4.93 g, 18.6 mmol), cesium carbonate (24 g, 73.6 mmol) and (10.98 g, 18.6 mmol) of N1-[N-(2-nitrobenzenesulfonyl)-2- aminoethyl)-N3-(2-nitrobenzenesulfonyl)-1,3-diaminopropane in anhydrous DMF (500 mL). After purification by flash chromatography, 10.3 g (80%) of the title compound was obtained as a white foam.

TLC: Rf 0.50; hexanes:ethyl acetate; 1:4, v/v; silica gel. $^1$H NMR (CDCl$_3$) δ 1.40 (s, 9H), 1.67–1.85 (m, 2H), 2.60–2.80 (m, 2H), 3.04–3.15 (m, 2H), 3.25–3.46 (m, 4H), 4.55 (s, 4H), 7.48–7.80 (m, 9H), 7.96–8.10 (m, 2H). $^{13}$C NMR (CDCl$_3$) δ 26.98, 28.34, 45.36, 46.40, 47.07, 49.26, 55.24, 55.65, 79.83, 123.97, 124.25, 124.41, 130.67, 130.92, 131.91, 133.98, 138.64, 148.13, 148.36, 155.06, 155.67. Mass spectrum (HRFAB), m/z 823.086 (M+Cs)$^+$ (C$_{29}$H$_{34}$N$_6$O$_{10}$S$_2$Cs requires 823.083).

EXAMPLE 111
2,11-diaza-7-(t-Boc)azadodecane[2.6]pyridinophane 64 (FIG. 11)

Thiophenol (Aldrich, 500 μL, 0.53 g, 4.8 mmol, 2.4 eq) was added to a stirred mixture 2,11-bis(2-nitrobenzenesulfonyl)diaza-7-(t-Boc)azadodecane[2.6]pyridinophane (1.44 g, 2.0 mmol) and potassium carbonate (2.21 g, 16 mmol, 8 eq.) in DMF (30 mL). The resulting blue mixture was stirred at room temperature for 2 hours. The yellow reaction mixture was concentrated under reduced pressure and the residue was dissolved in water. The solution was made basic (e.g. pH 13–14) with aqueous sodium hydroxide and extracted with chloroform. The organic extract was washed with brine, dried (Na$_2$SO$_4$) and the solvent was evaporated. The residue was purified by flash chromatography on a silica gel column (18 cm×3 cm). Elution with methanol and methanol:30% aqueous ammonium hydroxide (100:1 and 50:1, v/v) afforded 0.50 g (72%) of the title compound as a colorless oil.

TLC: Rf 0.44; methanol:30% aqueous ammonium hydroxide; 50:1, v/v; silica gel. $^1$H NMR (CDCl$_3$) δ 1.37 (s, 9H), 1.42–1.58 (m, 4H), 1.65–1.80 (m, 2H), 2.22 (bs, 2H, disappeared in D$_2$O), 2.53 (t, 2H, J=5.2 Hz), 2.62 (t, 2H, J=6.2 Hz), 2.95–3.09 (m, 2H), 3.21 (t, 2H, J=6.2 Hz), 3.85 (s, 4H), 6.99 (t, 2H, J=7.4 Hz), 7.50 (t, 1H, J=7.4 Hz). $^{13}$C NMR (CDCl$_3$) δ 24.90, 26.22, 28.45, 29.41, 45.00, 46.16, 46.50, 47.35, 54.10, 54.46, 79.03, .120.81, 121.06, 136.56, 155.57, 159.42. Mass spectrum (HRFAB), m/z 349.261 (M+H)$^+$ (C$_{19}$H$_{33}$N$_4$O$_2$ requires 349.260). (All above procedures are real).

Figure 12:
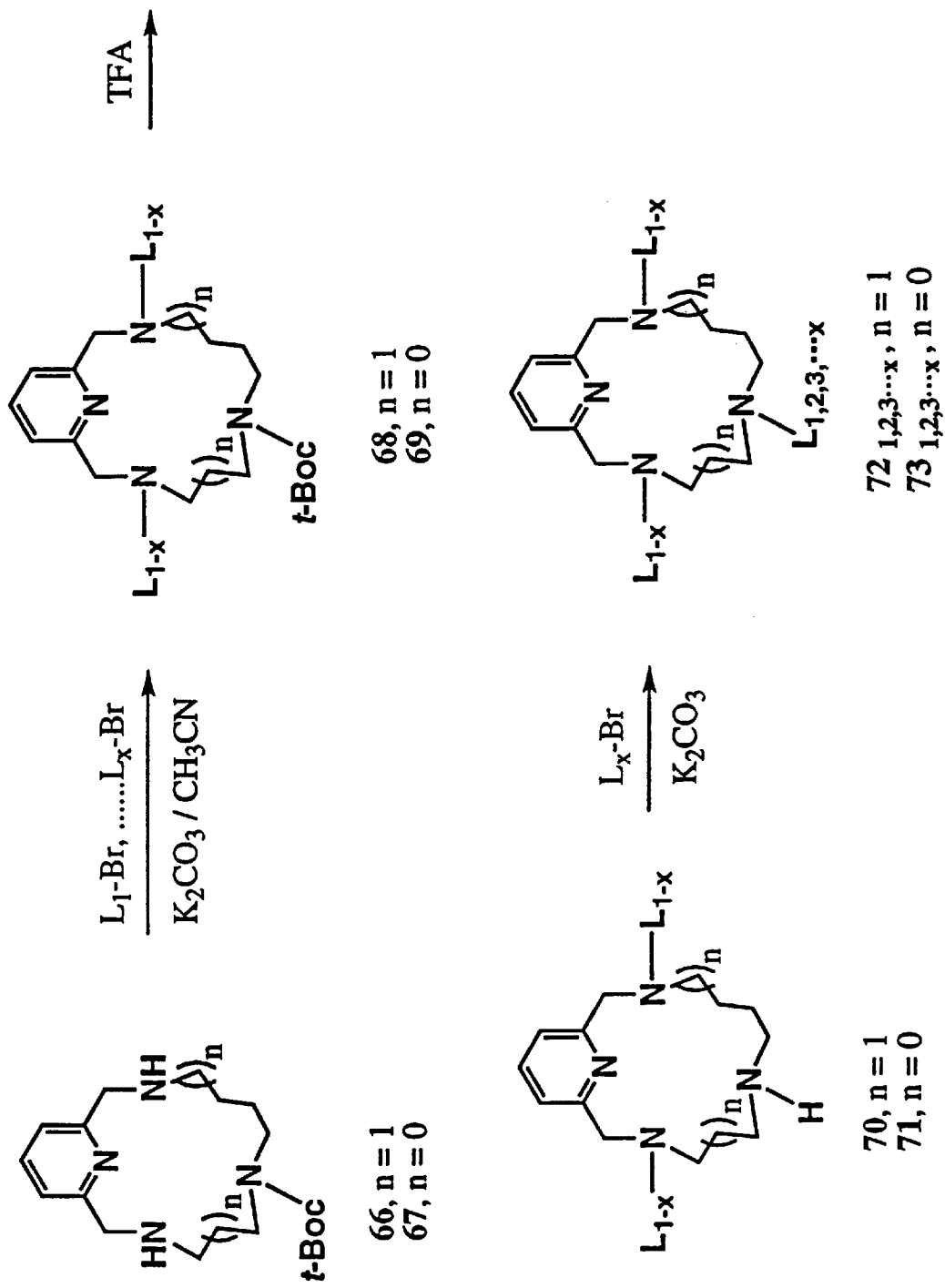
FIG. 12 shows processes for a first round of synthesis for preparing libraries of compounds according to the invention.

EXAMPLE 112
Preparation of t-Boc protected library 68 (FIG. 12)

A solution of benzyl bromide (123 μL, 171 mg, 1.0 mmol), 3-fluorobenzylbromide (124 μL, 189 mg, 1.0 mmol), α-bromo-m-xylene (141 μL, 185 mg, 1.0 mmol), methyl 3-bromomethylbenzoate (229 mg, 1.0 mmol), 3-nitrobenzyl bromide (216 mg, 1.0 mmol), α'-bromo-α,α,α-trifluoro-m-xylene (155 μL, 239 mg, 1.0 mmol), 3-(bromomethyl)benzonitrile (196 mg, 1.0 mmol), cinnamyl bromide (148 μL, 197 mg, 1.0 mmol), 3-chloro-benzyl bromide (132 μL, 205 mg, 1.0 mm), and 3-bromobenzyl bromide (250 mg, 1.0 mm) in acetonitrile (40 mL) is added to a stirred mixture of 2,11-diaza-7-(t-Boc)azadodecane-[2.6]pyridinophane (1.05 g, 3.0 mmol) and potassium carbonate (6.0 g, 43 mmol) in acetonitrile (100 mL). The resulting reaction mixture is stirred at room temperature overnight. After the solvent is evaporated the residue is dissolved in water and chloroform. The layers are separated and the aqueous layer is extracted with chloroform. The combined chloroform extract is washed with brine and dried (Na$_2$SO$_4$). The solvent is evaporated and the residue is purified by flash chromatography on a silica gel column. Elution with 5:1 hexanes-ethyl acetate and then 100% ethyl acetate will afford the t-boc protected library.

EXAMPLE 113
Deprotection of Library 68, Preparation of Library 70 (FIG. 12)

Trifluoroacetic acid (TFA) (16 mL) is added to a flask containing 1.50 g (2.1 mmol) of Library 68 at 0° C. The resulting solution is stirred at room temperature for 3 hours. The TFA is evaporated under reduced pressure and the residue is dissolved in chloroform (300 mL). The solution is washed 3 times with saturated aqueous potassium carbonate solution and dried (Na$_2$SO$_4$). The solvent is evaporated and the residue is purified by flash chromatography on a silica gel column. Elution with 100% methanol and then 100:1 methanol-30% aqueous ammonium hydroxide will afford the deprotected library 70.

EXAMPLE 114
Preparation of Library 72 (FIG. 12)

A solution of benzyl bromide derivative (0.25 mmol) in 2 mL of acetonitrile is added at room temperature to a stirred mixture of Library 70 (0.15 mmol) and potassium carbonate (0.4 g, 2.8 mmol) in acetonitrile (6 mL). The resulting reaction mixture is stirred at room temperature for 24 hours. The solvent is evaporated under reduced pressure and the residue is dissolved in water-chloroform. The layers are separated and the aqueous layer is extracted with chloroform. The combined chloroform extract is dried ($Na_2SO_4$) and the solvent is evaporated. The residue is purified by preparative thin layer chromatography (TLC) using 40:1 ethyl acetate-methanol as developing agent to afford Library 72 (FIG. 12).

EXAMPLE 115

Figure 13:
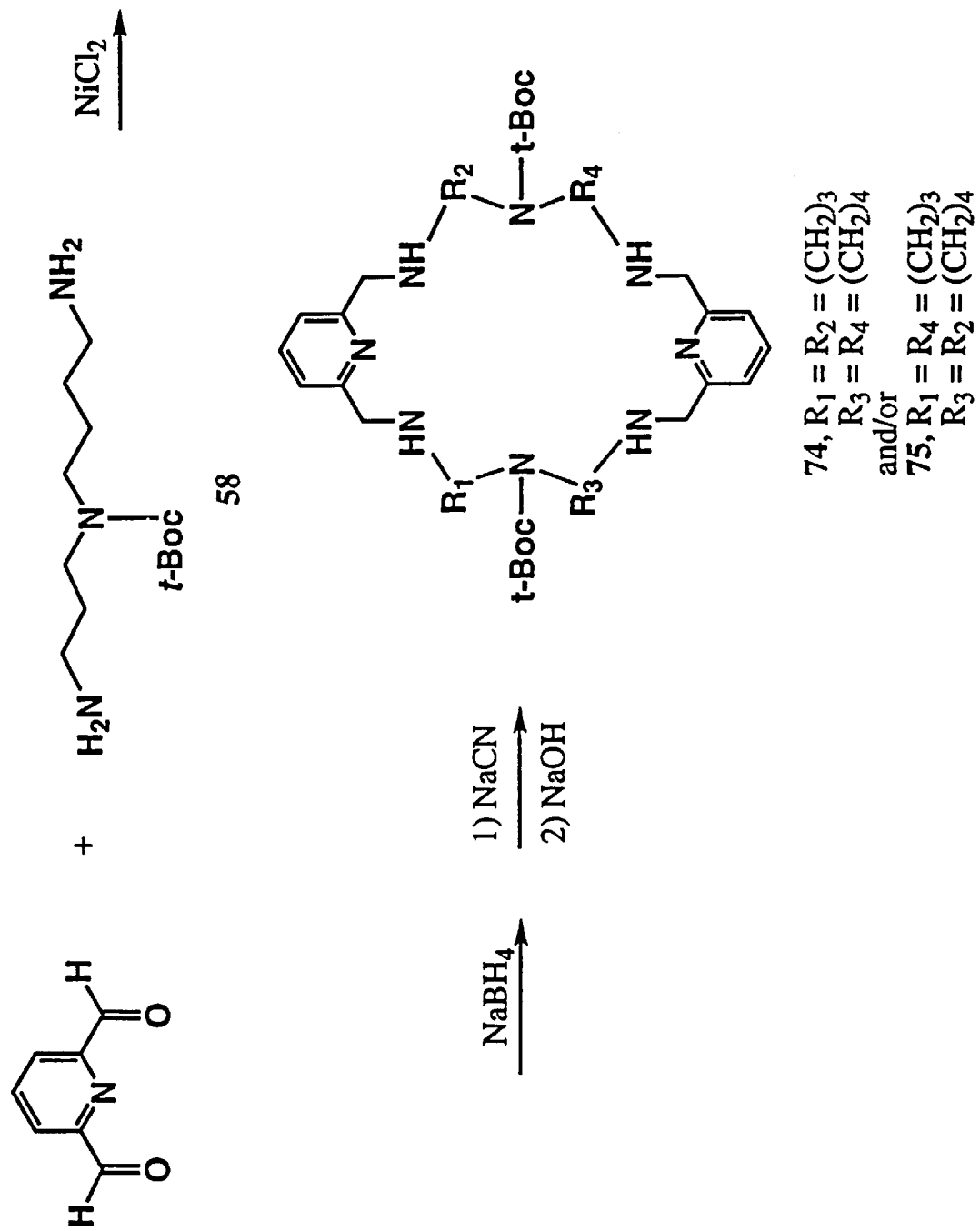
FIG. 13 is a synthetic scheme for the synthesis of macrocyclic compounds according to the invention.

Preparation of 2,6,11,20,25,29-hexaaza-6,25-bis(t-Boc)-[12.12](2,6)pyridinophane 74; and 2,7,11,20,25,29-hexaaza- 7,25-bis(t-Boc)-[12.12](2,6)pyridinophane 75 (FIG. 13)

A solution of N1-[t-Boc(3-aminopropyl)]-1,4-diaminobutane 58 (3.64 g, 14.8 mmol) in ethanol (15 mL) was added to a stirred solution of nickel (II) chloride hexahydrate (3.52 g, 14.8 mmol) in ethanol-water (80 mL, 1:1, v/v). Pyridine-2,6-dicarboxaldehyde (2.0 g, 14.8 mmol) was added to the above blue solution followed by glacial acetic acid (1.35 mL). The resulting deep blue solution was stirred at room temperature for 2 hours and then at 80° C. for 6 hours. The solution was cooled to 0° C. and then sodium borohydride (5.0 g, 0.132 mol) was added in portions. The reaction mixture was stirred at room temperature overnight and at 80° C. for 2 hours. The cooled reaction mixture was concentrated under reduced pressure to remove ethanol. The reaction mixture was diluted with water (40 mL) and sodium cyanide (7.0 g, 0.142 mol) was added. The resulting mixture was stirred at 80° C. for 1 hour. The cooled reaction mixture was basified to pH 13–14 with aqueous sodium hydroxide solution and then extracted with chloroform. The chloroform extract was washed with brine and dried over anhydrous sodium sulfate. The solvent was evaporated under reduced pressure and the residue was purified by flash chromatography on a silica gel column (22 cm×3 cm). Elution with 100% methanol followed by methanol:30% aqueous ammonium hydroxide (100:1 and 50:1, v/v) gave 0.35 g (6.8%) of the tile compounds 74 and 75 as a pale yellow oil.

TLC: Rf 0.48; methanol:30% aqueous ammonium hydroxide; 20:1, v/v; silica gel. $^1$H NMR ($CDCl_3$) δ 1.39 (s, 18H), 1.40–1.55 (m, 8H), 1.60–1.78 (m, 4H), 2.50–2.68 (m, 8H), 3.05–3.25 (m, 8H), 3.81 (s, 8H), 7.00–7.18 (m, 4H), 7.47–7.60 (m, 2H). Mass spectrum (electrospray), m/z 697 (M+1)$^+$.

EXAMPLE 116

Preparation of 2,9-diaza-6-(t-Boc)azadecane[2.6]pyridinophane

Thiophenol (Aldrich, 1.5 mL, 1.6 g, 14.5 mmol, 2.46 eq.) was added to a stirred mixture of 2,9-bis(2-nitrobenzenesulfonyl)diaza-6-(t-Boc)azadecane[2.6]pyridinophane (4.15 g, 6.0 mmol) and potassium carbonate (6.63 g, 48 mmol, 8 eq) in DMF (80 mL). The resulting blue mixture was stirred at room temperature for 2 hours. The yellow reaction mixture was concentrated under reduced pressure and the residue was dissolved in water. The solution was made basic (e.g. pH 13–14) with aqueous sodium hydroxide and extracted with chloroform. The organic extract was washed with brine, dried ($Na_2SO_4$), filtered, and the solvent evaporated. The residue was purified by flash chromatography on a silica gel column (20 cm×3 cm). Elution with methanol and methanol:30% aqueous ammonium hydroxide (100:1 and 50:1, v/v) afforded 1.81 g (94%) of the title compound as a colorless oil.

TLC: Rf 0.42; methanol:30% aqueous ammonium hydroxide; 50:1, v/v; silica gel. $^1$H NMR ($CDCl_3$) δ 1.35 (s, 9H), 1.48–1.65 (m, 2H), 2.19 (bs, 2H, disappeared in $D_2O$), 2.62 (t, 2H, J=6.4 Hz), 2.78 (t, 2H, J=6.2 Hz), 3.00 (t, 2H, J=6.2 Hz), 3.28 (t, 2H, J=6.4 Hz), 3.90 (s, 4H), 7.04 (t, 2H, J=7.0 Hz), 7.56 (t, 1H, J=7.0 Hz). $^{13}$C NMR ($CDCl_3$) δ 28.43, 29.89, 46.09, 46.39, 48.31, 48.60, 54.25, 54.67, 79.25, 120.91, 121.31, 137.14, 156.04, 159.95, 160.11. Mass spectrum (HRFAB), m/z 321.230 (M+H)$^+$ ($C_{17}H_{29}N_4O_2$ requires 321.229).

EXAMPLE 117

Figure 14:
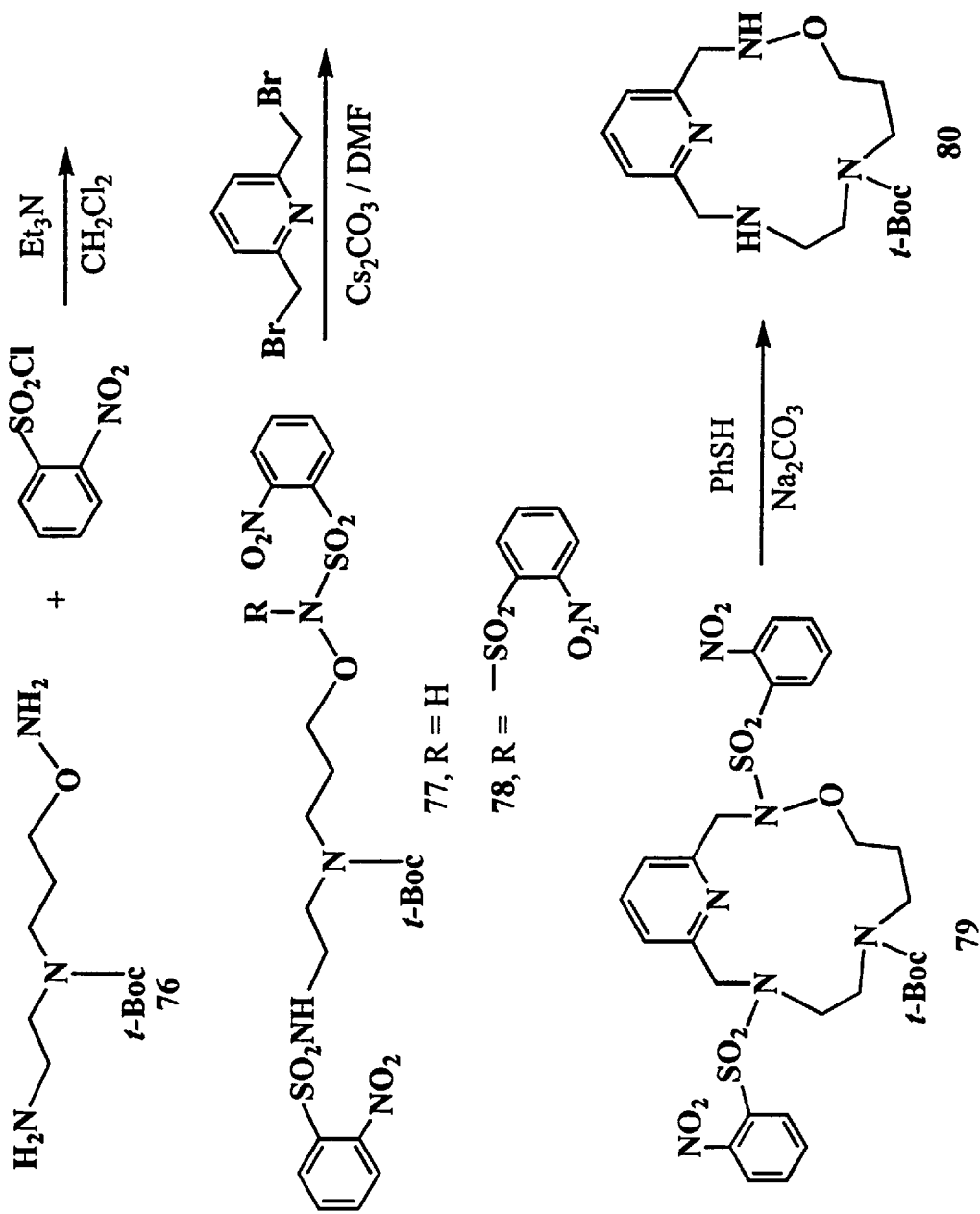
FIG. 14 is a synthetic scheme for the synthesis of macrocyclic compounds according to the invention.

N1[(t-Boc)-3-((N-o-nitrophenylsulfonyl)O-amino)propanol-1-yl]- N2-(o-nitrophenylsulfonyl)diaminoethane 77 and N1[(t-Boc)-3- ((N-o-nitrophenylsulfonyl)O-amino)propanol-1-yl]-N2-(bis-o- nitrophenylsulfonyl)diaminoethane 78 (FIG. 14)

A solution of 2-nitrobenzenesulfonyl chloride (Aldrich, 10.64 g, 47.0 mmol, 2.3 eq) in dichloromethane (60 mL) was added dropwise to a stirred solution of N1[(t-Boc)-3-(O-amino)propanol-1-yl]diaminoethane (Example 12) (4.67 g, 20.0 mmol) and triethylamine (16 mL) in dichloromethane (80 mL) at 0° C. The resulting reaction mixture was allowed to warm to room temperature and further stirred for 2 hours. The mixture was diluted with chloroform and washed with water and brine. The organic phase was dried ($Na_2SO_4$) and the solvent was evaporated under the reduced pressure. The residue was purified by flash chromatography on a silica gel column (20 cm×6 cm). Elution with hexanes:ethyl acetate (2:1 and 1:1, v/v) afforded 3.95 g (33%) of the title compound 77 as a white foam and 7.13 g (45%) of of the title compound 78 as a white foam.

Compound 77: TLC: Rf 0.62; hexanes:ethyl acetate; 1:2, v/v; silica gel. $^1$H NMR ($CDCl_3$) δ 1.40 (s, 9H), 1.72–1.90 (m, 2H), 3.18–3.41 (m, 6H), 3.98–4.11 (m, 2H), 7.68–7.90 (m, 6H), 8.10–8.25 (m, 2H). Mass spectrum (HRFAB), m/z 736.035 (M+Cs)$^+$ ($C_{22}H_{29}N_5O_{11}S_2Cs$ requires 736.035).

Compound 78: TLC: Rf 0.49; hexanes-ethyl acetate; 1:2, v/v; silica gel. $^1$H NMR ($CDCl_3$) δ 1.42 (s, 9H), 1.75–1.92 (m, 2H), 3.10–3.42 (m, 6H), 4.10–4.22 (m, 2H), 7.68–7.90 (m, 9H), 8.05–8.25 (m, 3H). Mass spectrum (Electrospary), m/z 787 (M–1)$^+$.

EXAMPLE 118

Preparation of 2,10-(bis-o-nitrophenylsulfonyl)-7-(N-t-Boc)- 2,7,10-triaza-3-oxaundecane)[11](2,6)-pyridinophane 79 (FIG. 14)

A mixture of 2,6-bis(bromomethyl)pyridine (Aldrich, 1.66 g, 6.2 mmol), cesium carbonate (8.2 g, 25 mmol, 4 eq) and N1[(t-Boc)-3-((N-o-nitrophenylsulfonyl)O-amino)propanol-1-yl]-N2-(o-nitrophenylsulfonyl)diaminoethane 77 (3.80 g, 6.2 mmol, 1 eq) in anhydrous DMF (200 mL) was stirred at room temperature for 23 hours. The solvent was evaporated under reduced pressure and the residue was dissolved in a mixture of water and chloroform. The layers were separated and the aqueous phase was extracted with chloroform. The organic extract was washed with brine, dried ($Na_2SO_4$) and concentrated. The residue was purified by flash chromatography on a silica gel column (22 cm×3 cm). Elution with hexanes:ethyl acetate (1:1 and 1:2, v/v) gave 2.20 g (50%) of the title compound as a white foam.

TLC: Rf 0.55; hexanes:ethyl acetate; 1:4, v/v; silica gel. $^1$H NMR ($CDCl_3$) δ 1.20–1.30 (m, 2H), 1.38 (s, 9H), 2.60–3.00 (m, 2H), 3.16–3.40 (m, 2H), 3.78–3.95 (m, 2H), 4.30 (s, 2H), 4.55 (s, 2H), 7.50–7.78 (m, 9H), 7.85–8.10 (m, 2H). Mass spectrum (HRFAB), m/z 839.078 (M+Cs)$^+$ ($C_{29}H_{34}N_6O_{11}S_2Cs$ requires 839.078).

EXAMPLE 119
7-(N-t-Boc)-2,7,10-triaza-3-oxaundecane)[11](2,6)- pyridinophane 80 (FIG. 14)

Thiophenol (Aldrich, 158 μL, 169 mg, 1.53 mmol, 2.2 eq) was added to a stirred mixture of 2,10-(bis-o-nitrophenylsulfonyl)-7-(N-t-Boc)-2,7,10-triaza-3-oxaundecane)[11](2,6)- pyridinophane (495 mg, 0.7 mmol) and potassium carbonate (0.80 g, 5.7 mmol) in DMF (10 mL). The resulting blue mixture was stirred at room temperature for 2 hours. The yellow reaction mixture was concentrated under reduced pressure and the residue was dissolved in water. The solution was made basic (e.g. pH 13–14) with aqueous sodium hydroxide and extracted with chloroform. The organic extract was washed with brine, dried ($Na_2SO_4$) and the solvent was evaporated. The residue was purified by flash chromatography on a silica gel column (13 cm×2 cm). Elution with hexanes:ethyl acetate (5:1 and 1:1, v/v) and then 100% ethyl acetate afforded 230 mg (97%) of the title compound as a colorless oil.

TLC: Rf 0.50; 100% methanol; silica gel. $^1$H NMR (CDCl$_3$) δ 1.34 (s, 9H), 1.45–1.65 (m, 2H), 2.65 (t, 2H, J=6.8 Hz), 2.97 (t, 2H, J=7.2 Hz), 3.14 (t, 2H, J=6.8 Hz), 3.58 (t, 2H, J=6.0 Hz), 3.92 (s, 2H), 4.05 (s, 2H), 7.09 (t, 2H, J=7.2 Hz), 7.56 (t, 1H, J=7.2 Hz). $^{13}$C NMR (CDCl$_3$) δ 27.78, 28.43, 43.97, 45.88, 47.32, 54.39, 57.11, 70.57, 79.27, 121.72, 121.87, 137.01, 155.72, 157.88, 159.25. Mass spectrum (HRFAB), m/z 337.224 (M+H)$^+$ ($C_{17}H_{29}N_4O_3$ requires 337.224).

EXAMPLE 120
Diethyl-4-piperazinyl-2,6-pyridinedicarboxylate

A mixture of diethyl 4-bromopyridine-2,6-dicarboxylate (Example 44) (3.02 g, 10.0 mmol) and piperazine (Aldrich, 4.3 g, 50 mmol) in dioxane (200 mL) was refluxed for 24 hours. The precipitate was filtered off and the filtrate was concentrated under vacuum. The residue was dissolved in ethyl acetate and washed four times with brine. The organic solution was dried (Na$_2$SO4) and the solvent was evaporated. The residue was purified by flash chromatography on a silica gel column (22 cm×3 cm). Elution with methanol and then methanol:30% ammonium hydroxide (100:1, 50:1, and 20:1, v/v) gave 3.05 g (99 %) of the title compound as a pale yellow foam.

TLC: Rf 0.35; methanol:30 % ammonium hydroxide; 100:1, v/v; silica gel. $^1$H NMR (CDCl$_3$) δ 1.45 (t, 6H, J=7.2 Hz), 1.73 (bs, 1H), 2.95–3.06 (m, 4H), 3.38–3.50 (m, 4H), 4.44 (q, 4H, J=7.2 Hz), 7.63 (s, 2H). $^{13}$C NMR (CDCl$_3$) δ 14.18, 45.53, 46.96, 62.16, 111.34, 149.25, 156.37, 165.62. Mass spectrum (HRFAB), m/z 308.162, (m+1)$_+$ ($C_{15}H_{22}O_4N_3$ requires 308.161).

EXAMPLE 121
4-piperazinyl-2,6-bis-hydroxymethyl pyridine

Diethyl-4-piperazinyl-2,6-pyridinedicarboxylate is dissolved in THF and treated with NaBH$_4$ and CaCl$_2$. Brine is added and the organic phase is separated. The organic phase is washed with brine, dried (Na$_2$SO$_4$) and the solvent is evaporated. The residue is purified by flash chromatography on a silica gel column to give the title compound.

EXAMPLE 122
4-piperazinyl-2,6-bis-dibromopyridine 4-piperazinyl-2,6-bis-hydroxymethyl pyridine is dissolved in acetic acid and treated with an excess of phosphorous tribromide. The reaction mixture is neutralized with aqueous sodium carbonate and the organic phase is separated. The organic phase is washed with brine, dried (Na$_2$SO$_4$) and the solvent is evaporated. The residue is purified by flash chromatography on a silica gel column to give the title compound.

EXAMPLE 123
4-(N4-CBZ-piperazine-1-yl)-2,6-bis-dibromopyridine 4-piperazinyl-2,6-bis-dibromopyridine and triethyl amine is dissolved in chloroform and treated with an excess of benzyl chloroformate. The reaction mixture is washed with water and brine. The organic phase is dried (Na$_2$SO$_4$) and the solvent is evaporated. The residue is purified by flash chromatography on a silica gel column to give the title compound.

EXAMPLE 124
Preparation of 2,10-(bis-o-nitrophenylsulfonyl)-7-(N-t-Boc)- 2,7,10-triaza-3-oxaundecane)[11](2,6)-[4-(N4-CBZ-piperazine-1-yl)pyridinophane]

A mixture of 4-(N4-CBZ-piperazine-1-yl)-2,6-bis-dibromopyridine (6.2 mmol), cesium carbonate (25 mmol, 4 eq) and N1[(t-Boc)-3-((N-o-nitrophenylsulfonyl)O-amino)propanol-1-yl]-N2-(o-nitrophenylsulfonyl)diaminoethane 77 (3.80 g, 6.2 mmol, 1 eq) in anhydrous DMF (200 mL) is stirred at room temperature for 23 hours. The solvent is evaporated under reduced pressure and the residue is dissolved in a mixture of water and chloroform. The layers are separated and the aqueous phase is extracted with chloroform. The organic extract is washed with brine, dried (Na$_2$SO$_4$) and concentrated. The residue is purified by flash chromatography on a silica gel column to give the title compound.

EXAMPLE 125
7-(N-t-Boc)-2,7,10-triaza-3-oxaundecane)[11](2,6)-[4-(N4-CBZ- piperazine-1-yl)pyridinophane]

Thiophenol (Aldrich, 158 mL, 169 mg, 1.53 mmol, 2.2 eq) is added to a stirred mixture of 2,10-(bis-o-nitrophenylsulfonyl)-7-(N-t-Boc)-2,7,10-triaza-3-oxaundecane)-[11](2,6)-[4-(N4-CBZ-piperazine-1-yl)pyridinophane] (0.7 mmol) and potassium carbonate (0.80 g, 5.7 mmol) in DMF (10 mL). The resulting mixture is stirred at room temperature for 2 hours. The reaction mixture is concentrated under reduced pressure and the residue is dissolved in water. The solution is made basic (e.g. pH 13–14) with aqueous sodium hydroxide and extracted with chloroform. The organic extract is washed with brine, dried (Na$_2$SO$_4$) and the solvent is evaporated. The residue is purified by flash chromatography on a silica gel column to give the title compound.

EXAMPLE 126
Preparation of t-Boc and CBZ protected library using 7-(N-t- Boc)-2,7,10-triaza-3-oxaundecane)(11](2,6)-[4-(N4-CBZ- piperazine-1-yl)pyridinophane] Library 126

A solution of benzyl bromide (123 ∥L, 171 mg, 1.0 mmol), 3-fluorobenzylbromide (124 μL, 189 mg, 1.0 mmol), α-bromo-m-xylene (141 μL, 185 mg, 1.0 mmol), methyl 3-bromomethylbenzoate (229 mg, 1.0 mmol), 3-nitrobenzyl bromide (216 mg, 1.0 mmol), α'-bromo-α,α,α-trifluoro-m-xylene (155 μL, 239 mg, 1.0 mmol), 3-(bromomethyl)benzonitrile (196 mg, 1.0 mmol) and cinnamyl bromide (148 μL, 197 mg, 1.0 mmol) in acetonitrile (40 mL) is added to a stirred mixture of 7-(N-t- Boc)-2,7,10-triaza-3-oxaundecane)[11](2,6)--[4-(N4-CBZ- piperazine-1-yl)pyridinophane] (3.0 mmol) and potassium carbonate (6.0 g, 43 mmol) in acetonitrile (100 mL). The resulting reaction mixture is stirred at room temperature overnight. After the solvent is evaporated the residue is dissolved in water and chloroform. The layers are separated and the aqueous layer is extracted with chloroform. The combined chloroform extract is washed with brine and dried ($Na_2SO_4$). The solvent is evaporated and the residue is purified by flash chromatography on a silica gel column to afford the t-boc and CBZ protected library.

EXAMPLE 127
Deprotection of Library 126, Preparation of Library 127

Trifluoroacetic acid (TFA) (16 mL) is added to a flask containing (2.1 mmol) of Library 126 at 0 ° C. The resulting solution is stirred at room temperature for 3 hours. The TFA is evaporated under reduced pressure and the residue is dissolved in chloroform (300 mL). The solution is washed 3 times with saturated aqueous potassium carbonate solution and dried ($Na_2SO_4$). The solvent is evaporated and the residue is purified by flash chromatography on a silica gel column. Elution with 100% methanol and then 100:1 methanol-30% aqueous ammonium hydroxide will afford the deprotected library 127.

EXAMPLE 128
Preparation of Library 128

A solution of benzyl bromide (123 µL, 171 mg, 1.0 mmol), 3-fluorobenzylbromide (124 µL, 189 mg, 1.0 mmol), α-bromo-m-xylene (141 µL, 185 mg, 1.0 mmol), methyl 3-bromomethylbenzoate (229 mg, 1.0 mmol), 3-nitrobenzyl bromide (216 mg, 1.0 mmol), α'-bromo-α,α,α-trifluoro-m-xylene (155 µL, 239 mg, 1.0 mmol), 3-(bromomethyl) benzonitrile (196 mg, 1.0 mmol) and cinnamyl bromide (148 µL, 197 mg, 1.0 mmol) in acetonitrile (40 mL) is added to a stirred mixture of Library 127 (3.0 mmol) and potassium carbonate (6.0 g, 43 mmol) in acetonitrile (100 mL). The resulting reaction mixture is stirred at room temperature overnight. After the solvent is evaporated the residue is dissolved in water and chloroform. The layers are separated and the aqueous layer is extracted with chloroform. The combined chloroform extract is washed with brine and dried ($Na_2SO_4$). The solvent is evaporated and the residue is purified by flash chromatography on a silica gel column. Elution with 5:1 hexanes-ethyl acetate and then 100% ethyl acetate will afford the CBZ protected library.

EXAMPLE 129
Deprotection of Library 128, preparation of Library 129

Hydrogen bromide in acetic acid (40%) is added to a flask containing (2.1 mmol) of Library 128 at 0° C. The resulting solution is stirred at room temperature for 3 hours. The reaction mixture is diluted with water and neutralized with aqueous sodium carbonate and then extracted with chloroform. The organic extrac is dried ($Na_2SO_4$) the solvent is evaporated and the resulting residue is purified by flash chromatography on a silica gel column. Elution with 100% methanol and then 100:1 methanol-30% aqueous ammonium hydroxide will afford the deprotected library 129.

EXAMPLE 130
Preparation of Library 130

Library 129 is divided into 8 different pools and each of the pools is treated as per the procedure of Example 128 with a single letter. The resulting libraries $XX_{1-8}$ will each have a fixed letter on the piperazine nitrogen and 3 combinatorialized positions having one of eight letters at each of these positions. The eight fixed letters are benzyl bromide, 3-fluorobenzylbromid, α-bromo-m-xylene, methyl 3-bromomethylbenzoate, 3-nitrobenzyl bromide, α'-bromo-α,α,α-trifluoro-m-xylene, 3-(bromomethyl)benzonitrile, and cinnamyl bromide. After workup and purification as per Example 128 the rusulting libraries $130_{1,2,3,4,5,6,7, \text{ and } 8}$ are obtained.

EXAMPLE 131
Preparation of 2,10-(bis-o-nitrophenylsulfonyl)-7-(N-t-Boc)- 2,7,10-triaza-3-oxaundecane)[11](2,6)-cyclophane A mixture of α,α'-dibromo-m-xylene (Aldrich, 1.64 g, 6.2 mmol), cesium carbonate (8.2 g, 25 mmol, 4 eq) and N1[(t-Boc)-3-((N-o-nitrophenylsulfonyl)O-amino)propanol-1-yl]-N2-(o- nitrophenylsulfonyl)diaminoethane 77 (3.80 g, 6.2 mmol, 1 eq) in anhydrous DMF (200 mL) is stirred at room temperature for 23 hours. The solvent is evaporated under reduced pressure and the residue is dissolved in a mixture of water and chloroform. The layers are separated and the aqueous phase is extracted with chloroform. The organic extract is washed with brine, dried ($Na_2SO_4$) and concentrated. The residue is purified by flash chromatography on a silica gel column to give the title compound.

EXAMPLE 132
Preparation of 7-(N-t-Boc)-2,7,10-triaza-3-oxaundecane)-(11](2,6)-cyclophane The title compound is prepared as per the procedure of Example 111, using the title compound of Example 132.

EXAMPLE 133
2,11-bis(2-nitrobenzenesulfonyl)diaza-7-(t-Boc) azadodecane- [2.6 ]cyclophane A mixture of α,α'-dibromo-m-xylene (Aldrich, 1.64 g, 6.2 mmol), cesium carbonate (8.2 g, 25 mmol, 4 eq) and N1-[N-(2-nitrobenzenesulfonyl)-2-aminoethyl]-N3-(2-nitrobenzene- sulfonyl)-1,3-diaminopropane (Example 108) (3.64 g, 6.2 mmol, 1 eq) in anhydrous DMF (200 mL) is stirred at room temperature for 23 hours. The solvent is evaporated under reduced pressure and the residue is dissolved in a mixture of water and chloroform. The layers are separated and the aqueous phase is extracted with chloroform. The organic extract is washed with brine, dried ($Na_2SO_4$) and concentrated. The residue is purified by flash chromatography on a silica gel column to give the title compound.

EXAMPLE 134
2,7,11-triaza-7-(N-t-Boc)-dodecane[2.6]cyclophane

The title compound is prepared as per the procedure of Example 111, using the title compound of Example 133.

EXAMPLE 135
2,11-bis(2-nitrobenzenesulfonyl)diaza-7-(t-Boc) azadodecane- [2.6]cyclophane A mixture of α,α'-dibromo-m-xylene (Aldrich, 1.64 g, 6.2 mmol), cesium carbonate (8.2 g, 25 mmol, 4 eq) and N1-[N-(2-nitrobenzenesulfonyl)-3-aminopropan-1-yl]-N4-(2-nitrobenzenesulfonyl)-1,4-diaminobutane (Example 107) (3.81 g, 6.2 mmol, 1 eq) in anhydrous DMF (200 mL) is stirred at room temperature for 23 hours. The solvent is evaporated under reduced pressure and the residue is dissolved in a mixture of water and chloroform. The layers are separated and the aqueous phase is extracted with chloroform. The organic extract is washed with brine, dried ($Na_2SO_4$) and concentrated. The residue is purified by flash chromatography on a silica gel column to give the title compound.

EXAMPLE 136
2,7,11-triaza-7-N-(t-Boc)azadodecane[2.6]cyclophane

The title compound is prepared as per the procedure of Example 111, using the title compound of Example 135.

EXAMPLE 137
Preparation of cis-1,2-bis-(bromomethyl)cyclohexane cis-1,2-Cyclohexandimethanol is treated with $PBr_3$ in $CCl_4$ at 0° C. for 2 hours. The mixture is washed with aqueous NaHCO$_3$ solution and water, dried MgSO$_4$, and filtered. The organic phase is concentrated and the residue is purified by silica gel flash column chromatography using hexane:ethyl acetate, 50:1 as the eluent. The target fractions are concentrated and dried under vacuo to give the title compound.

EXAMPLE 138

Preparation of 2,10-(bis-o-nitrophenylsulfonyl)-7-(N-t-Boc)- 2,7,10-triaza-3-oxaundecane)[11](2,6)-cyclohexanophane A mixture of cis-1,2-bis-(bromomethyl)cyclohexane (1.67 g, 6.2 mmol), cesium carbonate (8.2 g, 25 mmol, 4 eq) and N1[(t-Boc)-3-((N-o-nitrophenylsulfonyl)O-amino) propanol-1- yl]-N2-(o-nitrophenylsulfonyl)diaminoethane 77 (3.80 g, 6.2 mmol, 1 eq) in anhydrous DMF (200 mL) is stirred at room temperature for 48 hours. The solvent is evaporated under reduced pressure and the residue is dissolved in a mixture of water and chloroform. The layers are separated and the aqueous phase is extracted with chloroform. The organic extract is washed with brine, dried (Na$_2$SO$_4$) and concentrated. The residue is purified by flash chromatography on a silica gel column to give the title compound.

EXAMPLE 139

Preparation of 7-(N-t-Boc)-2,7,10-triaza-3-oxaundecane)-[11](2,6)-cyclohexanophane The title compound is prepared as per the procedure of Example 111, using the title compound of Example 138.

EXAMPLE 140

2,11-bis(2-nitrobenzenesulfonyl)diaza-7-(t-Boc) azadodecane- [2.6]cyclohexanophane A mixture of cis-1,2-bis-(bromomethyl)cyclohexane (1.67 g, 6.2 mmol), cesium carbonate (8.2 g, 25 mmol, 4 eq) and N1-[N-(2-nitrobenzenesulfonyl)-2-aminoethyl]-N3-(2-nitrobenzenesulfonyl)-1,3-diaminopropane (Example 108) (3.64 g, 6.2 mmol, 1 eq) in anhydrous DMF (200 mL) is stirred at room temperature for 48 hours. The solvent is evaporated under reduced pressure and the residue is dissolved in a mixture of water and chloroform. The layers are separated and the aqueous phase is extracted with chloroform. The organic extract is washed with brine, dried (Na$_7$SO$_4$) and concentrated. The residue is purified by flash chromatography on a silica gel column to give the title compound.

EXAMPLE 141

2,7,11-triaza-7-(N-t-Boc)-dodecane[2.6]cyclohexanophane

The title compound is prepared as per the procedure of Example 111, using the title compound of Example 140.

EXAMPLE 142

2,11-bis(2-nitrobenzenesulfonyl)diaza-7-(t-Boc) azadodecane- [2.6]cyclohexanophane A mixture of cis-1,2-bis-(bromomethyl)cyclohexane (1.67 g, 6.2 mmol), cesium carbonate (8.2 g, 25 mmol, 4 eq) and N1-[N-(2-nitrobenzenesulfonyl)-3-aminopropan-1-yl]-N4-(2- nitrobenzenesulfonyl)-1,4-diaminobutane (Example 107) (3.81 g, 6.2 mmol, 1 eq) in anhydrous DMF (200 mL) is stirred at room temperature for 23 hours. The solvent is evaporated under reduced pressure and the residue is dissolved in a mixture of water and chloroform. The layers are separated and the aqueous phase is extracted with chloroform. The organic extract is washed with brine, dried (Na$_2$SO$_4$) and concentrated. The residue is purified by flash chromatography on a silica gel column to give the title compound.

EXAMPLE 143

2,7,11-triaza-7-N-(t-Boc)azadodecane[2.6] cyclohexanophane

The title compound is prepared as per the procedure of Example 111, using the title compound of Example 142.

EVALUATION

Procedure 1
Antimicrobial Assay
*Staphylococcus aureus*

*Staphylococcus aureus* is known to cause localized skin infections as a result of poor hygiene, minor trauma, psoriasis or eczema. It also causes respiratory infections, pneumonia, toxic shock syndrome and septicemia. It is a common cause of acute food poisoning. It exhibits rapid emergence of drug resistance to penicillin, cephalosporin, vancomycin and nafcillin.

In this assay, the strain *S. aureus* ATCC 25923 (American Type Culture Collection) is used in the bioassay. To initiate the exponential phase of bacterial growth prior to the assay, a sample of bacteria grown overnight at 37° C. in typtocase soy broth (BBL) is used to reinoculate sample wells of 96-well microtiter plates. The assays are carried out in the 96-well microtiter plates in 150 µL volume with approximately 1×10$^6$ cells per well.

Bacteria in typtocase soy broth (75 µL) is added to the compound mixtures in solution in 75 µL water in the individual well of the microtiter plate. Final concentrations of the compound mixtures are 25 µM, 10 µM and 1 µM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

Procedure 2
Antimicrobial Mechanistic Assay
Bacterial DNA Gyrase

DNA gyrase is a bacterial enzyme which can introduce negative supercoils into DNA utilizing the free energy derived from ATP hydrolysis. This activity is critical during DNA replication and is a well characterized target for antibiotic inhibition of bacterial growth. In this assay, libraries of compounds are screened for inhibition of DNA gyrase. The assay measures the supercoiling of a relaxed plasmid by DNA gyrase as an electrophoretic shift on an agarose gel. Initially all library pools are screened for inhibitory activity at 30 µM and then a dose response analysis is effected with active subsets. Novobiocin, an antibiotic that binds to the β subunit of DNA gyrase is used as a positive control in the assay. The sensitivity of the DNA gyrase assay was determined by titrating the concentration of the know DNA gyrase inhibitor, Novobiocin, in the supercoiling assay. The IC$_{50}$ was determined to be 8 nM, sufficient to identify the activity of a single active species of comparable activity in a library having 30 µM concentration.

Procedure 3
Use of a combinatorial library for identifying metal chelators and imaging agents This procedure is used to identify compounds of the invention from libraries of compounds constructed to include a ring that contains an ultraviolet chromophore. Further the diversity groups attached to the compound bridge are selected from metal binders, coordinating groups such as amine, hydroxyl and carbonyl groups, and other groups having lone pairs of electrons, such that the macromolecules can form coordination complexes with heavy metals and imaging agents. The procedure is used to identify macromolecules for chelating and removing heavy metals from industrial broths, waste stream eluents, heavy metal poisoning of farm animals and other sources of contaminating heavy metals, and for use in identifying imaging agent carriers, such as carriers for technetium 99.

An aliquot of a test solution having the desired ion or imaging agent at a known concentration is added to an aliquot of standard solution of the pool under assay. The UV spectrum of this aliquot is measured and is compared to the UV spectrum of a further aliquot of the same solution lacking the test ion or imaging agent. A shift in the extinction coefficient is indicative of binding of the metal ion or imaging ion to a compound in the library pool being assayed.

Procedure 4

Assay of combinatorial library for $PLA_2$ inhibitors

A preferred target for assay of combinatorially generated pools of compounds is the phospholipase $A_2$ family. Phospholipases $A_2$ ($PLA_2$) are a family of enzymes that hydrolyze the sn-2 ester linkage of membrane phospholipids resulting in release of a free fatty acid and a lysophospholipid (Dennis, E. A., The Enzymes, Vol. 16, pp. 307–353, Boyer, P. D., ed., Academic Press, New York, 1983). Elevated levels of type II $PLA_2$ are correlated with a number of human inflammatory diseases. The $PLA_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. $PLA_2$ is regulated by pro-inflammatory cytokines and, thus, occupies a central position in the inflammatory cascade (Dennis, ibid.; Glaser et al., *TiPs Reviews* 1992, 14, 92; and Pruzanski et al., *Inflammation* 1992, 16, 451). All mammalian tissues evaluated thus far have exhibited $PLA_2$ activity. At least three different types of $PLA_2$ are found in humans: pancreatic (type I), synovial fluid (type II) and cytosolic. Studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath et al., *Inflammation* 1988, 12, 549) or into the articular space of rabbits (Bomalaski et al., *J. Immunol.* 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g. pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott et al., *Science* 1990, 250, 1541). Recently, the crystal structure of $PLA_2$ from human synovial fluid has been determined (Wery et al., *Nature* 1991, 352, 79). The structure clarifies the role of calcium and amino acid residues in catalysis. Calcium acts as a Lewis acid to activate the scissile ester carbonyl bond of 1,2-diacylglycerophospholipids and binds to the lipid, and a His-Asp side chain diad acts as a general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site (Achari et al., *Cold Spring Harbor Symp. Quant. Biol.* 1987, 52, 441; Cho et al., *J. Biol. Chem.* 1988, 263, 11237; Yang et al., *Biochem. J.* 1989, 262, 855; and Noel et al., *J. Am. Chem. Soc.* 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. Evidence favoring this hypothesis comes from studies revealing that rapid changes in $PLA_2$ activity occur concurrently with changes in the fluorescence of a membrane probe (Burack et al., *Biochemistry* 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger et al., *FEBS Lett.* 1989, 252, 73). These studies clearly show that $PLA_2$ binds exclusively at the boundary region between liquid and solid phase lipid. While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e. phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of PLA2 in biochemical assays (Yuan et al., *J. Am. Chem. Soc.* 1987, 109, 8071; Lombardo et al., *J. Biol. Chem.* 1985, 260, 7234; Washburn et al., *J. Biol. Chem.* 1991, 266, 5042; Campbell et al., *J. Chem. Soc., Chem. Commun.* 1988, 1560; and Davidson et al., *Biochem. Biophys. Res. Commun.* 1986, 137, 587), reports describing in vivo activity are limited (Miyake et al., *J. Pharmacol. Exp. Ther.* 1992, 263, 1302).

In one preferred embodiment, macromolecules of the invention are selected for their potential to interact with, and preferably inhibit, the enzyme $PLA_2$. Thus, compounds of the invention can be used for topical and/or systemic treatment of inflammatory diseases including atopic dermatitis and inflammatory bowel disease. In selecting the functional groups, advantage can be taken of $PLA_2$'s preference for anionic vesicles over zwitterionic vesicles. Preferred compounds of the invention for assay for $PLA_2$ include those having aromatic diversity groups to facilitate binding to the cleft of the $PLA_2$ enzyme (Oinuma et al., *J. Med. Chem.* 1991, 34, 2260; Marki et al., *Agents Actions* 1993, 38, 202; and Tanaka et al., *J. Antibiotics* 1992, 45, 1071). Benzyl and 4-hexylbenzyl groups are preferred aromatic diversity groups. $PLA_2$-directed macromolecule compounds of the invention can further include hydrophobic functional groups such as tetraethylene glycol groups. Since the $PLA_2$ enzyme has a hydrophobic channel, hydrophobicity is believed to be an important property of inhibitors of the enzyme.

After each round of synthesis as described in the above examples, the resulting pools of compounds are screened for inhibition of human type II $PLA_2$ enzymatic activity. The assay is effected at the conclusion of each round of synthesis to identify the wining pool from that round of synthesis. Concurrently, the libraries additionally can be screened in other in vitro assays to determine further mechanisms of inhibition.

The pools of the macrocyclic libraries are screened for inhibition of $PLA_2$ in the assay using *E. coli* labeled with $^3H$-oleic acid (Franson et al., *J. Lipid Res.* 1974, 15, 380; and Davidson et al., *J. Biol. Chem.* 1987, 262, 1698) as the substrate. Type II $PLA_2$ (originally isolated from synovial fluid), expressed in a baculovirus system and partially purified, serves as a source of the enzyme. A series of dilutions of each of the library pools is done in water: 10 $\mu$l of each pool is incubated for 5 minutes at room temperature with a mixture of 10 $\mu$l $PLA_2$, 20 $\mu$l 5× $PLA_2$ Buffer (500 mM Tris 7.0–7.5, 5 mM $CaCl_2$), and 50 $\mu$water. Samples of each pool are run in duplicate. At this point, 10 $\mu$l of $^3H$ *E. coli* cells is added. This mixture is incubated at 37° C. for 15 minutes. The enzymatic reaction is stopped with the addition of 50 $\mu$l 2M HCL and 50 $\mu$l fatty-acid-free BSA (20 mg/ml PBS), vortexed for 5 seconds, and centrifuged at high speed for 5 minutes. 165 $\mu$l of each supernate is then put into a scintillation vial containing 6 ml of scintillant (ScintiVerse) and cpms are measured in a Beckman Liquid Scintillation Counter. As a control, a reaction without the combinatorial pool is run alongside the other reactions as well as a baseline reaction containing no macromolecules as well as no $PLA_2$ enzyme. CPMs are corrected for by subtracting the baseline from each reaction data point.

Confirmation of the "winners" is made to confirm that the macromolecule binds to enzyme rather than substrate and that the inhibition of any macromolecule selected is specific for type II $PLA_2$. An assay using $^{14}C$-phosphatidyl ethanolamine ($^{14}C$-PE) as substrate, rather than *E. coli* membrane, is used to insure enzyme rather than substrate specificity. Micelles of $^{14}C$-PE and deoxycholate are incubated with the enzyme and oligomer. $^{14}C$-labeled arachidonic acid released as a result of $PLA_2$-catalyzed hydrolysis is separated from substrate by thin layer chromatography and the radio-active product is quantitated. The "winner" is compared to phosphatidyl ethanolamine, the preferred substrate of human type II $PLA_2$, to confirm its activity. $PLA_2$ from other sources (snake venom, pancreatic, bee venom) and phospholipase C, phospholipase D and lysophospholipase can be used to further confirm that the inhibition is specific for human type II $PLA_2$.

Figure 15:
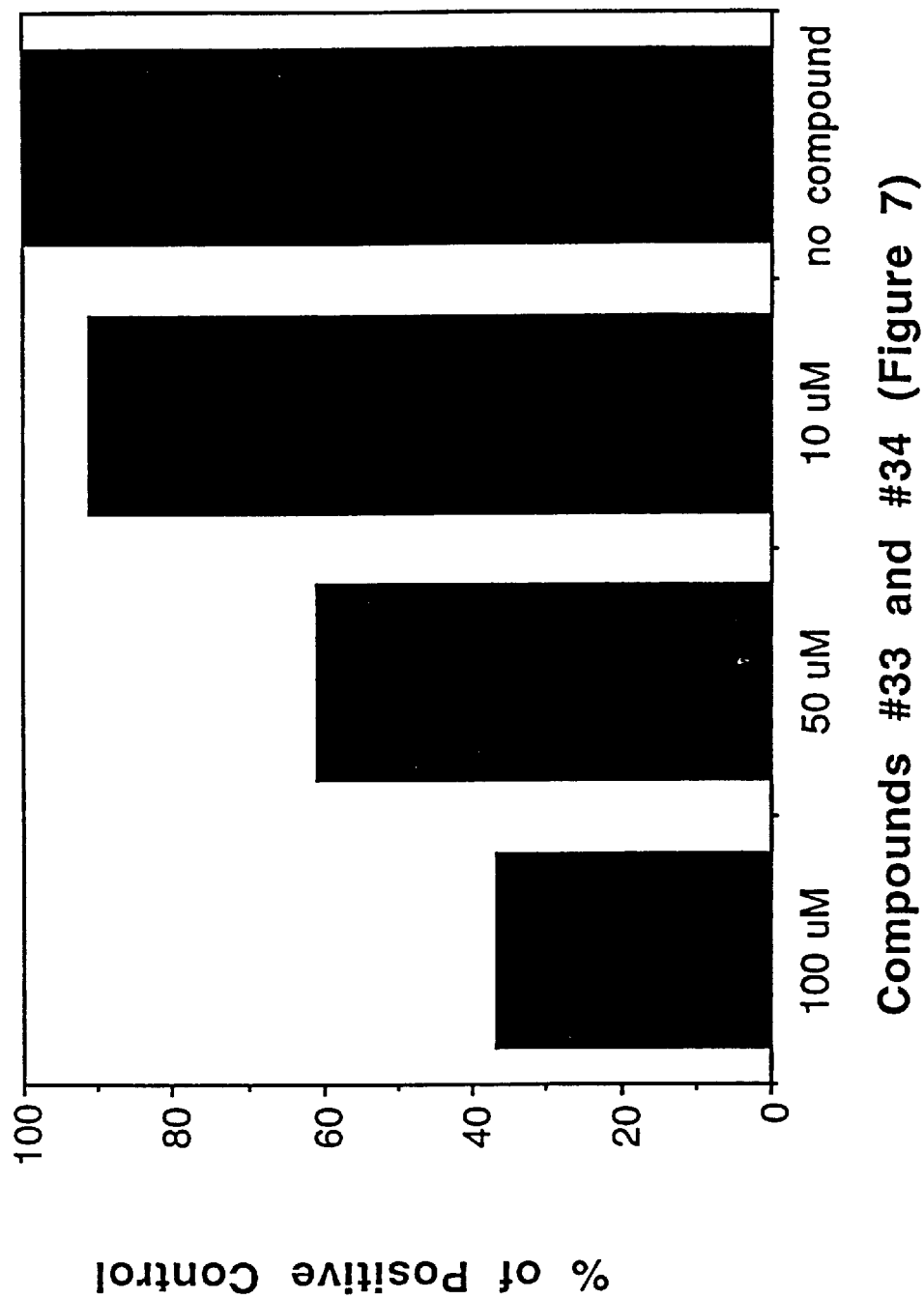
FIG. 15 is shows graphically the results of an *E. coli* PLA2 assay using two macrocyclic compounds of the invention.

The macrocyclic compounds 33 and 34 of Example 90, showed inhibitory activity in the above *E. coli* $PLA_2$ assay. The compounds were assayed as a mixture at 100 $\mu$M, 50 $\mu$M, and 10 $\mu$M (final concentration). FIG. 15 shows the results of the assay in graphic form. Duplicate assay values were averaged, background (no compound, no $PLA_2$) was subtracted and the percentage of the positive control (no compound) was calculated. The $IC_{50}$ for the mixture was approximately 75 $\mu$M.

Procedure 5

Probes for the detection of specific proteins and mRNA in biological samples

For the reliable, rapid, simultaneous quantification of multiple varieties of proteins or mRNA in a biological sample without the need to purify the protein or mRNA from other cellular components, a protein or mRNA of interest from a suitable biological sample, i.e., a blood borne virus, a bacterial pathogen product in stool, urine and other like biological samples, is identified using standard microbiological techniques. A probe comprising a macrocycle compound of the invention is identified by a combinatorial search as noted in the above examples. Preferred for the mRNA probe are compounds synthesized to include "nucleobase" diversity groups (adenine, guanine, thymine and cytosine as the letters) complementary to at least a portion of the nucleic acid sequence of the mRNA. Preferred for the protein probe are compounds synthesized to include chemical functional groups that act as hydrogen bond donors and acceptors, sulfhydryl groups, hydrophobic lipophilic moieties capable of hydrophobic interactions groups and groups capable of ionic interactions. The probe is immobilized on insoluble CPG solid support utilizing the procedure of Pon, R. T., Protocols for Oligonucleotides and Analogs, Agrawal, S., Ed., Humana Press, Totowa, N.J., 1993, p 465–496. A known aliquot of the biological sample under investigation is incubated with the insoluble CPG support having the probe thereon for a time sufficient to hybridize the protein or mRNA to probe and thus to link them via the probe to the solid support. This immobilizes protein or mRNA present in the sample to the CPG support. Other non-immobilized materials and components are then washed off the CPG with a wash media suitable for use with the biological sample. The mRNA on the support is labelled with ethidium bromide, biotin or a commercial radionucleotide and the amount of label immobilized on the CPG support is measured to indicate the amount of mRNA present in the biological sample. In a similar a protein is also labeled and quantified.

Procedure 6

Leukotriene $B_4$ assay

Leukotriene $B_4$ ($LTB_4$) has been implicated in a variety of human inflammatory diseases, and its pharmacological effects are mediated via its interaction with specific surface cell receptors. Library subsets are screened for competitive inhibition of radiolabeled $LTB_4$ binding to a receptor preparation.

A Nenquest™ Drug Discovery System Kit (NEN Research Products, Boston, Mass.) is used to select an inhibitor of the interaction of Leukotriene $B_4$ ($LTB_4$) with receptors on a preparation of guinea pig spleen membrane. [$^3H$] Leukotriene $B_4$ reagent is prepared by adding 5 mL of ligand diluent (phosphate buffer containing NaCl, $MgCl_2$, EDTA and Bacitracin, pH 7.2) to 0.25 mL of the radioligand. The receptor preparation is made by thawing the concentrate, adding 35 mL of ligand diluent and swirling gently in order to resuspend the receptor homogeneously. Reagents are kept on ice during the course of the experiment, and the remaining portions are stored at −20° C.

Library subsets prepared as per general procedure of examples above are diluted to 5 μM, 50 μM and 500 μM in phosphate buffer (1× PBS, 0.1% azide and 0.1% BSA, pH 7.2), yielding final test concentrations of 0.5 μM, 5 μM and 50 μM, respectively. Samples are assayed in duplicate. [³H] LTB₄ (25 μL) is added to 25 μL of either appropriately diluted standard (unlabeled LTB₄) or library subset. The receptor suspension (0.2 mL) is added to each tube. Samples are incubated at 4° C. for 2 hours. Controls include [³H] LTB₄ without receptor suspension (total count vials), and sample of ligand and receptor without library molecules (standard).

After the incubation period, the samples are filtered through GF/B paper that had been previously rinsed with cold saline. The contents of each tube are aspirated onto the filter paper to remove unbound ligand from the membrane preparation, and the tubes washed (2×4 mL) with cold saline. The filter paper is removed from the filtration unit and the filter disks are placed in appropriate vials for scintillation counting. Fluor is added, and the vials shaken and allowed to stand at room temperature for 2 to 3 hours prior to counting. The counts/minute (cpm) obtained for each sample are subtracted from those obtained from the total count vials to determine the net cpm for each sample. The degree of inhibition of binding for each library subset is determined relative to the standard (sample of ligand and receptor without library molecules).

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having one of the structures:

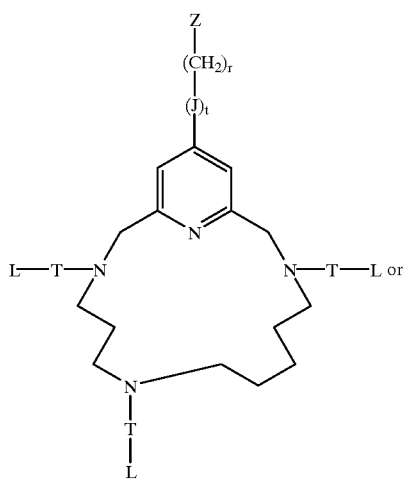

-continued

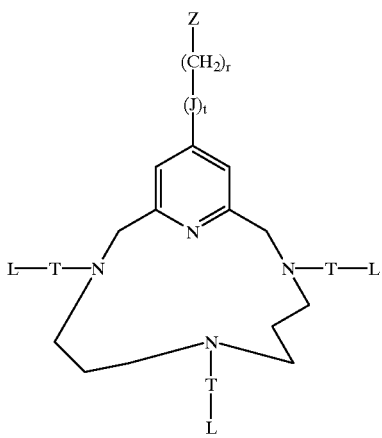

wherein:

Z is H, hydroxyl, amino, thiol, acyl, protected hydroxyl, protected amino, protected thiol, protected acyl or —N(T—L)₂;

r is from 0 to about 8;

J is N, O, S, or a heterocyclic ring system;

t is 0 or 1;

each T is independently a single bond, a methylene group or a group having the structure:

where

R⁶ is =O, S, =NR²;

R⁵ and E, independently, are a single bond, CH=CH, C≡C, O, S, NR³, SO₂, or C₆–C₁₄ aryl;

each R¹, R² and R³ is, independently, H, alkyl or haloalkyl having 1 to about 10 carbon atoms; alkenyl having 2 to about 10 carbon atoms; alkynyl having 2 to about 10 carbon atoms; or aryl having 6 to about 14 carbon atoms;

m and n, independently, are zero to 5;

p is zero or 1;

q is 1 to about 10; and each L is independently, H, C₂–C₁₀ alkyl or substituted alkyl, C₂–C₁₀ alkenyl or substituted alkenyl, C₂–C₁₀ alkynyl or substituted alkynyl, C₄–C₇ carbocyclic alkyl or substituted C₄–C₇ carbocyclic alkyl, alkenyl or alkynyl carbocyclic, substituted alkenyl or alkynyl carbocyclic, or C₆–C₁₄ aryl or substituted aryl where the substituent groups are selected from hydroxyl, amino, alkoxy, alcohol, benzyl, phenyl, nitro, thiol, thioalkoxy, halogen, alkyl, aryl, alkenyl, or alkynyl groups; an ether having 2 to 10 carbon atoms and 1 to 4 oxygen or sulfur atoms; a nitrogen, sulfur or oxygen containing heterocycle; a metal coordination group; a conjugate group; halogen; hydroxyl (OH); thiol (SH); keto (C=O); carboxyl (COOH); amide (CONR¹); amidine (C(=NH)NR¹R²); guanidine (NHC(=NH)NR¹R²); glutamyl R³OOCCH(NR¹R²)(CH₂)₂C(=O)—); nitrate (ONO₂) nitro (NO₂); nitrile (CN); trifluoromethyl (CF₃); trifluoromethoxy (OCF₃); O-alkyl; S-alkyl; NH-alkyl; N-dialkyl; O-aralkyl; S-aralkyl; NH-aralkyl; amino (NH₂); azido (N₃); hydrazino (NHNH₂); hydroxylamino (ONH₂); sulfoxide (SO); sulfone (SO$_2$); sulfide (S—); disulfide (S—S); silyl; a nucleosidic base; an amino acid side chain; a carbohydrate; a drug; or a group capable of hydrogen bonding; and with the proviso that not more than three of said —T—L groups are p-toluenesulfonyl or H, and with the proviso that at least two of said —T—L groups are different.

2. The compound of claim 1 wherein t is 0, r is 0 and Z is H.

3. The compound of claim 1 wherein t is 1 and J is a heterocyclic ring system.

4. The compound of claim 3 wherein said heterocyclic ring system contains at least two nitrogen atoms.

5. The compound of claim 4 wherein said heterocyclic ring system is piperazine.

6. The compound of claim 1 wherein each of said —T—L groups is different from the other of said —T—L groups.

* * * * *

UNITED STATES PATENT AND TRADEMARK OFFICE
CERTIFICATE OF CORRECTION

PATENT NO. : 6,107,482
DATED : August 22, 2000
INVENTOR(S) : Cook et al.

It is certified that error appears in the above-identified patent and that said Letters Patent is hereby corrected as shown below:

Title page,
Second column, "Carell T. et al." reference, please delete "Syntehsis" and insert therefor -- Synthesis --.

Column 5,
Line 4, please delete "$(CH_2)^2C(=)-)$" and insert therefor -- $(CH_2)^2(=O)-)$ --.

Column 15,
Line 21, please delete "hyroxyl" and insert therefor -- hydroxyl -- .

Column 18,
Line 29, please delete "benzylcabazide" and insert therefor -- benzylcarbazide --.

Column 21,
Line 25, please delete "a-position" and insert therefor -- α-position --.
Line 40, please delete "C-C" and insert therefor -- C≡C --.

Column 26,
Line 12, please delete "with" and insert therefor -- and --.

Column 30,
Line 55, please delete "Bb" and insert therefor -- 8b --.

Column 32,
Line 17, please delete "N-(2-o-p-toluenesulfonylethyl)" and insert therefor
-- N-(2-O-p-toluenesulfonylethyl) --.

Column 33,
Lines 34 & 35, please delete "(800 mL)" and insert therefor -- (~800mL) --.

Column 36,
Line 3, please delete "$Ch_z$" and insert therefor -- $CH_2$ --.

Column 38,
Line 14, please delete "Acetaldehydo" and insert therefor -- Acetaldehydro --.

Column 46,
Line 56, please delete "Fromaldehyde" and insert therefor -- Formaldehyde --.

UNITED STATES PATENT AND TRADEMARK OFFICE
CERTIFICATE OF CORRECTION

PATENT NO.   : 6,107,482
DATED        : August 22, 2000
INVENTOR(S)  : Cook et al.

It is certified that error appears in the above-identified patent and that said Letters Patent is hereby corrected as shown below:

Column 53,
Line 5, please delete "hyroxyamide" and insert therefor -- hydroxyamide --.

Column 58,
Line 62, please delete "8" and insert therefor -- $\delta$ --.

Column 59,
Line 5, please delete "Hunig's" and insert therefor -- Hünig's --.

Column 60,
Line 1, please delete "(Cl$_4$H$_{25}$N$_4$" and insert therefor -- (C$_{14}$H$_{25}$N$_4$ --.

Signed and Sealed this

Twenty-sixth Day of March, 2002

Attest:

Attesting Officer

JAMES E. ROGAN
*Director of the United States Patent and Trademark Office*